US007838493B2

(12) United States Patent
Soreq et al.

(10) Patent No.: US 7,838,493 B2
(45) Date of Patent: Nov. 23, 2010

(54) ACETYLCHOLINESTERASE (ACHE)-DERIVED PEPTIDE AS AN INDUCER OF GRANULOCYTOPOIESIS, USES AND METHODS THEREOF

(75) Inventors: Hermona Soreq, Jerusalem (IL); Dan Grisaru, Herzliya (IL); Varda Deutsch, Jerusalem (IL); Chava Perry, Ramat Gan (IL); Marjorie Pick, Victoria (AU)

(73) Assignees: Yissum Research Development Company of the Hebrew University of Jerusalem, Jerusalem (IL); Medical Research Fund at the Tel Aviv Sourasky Medical Center, Tel Aviv (IL)

( * ) Notice: Subject to any disclaimer, the term of this patent is extended or adjusted under 35 U.S.C. 154(b) by 675 days.

(21) Appl. No.: 10/589,116

(22) PCT Filed: Feb. 10, 2005

(86) PCT No.: PCT/IL2005/000185

§ 371 (c)(1),
(2), (4) Date: May 1, 2007

(87) PCT Pub. No.: WO2005/077398

PCT Pub. Date: Aug. 25, 2005

(65) Prior Publication Data

US 2007/0224181 A1    Sep. 27, 2007

(30) Foreign Application Priority Data

Feb. 12, 2004 (IL) ..................................... 160376

(51) Int. Cl.
*A61K 38/00* (2006.01)
(52) U.S. Cl. ........................................................ 514/12
(58) Field of Classification Search ........................ None
See application file for complete search history.

(56) References Cited

U.S. PATENT DOCUMENTS

2003/0036632 A1* 2/2003 Soreq et al. ................. 530/350

FOREIGN PATENT DOCUMENTS

| IL | 130224 | 2/2004 |
|---|---|---|
| WO | WO-00/73427 | 12/2000 |

OTHER PUBLICATIONS

Abo, T. and Kawamura, T., Ther. Apher., 2002, pp. 348-357, vol. 6.
Abramson, N. and Melton, B., Am. Fam. Physician, 2000, pp. 2053-2060., vol. 62.
Basser, R.L. et al., Blood, 2002, pp. 2599-2602, vol. 99.
Bassini, A. et al., Blood, 1999, pp. 1178-1188, vol. 93.
Birikh, K.R. et al, RNA Society, 1997, pp. 429-437, vol. 3.
Borovikova, L.V. et al., Nature, 2000, pp. 458-462, vol. 405.
Brenner et al., FASEB J, 2003, pp. 214-22, vol. 17(2).
Busslinger, M., Ann. Rev. Immunol., 2004, pp. 55-79, vol. 22.
Chan, R.Y.Y. et al., J. Biol. Chem., 1998, pp. 9727-9733, vol. 273.
Craig, W. et al., Br. J. Haematol., 1994, pp. 24-30, vol. 88.
Delgado, I. et al., Gynecol. Obstet. Invest., 1994, pp. 227-235, vol. 38.
Deutsch, V. et al., Exp. Hematol., 2002, pp. 1153-1161, vol. 30.
Erb, C. et al., J. Neurochem., 2001, pp. 638-646, vol. 77.
Flores-Flores, C. et al., J. Neural Transm., 2002, pp. 165-179, vol. 62(supp).
Gainsford, T. et al., Blood, 2000, pp. 528-534, vol. 95.
Grisaru, D. et al., Mol. Cell Biol., 1999, pp. 788-795, vol. 19.
Grisaru, D. et al., Molecular Medicine, 2001, pp. 93-105, vol. 7.
Guenechea, G. et al., Blood, 1999, pp. 1097-1105, vol. 93.
Hanada and Yoshimura, Cytokine Growth Factor Rev., 2002, pp. 413-421, vol. 13.
Hellstrom-Lindahl, E. and Nordberg, A., J. Neuroimmunol., 1996, pp. 139-144, vol. 68.
Ishibashi, T. et al., Proc. Natl. Acad. Sci. U.S.A., 1989, pp. 5953-5957, vol. 86.
Jackson, C.W., Blood, 1973, pp. 413-421, vol. 42.
Johnsson, B. et al., Anal. Biochem., 1991,pp. 268-277, vol. 198.
Kanamaru, S. et al, Stem Cells, 2000, pp. 190-195, vol. 18.
Kaser, A. et al., Blood, 2001, pp. 2720-2725, vol. 98.
Kawashima, K. and Fuji, T., Pharmacol Ther., 2000, pp. 29-48, vol. 86.
Kiecolt-Glaser, J.K. et al., Proc. Natl. Acad. Sci. U.S.A., 2003, pp. 9090-9095, vol. 100.
Kuter, D.J., Transfusion, 2002, pp. 279-283, vol. 42.
Lagasse, E. and Weissman, I.L., J. Immunol. Methods, 1996, pp. 139-150, vol. 197.
Lev-Lehman, E. et al., Blood, 1997, pp. 3644-3653, vol. 89.
Li, K. et al., Br. J. Haematol., 1999, pp. 178-185, vol. 104.
Li, Y. et al., J. Neurosci., 2000, pp. 149-155, vol. 20.
Marchisio, M. et al., Anat. Rec., 1999, pp. 7-14, vol. 255.
Mastorakos, G. and Ilias, I., Ann. NY Acad. Sci., 2000, pp. 95-106, vol. 900.
Miller, G.E. et al., Health Psychol., 2002, pp. 531-541, vol. 21.
Mita, Y. et al., Eur. J. Pharmacol., 1996, pp. 121-127, vol. 297.
Nagata, Y. et al., Thromb. Haemost., 1997, pp. 808-814, vol. 77.
Nakashima, K. et al., Semin Hematol., 1998, pp. 210-221, vol. 35.
Nitsche, A. et al., Haematologica, 2001, pp. 693-699, vol. 86.
Oshevski, S. et al., Biochem. Biophys. Res. Commun., 1999, pp. 603-609, vol. 263.

(Continued)

*Primary Examiner*—Suzanne M. Noakes
(74) *Attorney, Agent, or Firm*—Martin Fleit; Paul D. Bianco; Fleit Gibbons Gutman Bongini & Bianco PL

(57) ABSTRACT

The present invention describes the use of an AChE-R-derived peptide, also known as ARP, as an inducer of hemopoietic cell differentiation and expansion, specifically for the granulocytic population. In addition, the use of ARP as an inducer of thrombopoietin and pro-inflammatory cytokines is also presented. ARP may further be used in the pre-transplant priming of hematopoietic stem cells. Other uses and methods utilizing ARP are also described herein.

6 Claims, 26 Drawing Sheets

OTHER PUBLICATIONS

Perry, C. et al., Neoplasia, 2004, pp. 279-286, vol. 6(3).
Pick, M. et al., Br. J. Haematol., 1998, pp. 639-650, vol. 103.
Pick, M. et al., Ann. NY Acad. Sci., 2004, pp. 85-95, vol. 1018.
Pick, M. et al., Exp. Hematol., 2002, p. 1079, vol. 30.
Porcellini, A. et al., Int. J. Cell Cloning, 1983, pp. 92-104, vol. 1.
Racke, F.K. et al., J. Biol. Chem., 2001, pp. 522-528, vol. 276.
Reizenstein, P., Br. J. Haematol., 1979, pp. 329-334, vol. 43.
Rojnuckarin, P. et al., Blood, 2001, pp. 154-161, vol. 97.
Rojnuckarin, P. et al., J. Biol. Chem., 2001, pp. 41014-41022, vol. 276.
Sklan, E.H. et al., Proc. Natl. Acad. Sci. U.S.A., 2004, pp. 5512-5517, vol. 101(15).
Soreq, H. and Seidman, S., Nat. Rev. Neurosci., 2001, pp. 294-302, vol. 2.
Sternfeld, M. et al., J. Neurosci., 1998, pp. 1240-1249, vol. 18.
Sternfeld, M. et al., J. Physiol. Paris, 1998, pp. 249-255, vol. 92.
Sternfeld, M. et al., Proc. Natl. Acad. Sci. U.S.A., 2000, pp. 8647-8652, vol. 97.
Stowe, R. P. et al., J. Leukoc. Biol., 1999, pp. 179-186, vol. 65.
Szelenyi et al., Immunol. Letter, 1987, pp. 49-54, vol. 16.
Szelenyi et al., Br. J. Haematol., 1982, pp. 241-245, vol. 50.
Tavassoli, M., Blood Cells, 1991, pp. 269-281, vol. 17.
Teramura, M. et al., Cancer Chemother. Pharmacol., 1996, pp. S99-S102, vol. 38(supp).
Toft, P. et al., Apmis, 1994, pp. 43-48, vol. 102.
Topilko and Caillou, Blood, 1985, pp. 891-895, vol. 66.
Tracey, K.J., Nature, 2002, pp. 853-859, vol. 420.
Tuimala, R. et al., Br. J. Obstret. Gynecol., 1976, pp. 707-710, vol. 83.
Wanahita, A. et al., Clin. Infect. Dis., 2002, pp. 1585-1592, vol. 34.
Wang, H. et al., Nature, 2003, pp. 384-388, vol. 421.
Wilson et al., J. Am. Geriatr. Soc., 2002, pp. 2041-2056, vol. 50.
Xu, Z. and Weiss, A., Nat. Immunol., 2002, pp. 764-771, vol. 3.
Zahorec, R., Bratisl. Lek. Listy., 2001, pp. 5-14, vol. 102.
Zhang, X.J. et al., Cell Death Differ., 2002, pp. 790-800, vol. 9.
Deutsch, V. et al., Blood, 2001, p. 73a, vol. 91 (11—part1).
International Search Report for PCT/IL05/000185.
International Prelim Report on Patentability for PCT/IL05/000185.

* cited by examiner

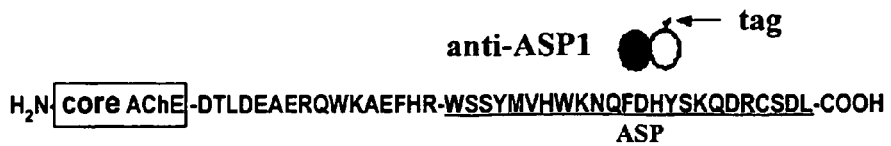
Fig. 1A
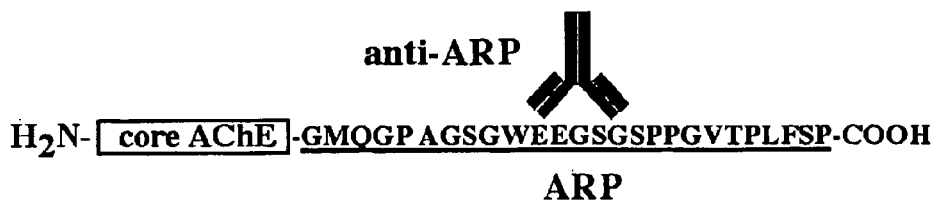
Fig. 1B
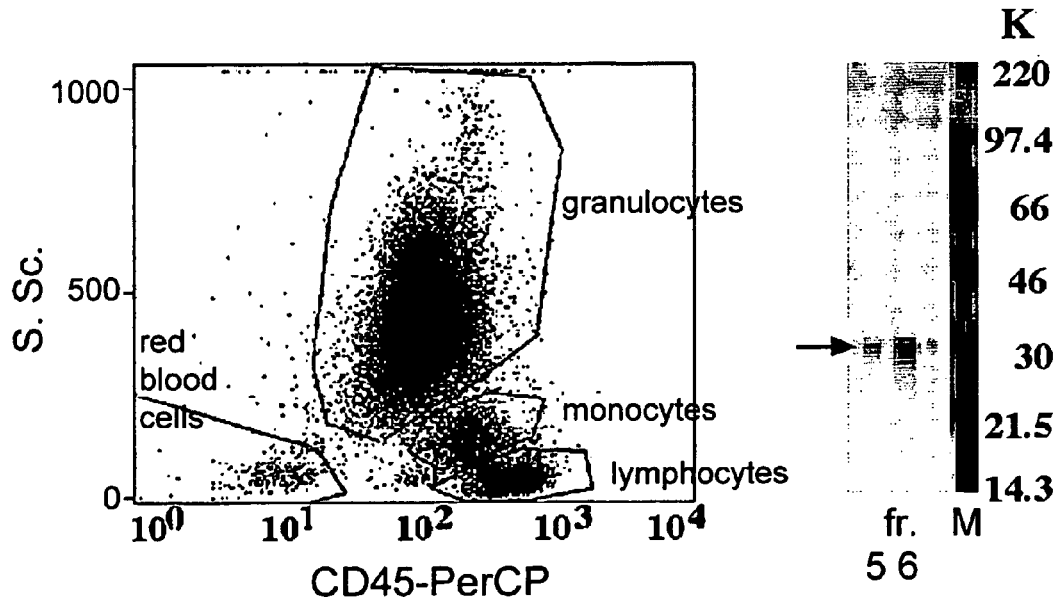
Fig. 1C
Fig. 1D

| Fig. 2C | | G | M | L | R |
|---|---|---|---|---|---|
| CB | % pos. | 30 | 20 | 20 | 100 |
| | int. | + | ++ | + | +++ |
| AB | % pos. | 60 | 60 | 42 | 100 |
| | int. | ++ | ++ | ++ | + |
| PPB | % pos. | 70 | 67 | 12 | 100 |
| | int. | +++ | ++ | ++ | + |

Fig. 7A
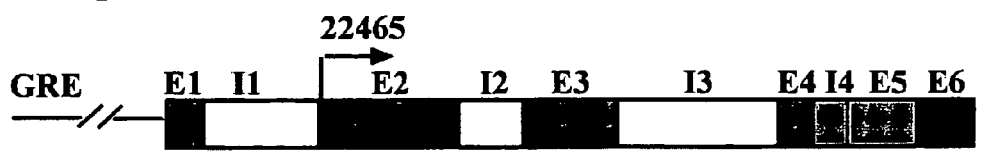
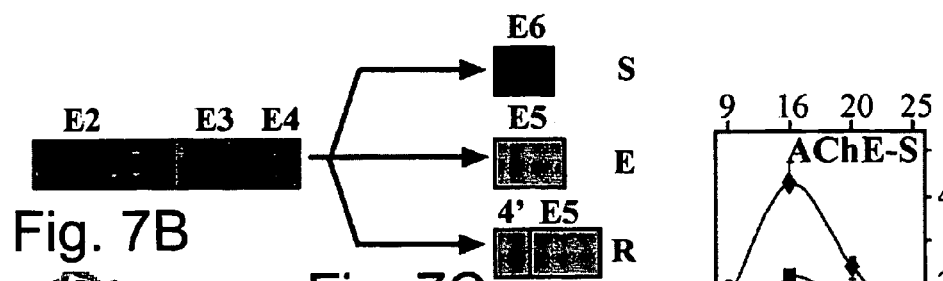
Fig. 7B
Fig. 7C
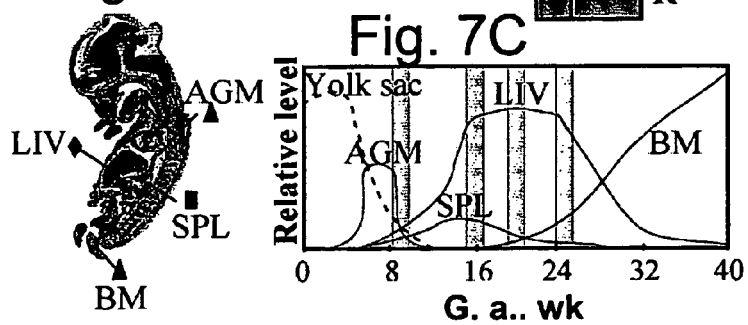
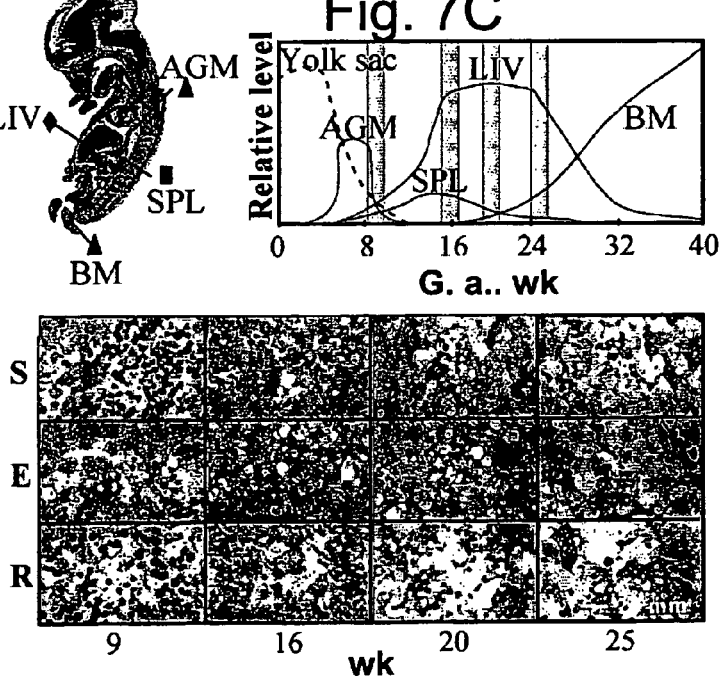
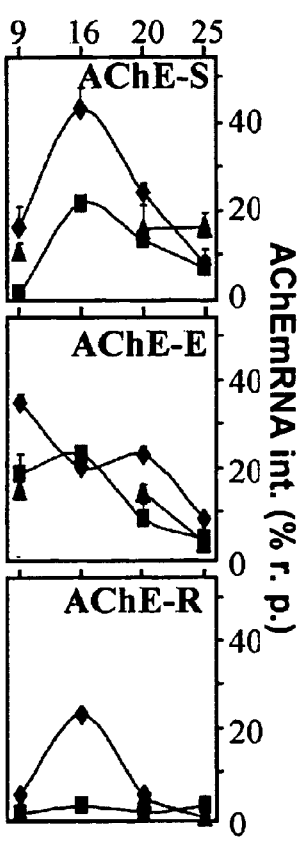
Fig. 7D
Fig. 7E

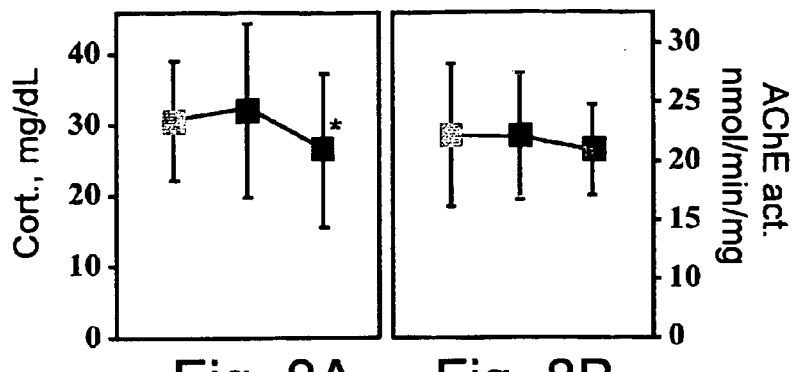
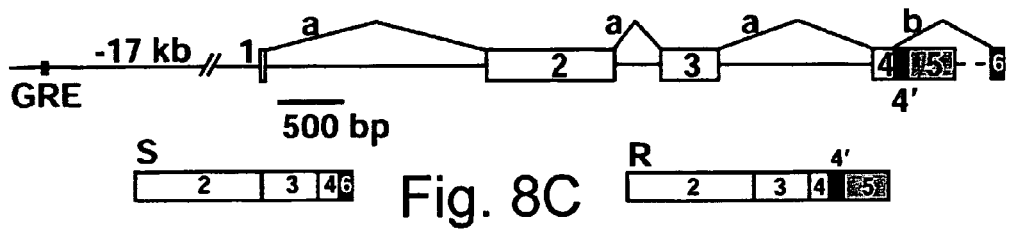
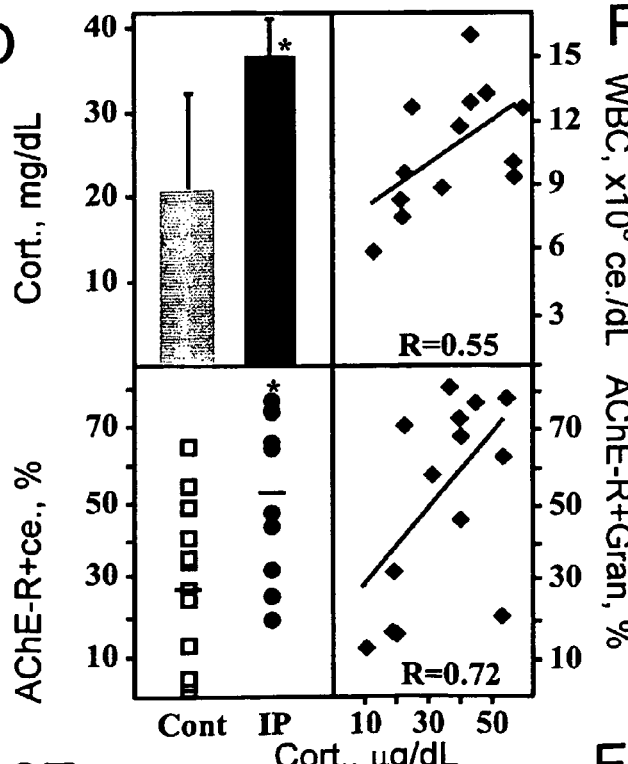
Fig. 8A  Fig. 8B
Fig. 8C
Fig. 8D  Fig. 8E
Fig. 8F  Fig. 8G

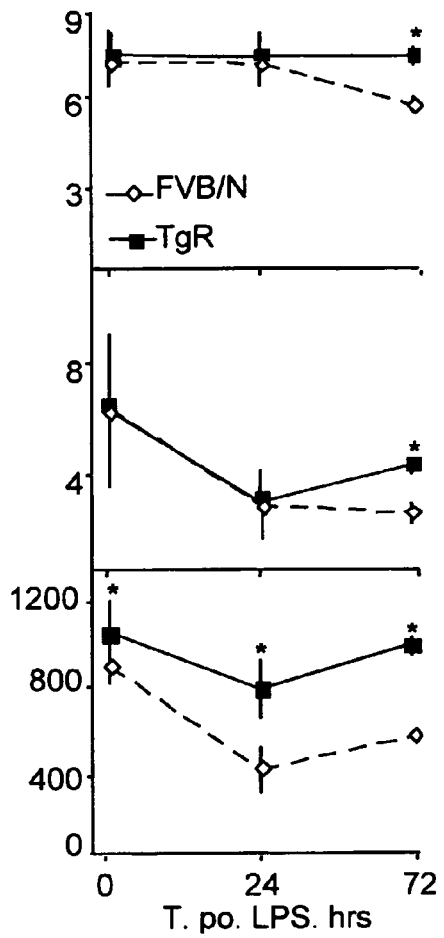
Fig. 16A
Fig. 16B
Fig. 16C
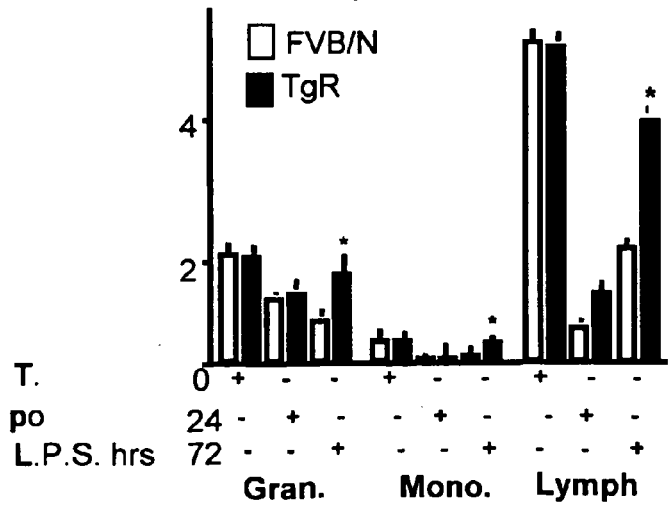
Fig. 16D

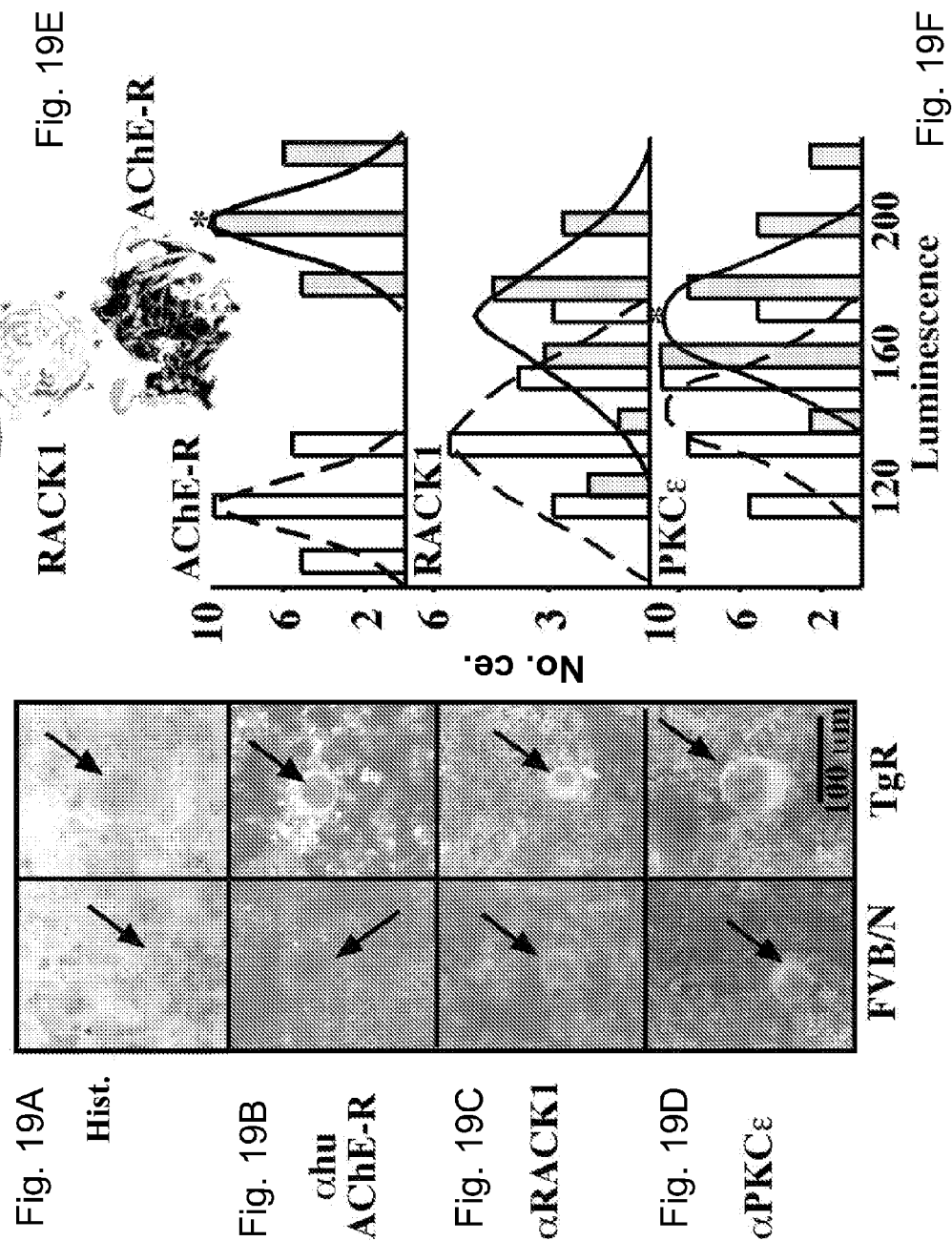

SEQUENCE LISTING

```
<160> NUMBER OF SEQ ID NOS: 20

<210> SEQ ID NO 1
<211> LENGTH: 26
<212> TYPE: PRT
<213> ORGANISM: Homo sapiens

<400> SEQUENCE: 1

Gly Met Gln Gly Pro Ala Gly Ser Gly Trp Glu Glu Gly Ser Gly Ser
1               5                   10                  15

Pro Pro Gly Val Thr Pro Leu Phe Ser Pro
            20                  25

<210> SEQ ID NO 2
<211> LENGTH: 40
<212> TYPE: PRT
<213> ORGANISM: Homo sapiens

<400> SEQUENCE: 2

Asp Thr Leu Asp Glu Ala Glu Arg Gln Trp Lys Ala Glu Phe His Arg
1               5                   10                  15

Trp Ser Ser Tyr Met Val His Trp Lys Asn Gln Phe Asp His Tyr Ser
            20                  25                  30

Lys Gln Asp Arg Cys Ser Asp Leu
        35                  40

<210> SEQ ID NO 3
<211> LENGTH: 23
<212> TYPE: DNA
<213> ORGANISM: Artificial Sequence
<220> FEATURE:
<223> OTHER INFORMATION: Primer sequences-GATA1+

<400> SEQUENCE: 3
tcttctctcc cactgggagc cct                                           23
```

```
<210> SEQ ID NO 4
<211> LENGTH: 23
<212> TYPE: DNA
<213> ORGANISM: Artificial Sequence
<220> FEATURE:
<223> OTHER INFORMATION: Primer sequences-GATA1-

<400> SEQUENCE: 4
cttcttgggc cggatgagag gcc                                           23

<210> SEQ ID NO 5
<211> LENGTH: 20
<212> TYPE: DNA
<213> ORGANISM: Artificial Sequence
<220> FEATURE:
<223> OTHER INFORMATION: Primer sequences-LM02+

<400> SEQUENCE: 5
tggatgaggt gctgcagata                                               20

<210> SEQ ID NO 6
<211> LENGTH: 20
<212> TYPE: DNA
<213> ORGANISM: Artificial Sequence
<220> FEATURE:
<223> OTHER INFORMATION: Primer Sequences-LM02-

<400> SEQUENCE: 6
cccattgatc ttggtccact                                               20

<210> SEQ ID NO 7
<211> LENGTH: 20
<212> TYPE: DNA
<213> ORGANISM: Artificial Sequence
<220> FEATURE:
<223> OTHER INFORMATION: Primer sequence - RUNX1/AML1+

<400> SEQUENCE: 7
acttcctctg ctccgtgcta                                               20

<210> SEQ ID NO 8
<211> LENGTH: 21
<212> TYPE: DNA
<213> ORGANISM: Artificial Sequence
<220> FEATURE:
<223> OTHER INFORMATION: Primer sequence-RUNX1/AML1-

<400> SEQUENCE: 8
gtccactgtg attttgatgg c                                             21

<210> SEQ ID NO 9
<211> LENGTH: 20
<212> TYPE: DNA
<213> ORGANISM: Artificial Sequence
<220> FEATURE:
<223> OTHER INFORMATION: Primer sequence-PU.1+

<400> SEQUENCE: 9
gatggagaaa gccatagcga                                               20

<210> SEQ ID NO 10
<211> LENGTH: 20
<212> TYPE: DNA
<213> ORGANISM: Artificial Sequence
<220> FEATURE:
<223> OTHER INFORMATION: Primer sequence-PU.1-
```

```
<400> SEQUENCE: 10
ttgtgcttgg acgagaactg                                             20

<210> SEQ ID NO 11
<211> LENGTH: 25
<212> TYPE: DNA
<213> ORGANISM: Artificial Sequence
<220> FEATURE:
<223> OTHER INFORMATION: Primer sequence-STAT5b+

<400> SEQUENCE: 11
gggactcaat agatcttgat aatcc                                       25

<210> SEQ ID NO 12
<211> LENGTH: 25
<212> TYPE: DNA
<213> ORGANISM: Artificial Sequence
<220> FEATURE:
<223> OTHER INFORMATION: Primer sequence-STAT 5b-

<400> SEQUENCE: 12
aactgagctt ggatccgcag gctct                                       25

<210> SEQ ID NO 13
<211> LENGTH: 22
<212> TYPE: DNA
<213> ORGANISM: Artificial Sequence
<220> FEATURE:
<223> OTHER INFORMATION: Primer sequence-Actin +

<400> SEQUENCE: 13
caattccatc atgaagtgtg ac                                          22

<210> SEQ ID NO 14
<211> LENGTH: 20
<212> TYPE: DNA
<213> ORGANISM: Artificial Sequence
<220> FEATURE:
<223> OTHER INFORMATION: Primer sequence-Actin -

<400> SEQUENCE: 14
atcttgatct tcatggtgct                                             20

<210> SEQ ID NO 15
<211> LENGTH: 22
<212> TYPE: DNA
<213> ORGANISM: Artificial Sequence
<220> FEATURE:
<223> OTHER INFORMATION: Primer Human sense TNF alfa

<400> SEQUENCE: 15
aggaacagca caggccttag tg                                          22

<210> SEQ ID NO 16
<211> LENGTH: 22
<212> TYPE: DNA
<213> ORGANISM: Artificial Sequence
<220> FEATURE:
<223> OTHER INFORMATION: Primer Human antisense TNF alfa

<400> SEQUENCE: 16 aagaccccctt ccagatagat gg                                         22
```

```
-continued

<210> SEQ ID NO 17
<211> LENGTH: 21
<212> TYPE: DNA
<213> ORGANISM: Artificial Sequence
<220> FEATURE:
<223> OTHER INFORMATION: Probe Human TNF alfa (sensor)

<400> SEQUENCE: 17
gcccctccac ccatgtgctc c                                              21

<210> SEQ ID NO 18
<211> LENGTH: 23
<212> TYPE: DNA
<213> ORGANISM: Artificial Sequence
<220> FEATURE:
<223> OTHER INFORMATION: Probe Human TNF alfa (anchor)

<400> SEQUENCE: 18
cacccaccac catcagccgc atc                                            23

<210> SEQ ID NO 19
<211> LENGTH: 21
<212> TYPE: DNA
<213> ORGANISM: Artificial Sequence
<220> FEATURE:
<223> OTHER INFORMATION: Primer Mouse sense TNF alfa

<400> SEQUENCE: 19
ggctttccga attcactgga c                                              21

<210> SEQ ID NO 20
<211> LENGTH: 19
<212> TYPE: DNA
<213> ORGANISM: Artificial Sequence
<220> FEATURE:
<223> OTHER INFORMATION: Primer Mouse antisense TNF alfa

<400> SEQUENCE: 20
ccccggcctt ccaaataaa                                                 19
```

ACETYLCHOLINESTERASE (ACHE)-DERIVED PEPTIDE AS AN INDUCER OF GRANULOCYTOPOIESIS, USES AND METHODS THEREOF

FIELD OF THE INVENTION

The present invention relates generally to the field of hematopoiesis and more specifically to the effect of an AChE-derived peptide on different hematopoietic sub-populations.

BACKGROUND OF THE INVENTION

All publications mentioned throughout this application are fully incorporated herein by reference, including all references cited therein.

Mammalian hematopoietic stem cells develop during embryogenesis and differentiate into the different hematopoietic lineages. After birth, the capacity of myeloid cells to respond to external and/or internal stimuli by the finely tuned production of pro-inflammatory and anti-inflammatory cytokines is gradually acquired, in parallel with the establishment of fully mature lymphocytic immune responses. Interestingly, the responses of both myeloid and lymphoid cell lineages are subject to acetylcholine (ACh) modulation [Kawashima, K., and T. Fujii (2000) *Pharmacol. Ther.* 86:29-48; Tracey, K. J. (2002) *Nature* 420:853-9], which involves the α7 nicotinic ACh receptor [Wang, H. et al. (2003) *Nature* 421:384-8] and are known to be impaired under psychological stress [Miller, G. E. et al. (2002) *Health Psychol* 21:531-41]. However, the putative protein(s) mediating these developmental and stress-induced processes is yet unknown.

Post-stress leukocytosis, i.e. overproduction of white blood cells (WBC), was first described over 50 years ago. Elevated WBC counts occur after diverse stress insults, e.g. shock, blood loss, in post-partum mothers, following space flight or bacterial infection [Delgado, I. et al. (1994) *Gynecol. Obstet. Invest.* 38: 227-235; Reizenstein, P. (1979) *Br. J. Haematol.* 43: 329-334; Stowe, R. P. et al. (1999) *J. Leukoc. Biol.* 65: 179-186; Toft, P. et al. (1994) *Apmis* 102: 43-48; Wanahita, A. et al. (2002) *Clin. Infect. Dis.* 34: 1585-1592]. The initiation of WBC overproduction has been attributed to the elevated serum levels of cortisol, causing both enhanced proliferation and facilitated WBC maturation, predominantly toward the granulocytic lineage [Abramson, N. and Melton, B. (2000) *Am. Fam. Physician* 62: 2053-2060]. However, the increased levels of cortisol, e.g. following the stressful event of delivery, recede within a few hours [Tuimala, R. et al. (1976) *Br. J. Obstet. Gynaecol.* 83: 707-710], and cannot account for the prolongation of leukocytosis, especially since the lifespan of granulocytes is extremely short, with 50% of the granulocytes being replaced by the bone marrow daily [Abo, T. and Kawamura, T. (2002) *Ther. Apher.* 6: 348-357]. The signaling pathways controlling this process therefore remain largely unknown.

Granulocytosis depends upon the production of proinflammatory/hematopoietic cytokines which in peripheral tissues is regulated by acetylcholine (ACh) [Borovikova, L. V. et al. (2000) *Nature* 405: 458-462; Tracey, K. J. (2002) id ibid.]. Under normal conditions, ACh activates α7 ACh nicotinic receptors on macrophages to attenuate pro-inflammatory cytokine secretion at the post-transcriptional level [Wang, H. (2003) id ibid.]. To determine whether post-stress ACh levels can account for the prolonged granulocytosis effect independently of cortisol, and to delineate the cascade of events that enables this process, the inventors studied circulating acetylcholinesterase (AChE). Agents performing this reaction can further be used to control the production of cytokines in patients with failure of such responses.

Hence, inflammation is an example of inducible hematopoiesis, which occurs whenever there is an increased demand for mature blood cells. Upon activation of the inflammatory response, pro-inflammatory cytokines are secreted by cells of the immune system, and induce accelerated production of hematopoietic cells. Lipopolysaccharide (LPS), the main cell wall component of gram-negative bacteria, is an endotoxin that induces an acute inflammatory response, initiating a signal transduction cascade that leads to the release of inflammatory cytokines, which include tumor necrosis factor (TNF)-α, IL-1β, IL-6 and IL-8. These cytokines activate the mobilization of hematopoietic cells from the bone marrow (BM) and set in motion the migration of leukocytes from blood vessel walls, increasing their numbers in the circulation [Lagasse E, Weissman I L. (1996) *J. Immunol. Methods* 197: 139-150]. The net result of this process is an immediate and dramatic increase in the number of circulating peripheral blood (PB) cells, needed to mount the immune response. This results in a compensatory decrease in cell numbers until more cells are produced in the BM [Nagata Y, et al. (1997) *Thromb Haemost.* 77:808-814].

Many factors are involved in abating the inflammatory response allowing hemostasis to return. Acetylcholine (ACh), is one of the recently discovered factors that attenuates the pro-inflammatory cytokine secretion by activating nicotinic receptors on macrophages at the post-transcriptional level [Wang H. et al. (2003) *Nature* 421:384-388]. Circulating acetylcholinesterase (AChE) controls the levels of ACh, suggesting promotion of the inflammatory process under AChE excess [Pick M. et al. (2004) *Ann. NY Acad. Sci.* 1018:85-95]. AChE has three variant forms,—Synaptic (S), Erythrocytic (E) and Readthrough (R), is ubiquitously expressed in hematopoietic cell lineages especially in megakaryocytes (Mks) and erythrocytes [Kawashima K, and Fujii T. (2000) *Pharmacol. Ther.* 86:29-48; Lev-Lehman E. et al. (1997) *Blood* 89:3644-3653; Grisaru D. et al. (2001) *Molecular Medicine* 7:93-105] and is thought to be a potential growth factor for hematopoiesis [Grisaru (2001) id ibid.; Deutsch V. et al. (2002) *Exp. Hematol.* 30:1153-1161].

AChE-R is expressed in multiple embryonic and tumor cells, where it displays morphogenic functions, but it is rarely found in healthy and unstressed adult tissues [Grisaru (1999a) id ibid.; Karpel (1994) id ibid.; Soreq, H. and S. Seidman (2001) *Nat. Rev. Neurosci.* 2:294-302; Grisaru, D. et al. (1999b) *Mol. Cell. Biol.* 19:788-795] or human sera [Brenner et al. (2003) *FASEB J.* 17(2):214-22]. Cortisol induces AChE-R production in cultured CD34+ blood cell progenitors [Grisaru (2001) id ibid.], while $ARP_{26}$, a synthetic peptide designed to mimic the cleavable C-terminal sequence of AChE-R, promotes hematopoietic proliferation in vitro [Grisaru (2001) id ibid.].

The up regulation of AChE expression during megakaryopoiesis was initially reported in rats, where the fraction of AChE-positive BM cells increased following induction of thrombocytopenia [Jackson C W. (1973) *Blood* 42:413-421]. Functional involvement of this enzyme was indicated by suppression of AChE synthesis, which induced transient decreases in murine megakaryocyte progenitors [Lev-Lehman (1997) id ibid.].

Platelet production is a self-regulated process primarily induced by thrombocytopenia where a drastic reduction in platelets stimulates the production of thrombopoietin (TPO). Subsequently, as platelet counts return to normal, TPO is effectively cleared from the circulation, by means of binding to its receptor, c-mpl, and uptake into platelets and megakaryocytes. TPO is the main physiological growth factor for megakaryocyte proliferation, differentiation and platelet production. Nevertheless, c-mpl$^{-/-}$ and TPO$^{-/-}$ knockout mice have a residual 10% of normally functioning megakaryocytes and platelets, which cannot be attributed to IL-6, IL-11 or leukemia inhibitory factor (LIF), which are also known to induce megakaryocyte differentiation [Ishibashi T. et al. (1989) *Proc. Natl. Acad. Sci. USA* 86: 5953-5957; Teramura M., et al. (1996) *Cancer Chemother. Pharmacol.* 38:Suppl: S99-102; Nakashima K. et al. (1998) *Semin. Hematol.* 35: 210-221; Gainsford T. et al. (2000) *Blood* 95: 528-534] suggesting the involvement of other factor(s) in this process.

Pancytopenia and prolonged thrombocytopenia are significant clinical problems for patients undergoing BM transplantation. Engraftment of transplanted BM is usually accomplished within 2 to 3 weeks, during which period the patient is susceptible to life-threatening infections and bleeding. Platelet recovery after autologous stem cells or cord blood (CB) transplantation is significantly delayed (up to 6 weeks post transplant) due to lack of sufficient megakaryocyte precursors in the grafts. The paucity of megakaryocyte progenitor cells in grafts, and not inferior levels of TPO, is the cause for delayed platelet recovery observed post cord blood and autologous transplantation [Kuter D. J. (2002) *Transfusion* 42:279-283; Kanamaru S. et al. (2000) *Stem Cells* 18:190-195].

Thus, within their individual microenvironment, blood cells receive a plethora of external stimuli which influence transcription and processing of many reactive molecules. Particular alternatively spliced AChE variants may be candidates to exert both enzymatic and non-catalytic functions on these cells. The expression of AChE-S in blood cells has been associated with terminal differentiation [Chan, R. Y. Y. et al. (1998) *J. Biol. Chem.* 273:9727-9733] and apoptosis [Zhang, X. J. et al. (2002) *Cell Death Differ.* 9:790-800]. In contrast, AChE-R and the synthetic peptide ARP were associated with stem myeloid cell proliferation [Grisaru (2001) id ibid.; Deutsch et al. (2002) id ibid.].

The present inventors performed a comprehensive study to correctly evaluate the potential contribution of AChE towards differentiation, proliferative or apoptotic events in hematopoiesis, and in inflammatory responses under stress stimuli, specific variants were identified, their levels quantified and their subcellular localization (i.e. on the cell surface and/or intracellular) determined in specific blood cell lineages.

The inventors considered, as a working hypothesis, circulating AChE-R to be a modulator of sustained granulocytosis effects in hematopoietic progenitors. To find out whether AChE-R and/or ARP are associated with post-stress granulocytosis and cytokine production, the inventors initiated a study aimed at delineating the in vivo and ex vivo regulation of AChE-R production in stress-induced myelopoietic processes.

Thus, an aim of the present invention is to provide novel uses for an AChE-derived peptide, as an agent capable of inducing granulopoiesis, as demonstrated in the following Examples.

It is another aim of the present invention to provide a method for the treatment of conditions that induce a low granulocytic cell count, administering said AChE-derived peptide, and compositions thereof, to a subject in need.

Further, the present invention provides methods of evaluating lymphocytic activity, based on the expression of the different AChE forms on lymphocytes.

Other purposes and advantages of the invention will appear as the description proceeds.

SUMMARY OF THE INVENTION

The inventors have demonstrated that overproduction and C-terminal cleavage of the stress-induced AChE-R isoform induced granulocytosis.

In this view, in a first aspect, the present invention provides the use of an AChE-derived peptide, ARP$_{26}$, and any functional fragments thereof, as an agent for the induction of the production of granulocytes, or for the enrichment of the granulocytic cell population, wherein said peptide is denoted by SEQ ID NO:1. The peptide used by the invention comprises the following amino acid sequence:

N'-GMQGPAGSGWEEGSGSPPGVTPLFSP-C'

Said peptide may also be an agent for the induction of repopulation and/or rematuration of granulocytic cell populations, preferably in a subject in need.

In another aspect, the present invention comprises the use of an AChE-derived peptide as an agent for ex vivo or in vitro manipulation of cells to induce granulocyte cell differentiation, wherein said peptide is denoted by SEQ ID NO:1.

The AChE-derived peptide denoted by SEQ ID NO:1, or any functional fragments thereof, are also to be used as an agent for pre-transplant priming of hematopoietic stem cells.

A further use of the AChE-derived peptide ARP$_{26}$, or any functional fragments thereof, is as an inducer of pro-inflammatory cytokines and/or as an inducer of TPO.

In a further aspect, the present invention provides the use of an AChE-derived peptide, or any functional fragments thereof, in the preparation of a pharmaceutical composition for the treatment and/or prevention of conditions that trigger low granulocyte count, wherein said peptide is denoted by SEQ ID NO:1. Said composition may also be used in pre-transplant priming of hematopoietic stem cells. Such conditions may be, for example, leucopemia, acute myeloid leukemia (AML), and particularly neutropenia.

In an even further aspect, the present invention provides a method of treatment of conditions that induce leucopenia, comprising the steps of administrating a therapeutically-effective amount of an AChE-derived peptide or a composition thereof to a subject in need, wherein said AChE-derived peptide is denoted by SEQ ID NO:1.

The invention also refers to an in vivo method for the prevention and/or treatment of conditions wherein lymphocyte activity is reduced, such as chronic stress, autoimmune diseases, inflammation, rheumatoid arthritis, multiple sclerosis (MS), amyotrophic lateral sclerosis (ALS), fibromyalgia, multiple chemical sensitivity, post-irradiation, chemotherapy in a subject in need, comprising administering a therapeutically-effective amount of an AChE-derived peptide, or any functional fragments thereof, to an individual suffering or prone to said conditions, wherein said peptide is denoted by SEQ ID NO:1.

The present invention also discloses a method for detecting changes in the activity of lymphocytes, comprising measuring the expression of AChE-R on the surface of lymphocytes.

The invention provides an ex vivo or in vitro method of prevention and/or treatment of conditions wherein lymphocyte activity is reduced, such as chronic stress, autoimmune diseases, inflammation, rheumatoid arthritis, multiple sclerosis (MS), amyotrophic lateral sclerosis (ALS), fibromyalgia, multiple chemical sensitivity, post-irradiation, chemotherapy in a subject in need, comprising obtaining blood from said subject, isolating immature cells and contacting said cells with an AChE-derived peptide, or any functional fragments thereof, wherein said peptide is denoted by SEQ ID NO:1.

In addition, a method of priming of hematopoietic stem cells pre-transplant is presented, comprising obtaining said cells, isolating from said cells an immature, CD34+ rich population, and exposing said cell population to an AChE-derived peptide, its functional fragments or derivatives, or compositions comprising thereof, wherein said peptide is denoted by SEQ ID NO:1. Most importantly, said cells may be obtained from the subject in need of said transplant or from another donor.

Lastly, the invention also provides a method of inducing adult blood cells to produce cytokines, comprising obtaining said cells from a subject in need of cytokine-producing blood cells, isolating immature cells and contacting said cells with an AChE-derived peptide, wherein said peptide is denoted by SEQ ID NO:1. This method is particularly advantageous for patients with neutropenia.

BRIEF DESCRIPTION OF THE FIGURES

FIG. 1A-1D: Flow cytometric approach to AChE splice variants.

FIG. 1A: C-terminal amino acid sequence unique to the human AChE-S variant; SEQ ID NO:2.

FIG. 1B: C-terminal amino acid sequence unique to the human AChE-R variant; SEQ ID NO:1 (The sequences in A and B share a similar core domain. Note that ASP, but not ARP, includes a C-terminal cysteine residue (asterisk) that enables AchE-S multimerization).

A scFv-myc tagged antibody selected against the C-terminal sequence of AChE-S from a phage display library (anti-ASP1) and a polyclonal antibody produced against synthetic ARP (drawings) enabled specific detection of each of these variants.

FIG. 1C: Flow cytometric sub-classification of hematopoietic cells using anti-CD45. Shown are adult peripheral blood cells divided into lymphocytes, monocytes, granulocytes and red blood cells, depending on their expression of CD45. Each dot corresponds to one cell.

FIG. 1D: Anti-ASP1 scFv purity was verified by gel electrophoresis. Elution from Ni-NTA column with 250 mM imidazole, revealed 30-kDa band (arrow).

Abbreviations: S. Sc., side scatter; fr., fraction.

Figures 2A, 2B:
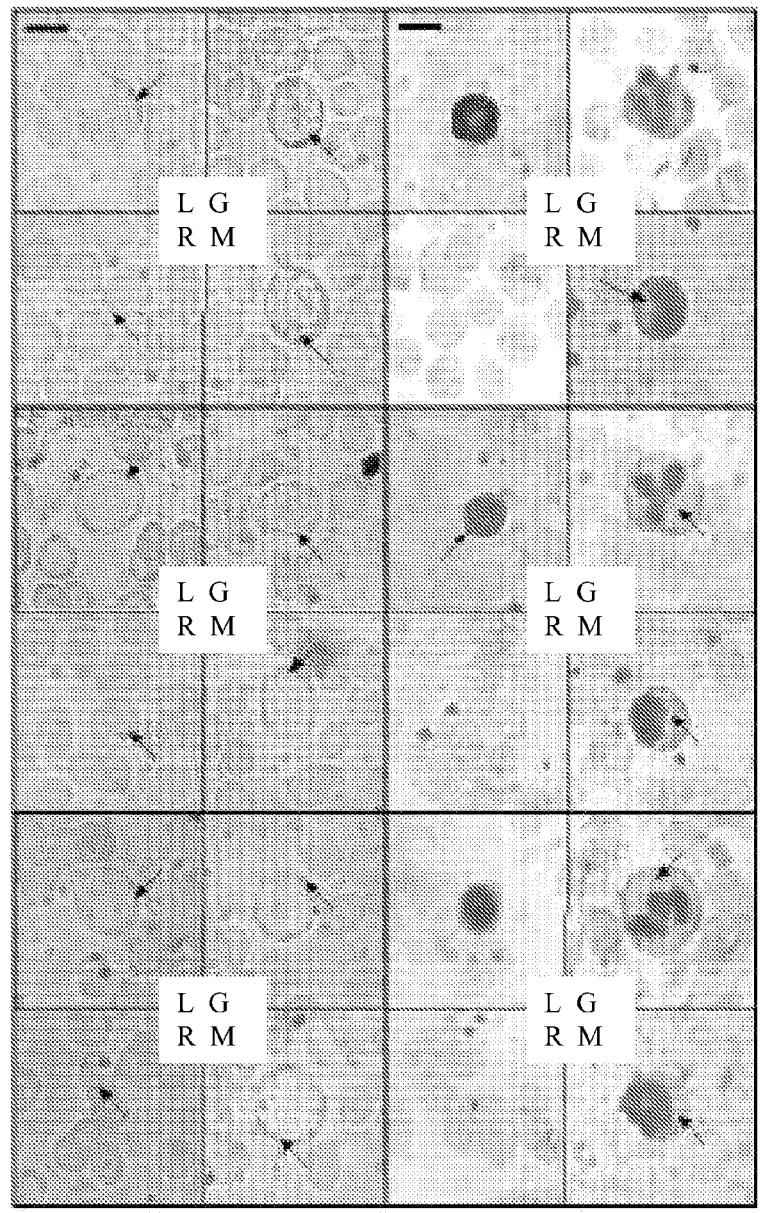

FIG. 2A-2C: Enzymatic AChE activity in hematopoietic blood cells.

FIG. 2A: Cytochemical staining reveals acetylthiocholine hydrolysis activity (brown-gray) in all cell lineages (arrows) from all three sources.

FIG. 2B: Counterstaining with May-Gruenwald's/Giemsa highlights the different characteristic morphologies of the smeared cells. Note gray color of cytochemically positive cells (arrows).

FIG. 2C: Quantitation of cell positive for AChE activity for each blood cell group and arbitrary measurement of brown intensity n=30 cells.

Abbreviations: L, lymphocytes; G, granulocytes; R, red blood cells; M, monocytes; pos., positive; int., intensity.

Figure 3:
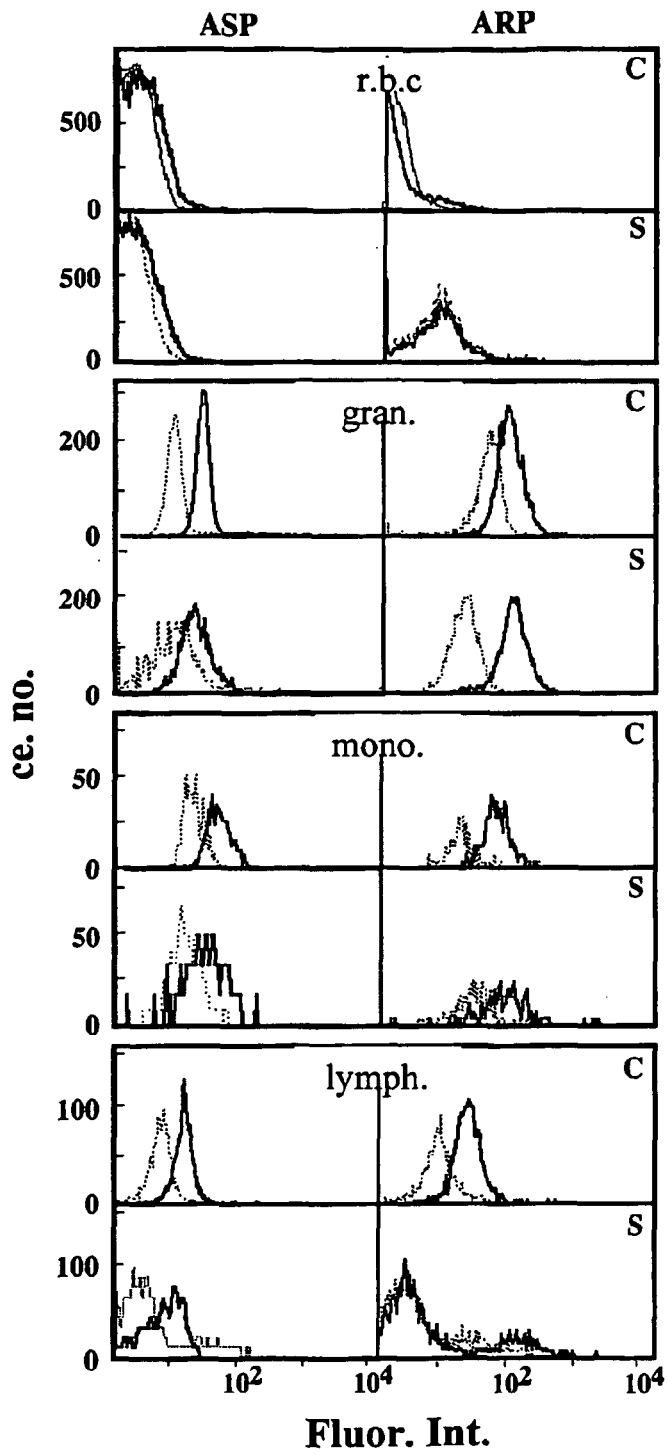

FIG. 3: Cell surface and intracellular AChE-S and -R labeling in post-partum peripheral blood cell populations.

AChE-S and AChE-R were detected using an anti-ASP scFv antibody with a myc tag and anti-myc FITC or a polyclonal rabbit antibody and anti-rabbit FITC, respectively. Positive cells (solid line) were defined by a shift to the right as compared to the control (dashed line) histogram. This figure represents one of 15 reproducible analyses.

Abbreviations: C, Cytoplasmic; S, Surface; rbc, red blood cells; gran., granulocytes; mono., monocytes; lymph., lymphocytes; ce. no., cell number; Fluor. Int., Fluorescence Intensity.

Figure 4A:
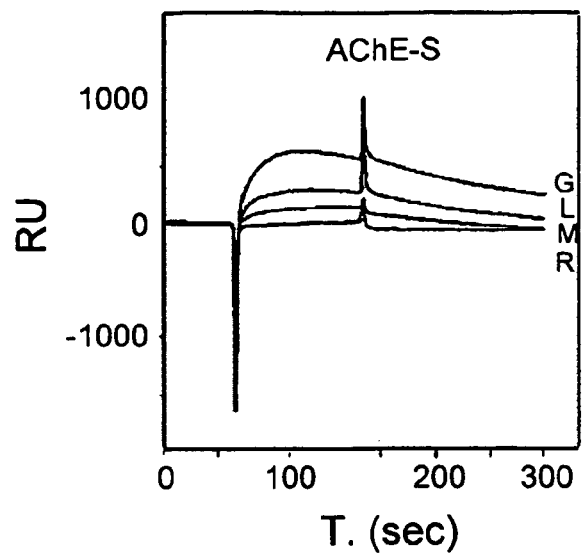
Figure 4B:
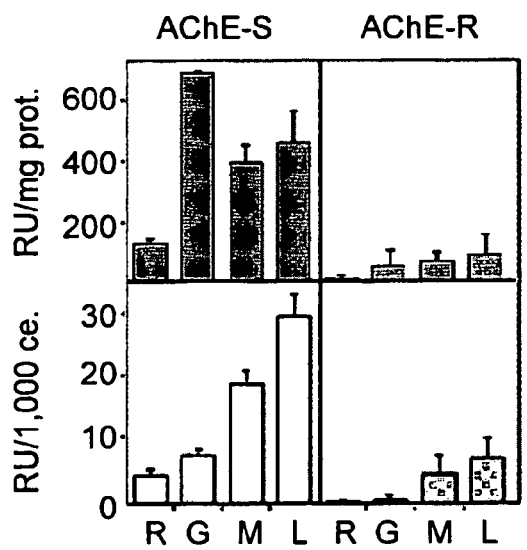
Figure 4C:
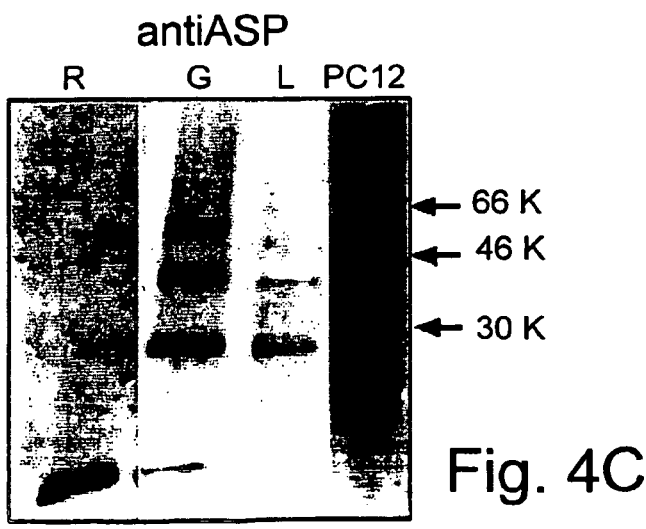

FIG. 4A-4C: Immunochemical analyses of cord blood cell lysates.

AChE-S and -R epitopes were detected in 0.83 mg/ml protein extracts from the three different sub-populations of cord blood.

FIG. 4A: Plasmon resonance traces reflected interactions of anti-ASP1 scFv antibody with extracts of granulocytes (G); lymphocytes (L); monocytes (M) and red blood cells (R). Real time interaction (x-axis) is expressed in RU (y-axis).

FIG. 4B: Shown are the relative contents of AChE-S and -R expressed as RU between the respective antibodies and their epitopes in the different cell lysates, standardized to the amount of total protein in the extract (top) or the number of lysed cells (bottom).

FIG. 4C: Immunoblot using the phage anti-ASP1 and lysates of the noted cell populations. AChE-S and its various cleaved products are labeled. PC12 cells known to express AChE-S were used as a positive control.

Abbreviations: T., time; prot., protein; ce., cells.

Figures 5A, 5B:
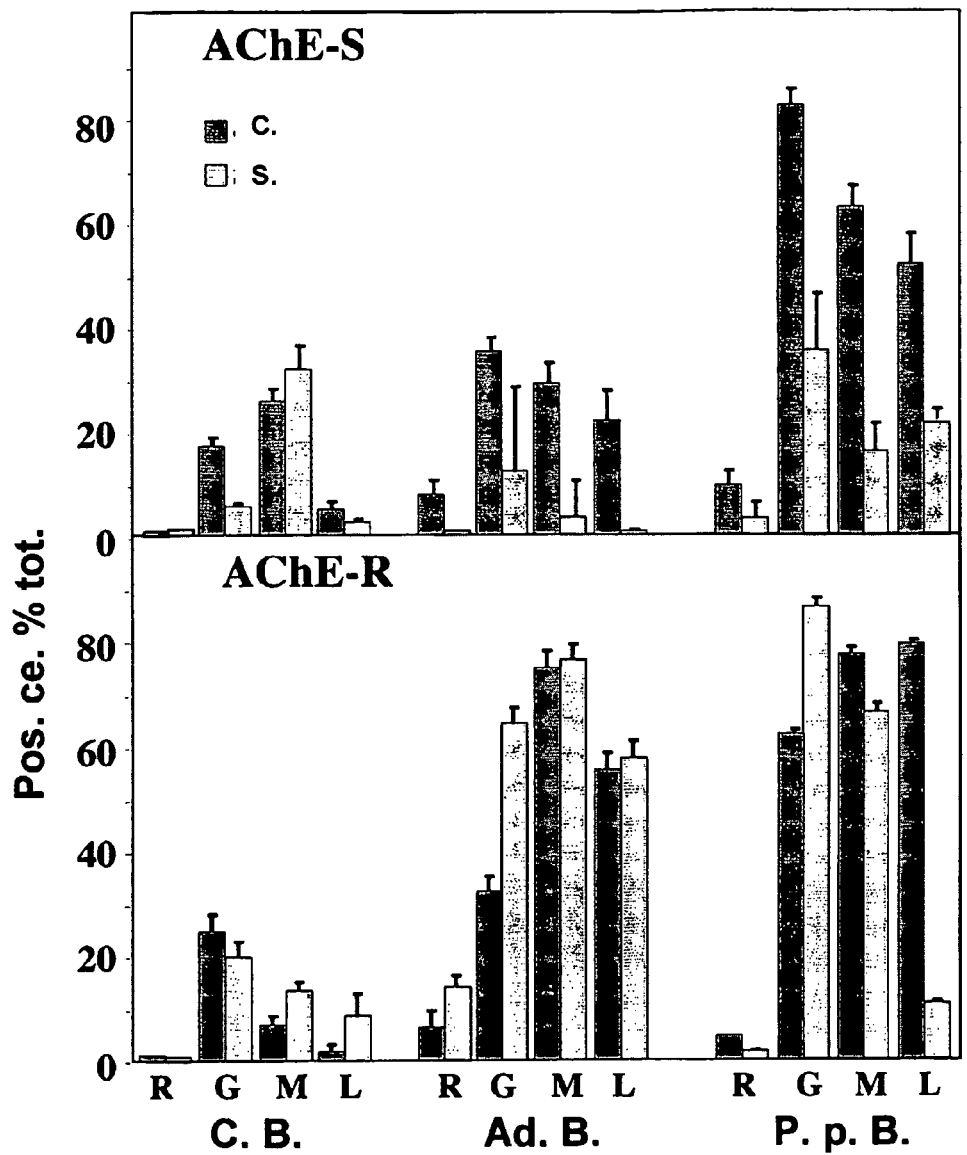

FIG. 5A-5B: Development- and stress-associated expression of AChE variants within blood cell populations.

Positive cell fractions were quantified by flow cytometry and divided into cells with the corresponding variants in the cytosol and on the surface of the noted cell populations. Columns present the percent of positive cells in 15 samples from each source (mean±standard error of the mean). Non-specific signals were subtracted. Solid and crosshatched bars represent cytoplasmic and surface expressions, respectively.

FIG. 5A: AChE-S
FIG. 5B: AChE-R

Abbreviations: R, red blood cells; G, granulocytes; M, monocytes; L, lymphocytes; Pos., positive; ce., cells; tot., total; c., cytoplasmic; s., surface; C.B., cord blood; Ad. B., adult blood; PPB; post-partum blood.

Figure 6A:
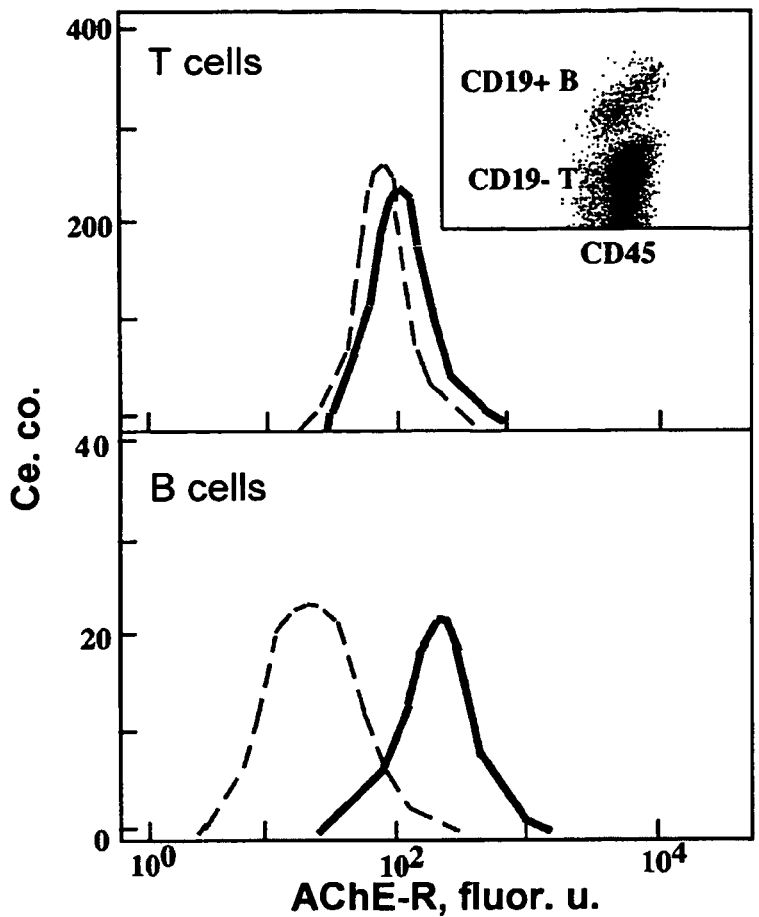
Figure 6B:
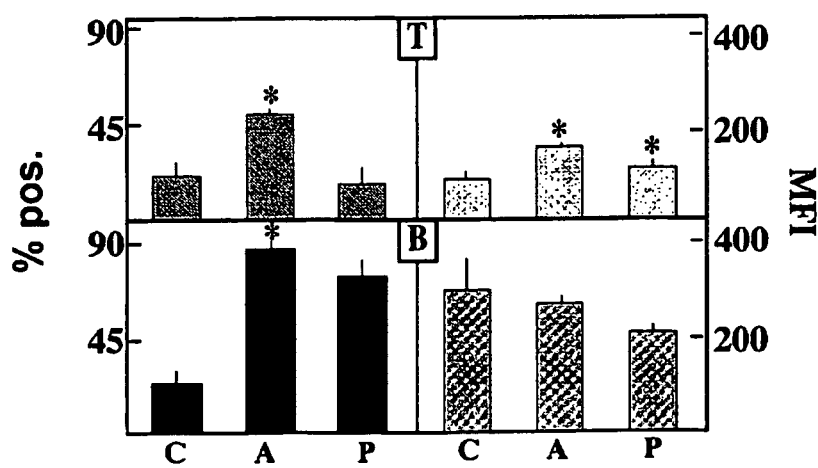

FIG. 6A-6B: Surface AChE-R on lymphocyte subpopulations.

FIG. 6A: Surface AChE-R was detected in T and B lymphocyte sub-populations on all three sources analyzed. Shown are cells from adult peripheral blood. Upper panel is surface AChE-R expression on T cells and lower expression on CD19+CD45+ B lymphocyte. Background staining (dashed curve) and surface AChE-R staining (bold curve). Insert: B cells were defined by their high expression of the pan-B marker CD19 (y-axis) and CD45 (x-axis). T cells were labeled with the pan-T marker CD3 together with CD45.

FIG. 6B: Surface AChE-R contents on lymphocyte sub-populations. An average of ten samples from each source of cells were used. Shown are mean percent values of cells expressing surface AChE-R, and the mean fluorescent intensity (MFI)±standard error of the mean. Significant differences values (t-test, $p<0.05$) are marked by an asterisk.

Abbreviations: C, cord blood; A, adult peripheral blood; P, post-delivery peripheral blood.

Abbreviations: Ce. co., cell count; fluor. U.; fluorescence units; pos., positive.

FIG. 7A-7E: Spatiotemporal shifts in embryonic AChE mRNAs within blood cell forming tissues.

FIG. 7A: Schematic of the human ACHE gene and its alternative mRNAs. The core of human AChE is encoded by three exons, and parts of additional regions encode the variant-specific C-terminal sequences. Transcription begins at E1, and E2 encodes a leader sequence that does not appear in any mature protein. In addition to a proximal promoter (red line adjacent to E1), a distal enhancer region (the other red line) is rich in potential regulatory sequences, some of which are shown as wedges.

FIG. 7B: Sagital section of a human embryo showing the hematopoietic organs—AGM (aorta-gonad-mesonephros, blue), LIV (liver; green), SPL (spleen; red), and BM (bone marrow; brown).

FIG. 7C: Scheme of gestational shifts in hematopoietic processes shows the relative levels of blood cell formation in the various hematopoietic organs throughout human gestation [Tavassoli, M. (1991) *Blood Cells* 17:269-281]. Ages for which in situ hybridization was performed are marked by gray columns.

FIG. 7D: Representative in situ hybridization in liver micrographs from human fetuses at the noted gestational ages. Selective probes for each of the alternative human AChE mRNA transcripts showed increased expression (red precipitate) of AChE-R mRNA at 16 weeks of gestation, at the same time when the liver changes from erythropoiesis to myelopoiesis.

FIG. 7E: Line colors representing (as in 7C) spatiotemporal changes in labeling intensity and standard error of the mean (SEM) for each probe and organ, expressed as percentage of red pixels in each slide [Grisaru (1999a) id ibid.]. Note that AChE mRNA expression increases parallel to active hematopoiesis in the examined organs (N=4-6 tests for each organ in each gestational age). mRNA peaks in the liver at 16 weeks, coinciding with a shift in fetal liver hematopoiesis, from erythropoiesis to myelopoiesis [Porcellini, A. et al. (1983) *Int. J. Cell Cloning*, 1: 92-104].

Abbreviations: G. a., gestational age; wk., weeks; r.p., red pixels.

FIGS. 8A-8G: Parturition-induced transient increases in cortisol and sustained increases in catalytically active plasma AChE- and AChE-R-positive granulocytes.

FIG. 8A: Serum cortisol levels were higher than normal in the pre- and intra-partum periods. Note the significant decrease post-partum.

FIG. 8B: Plasma catalytic activity of AChE shows stable increase during the entire peri-partum period.

FIG. 8C: Alternative splicing of the ACHE gene.

FIG. 8D: Cortisol levels in patients during parturition (N=20) were significantly higher than in controls (Cont N=48), reflecting the stress of parturition.

FIG. 8E: Cortisol levels show direct correlation to increases in white blood cells (WBC) during parturition.

FIG. 8F: Increase in serum cortisol.

FIG. 8G: Intra-partum AChE-R-positive granulocytes (Gran) increases as a function of the increase in serum cortisol.

Asterisks indicate statistical significance.

Abbreviations: cort., cortisol; act., activity; ce., cells.

FIG. 9A-9D: Peri-partum blood profile.

Shown are blood profile changes in patients before (PRE), during (INTRA) and following (POST) delivery. Dotted areas represent normal blood count ranges.

Figures 9A, 9B:
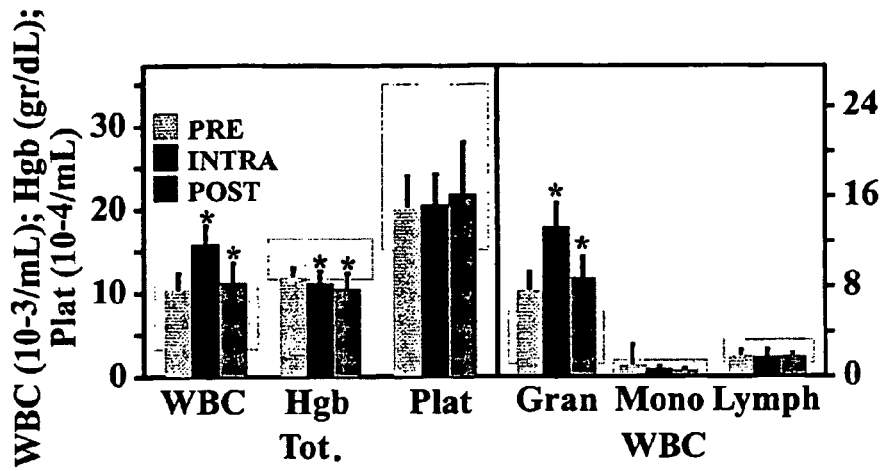

FIG. 9A: WBC counts increase during labor (above normal range) and decrease post-partum, albeit remaining above normal. Hemoglobin levels (Hgb) decrease below normal range during and after delivery. Platelet (Plat) counts remain stable (at normal range) during the entire period.

FIG. 9B: Sustained leukocytosis correlates with elevation in granulocyte (Gran), but not monocyte (Mono) or lymphocyte (Lymph) counts which remained within normal range. Asterisks indicate statistically significant differences (N=16 patients).

Figure 9C:
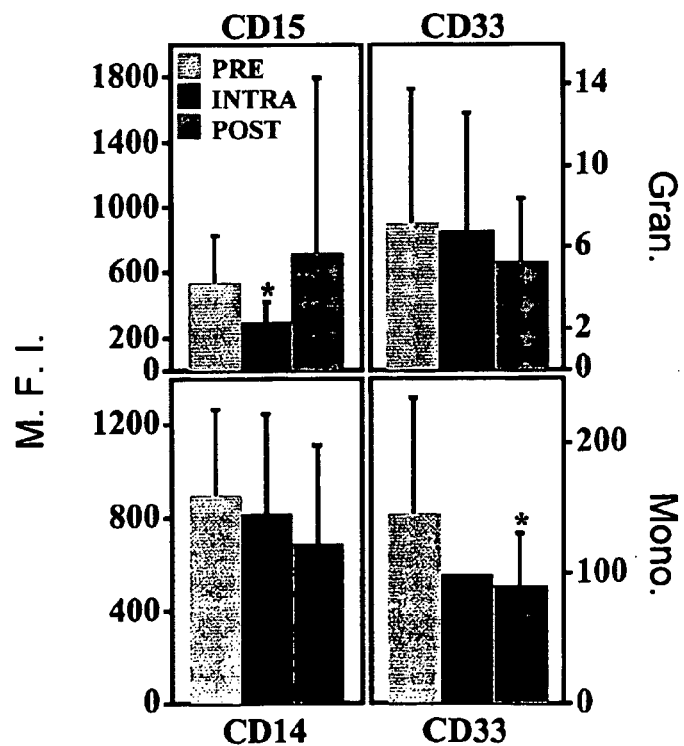

FIG. 9C: Shown are CD15 and CD33 labeling on AChE-R positive granulocytes (upper panel) and CD14 and CD33 in monocytes (lower panel). Note decreases in CD 15 expression in intra-partum granulocytes and decreases in post-partum monocytes.

Figure 9D:
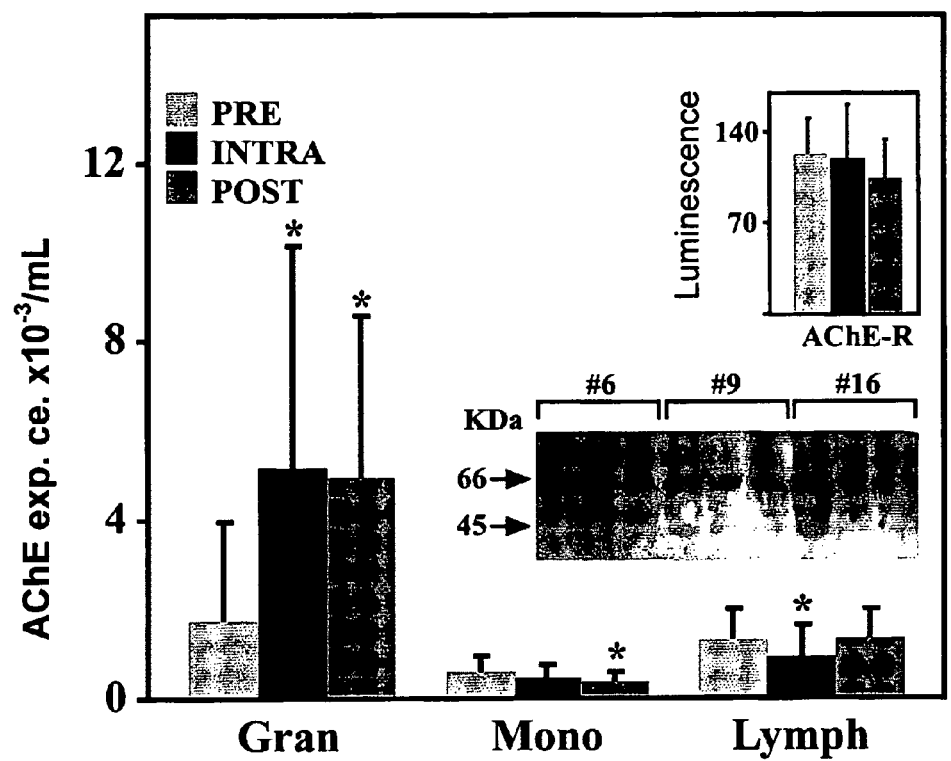

FIG. 9D: The significant intra- and post-partum increase in AChE-R positive granulocytes, but not monocytes or lymphocytes, may explain the stable serum activity. Immunoblots (insert) of serum proteins from 3 patients demonstrate AChE-R presence. Luminiscence analysis of the AChE-R blot (upper insert) shows stable presence of AChE-R in the serum of women during the peri-partum period.

Abbreviations: Tot., total; MFI, Mean Fluorescence Intensity; Gran., granulocytes; momo., monocytes; exp., expression; ce., cells.

Figure 10:
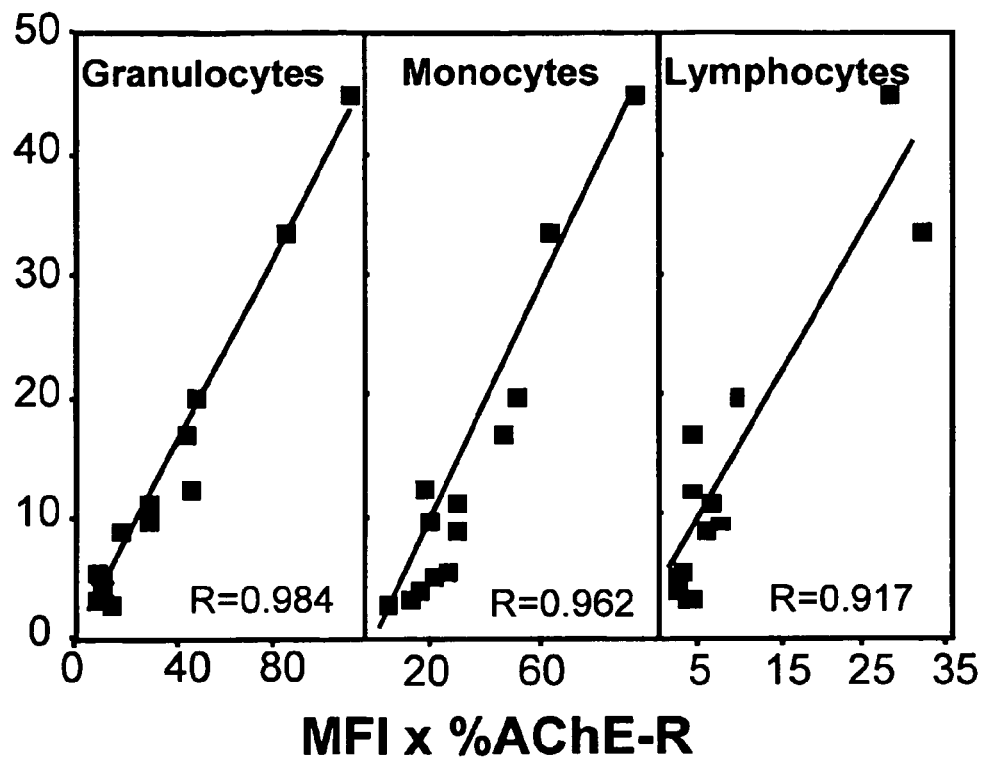

FIG. 10: Stress induced AChE-R in white blood cells correlates with presence of active AChE-R in the plasma.

The figure shows a direct correlation between AChE-R expression in all types of white blood cells (granulocytes, monocytes and lymphocytes) and its activity in the plasma of postpartum mothers.

FIG. 11A-11E: $ARP_{26}$ operates as an inducer of ACHE gene expression and potentiates myeloid expansion in vivo.

Figure 11A:
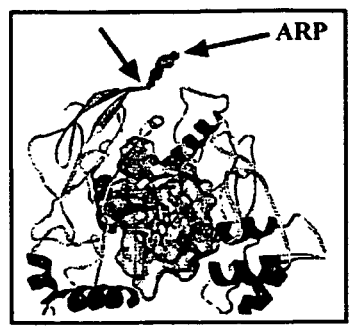

FIG. 11A: Structure of the AChE-R isoform with the stress induced cleavage (arrow) of the C-terminus (ARP).

Figure 11B:
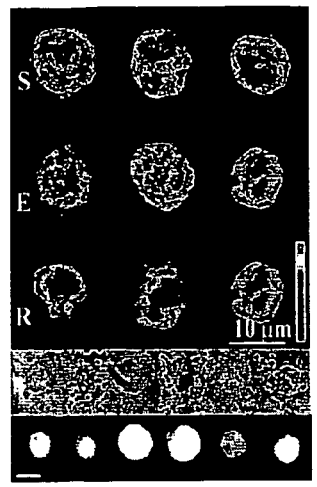

FIG. 11B: Human cord blood CD34$^+$ cells treated for 24 hours with the noted doses of $ARP_{26}$ as the sole growth factor were subjected to in situ hybridization with probes selective for each of the noted AChE mRNA splice variants. Shown are representative micrographs of the cells. Lower panels: Cytochemical staining for AChE catalytic activity in the presence of $10^{-5}$ M iso-OMPA, a selective inhibitor of butyrylcholinesterase (center) and nuclear staining with DAPI (bottom). Note intensified brown precipitates of AChE reaction product, mainly under 2 nM of $ARP_{26}$.

Figure 11C:
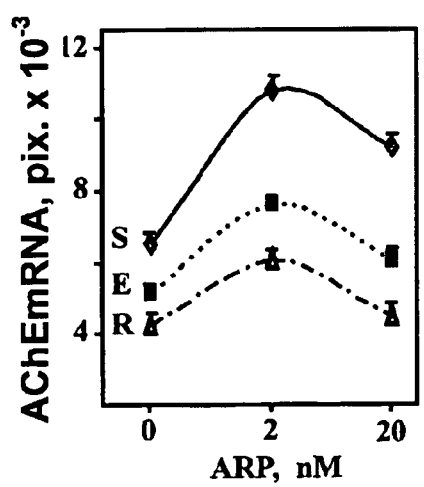

FIG. 11C: Average labeling densities for 10-20 individual cells. Note the concomitant increases in all transcripts, peaking at 2 nM ARP, and the limited variance between cells.

Figure 11D:
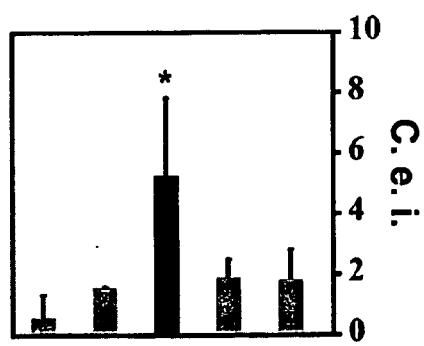
Figure 11E:
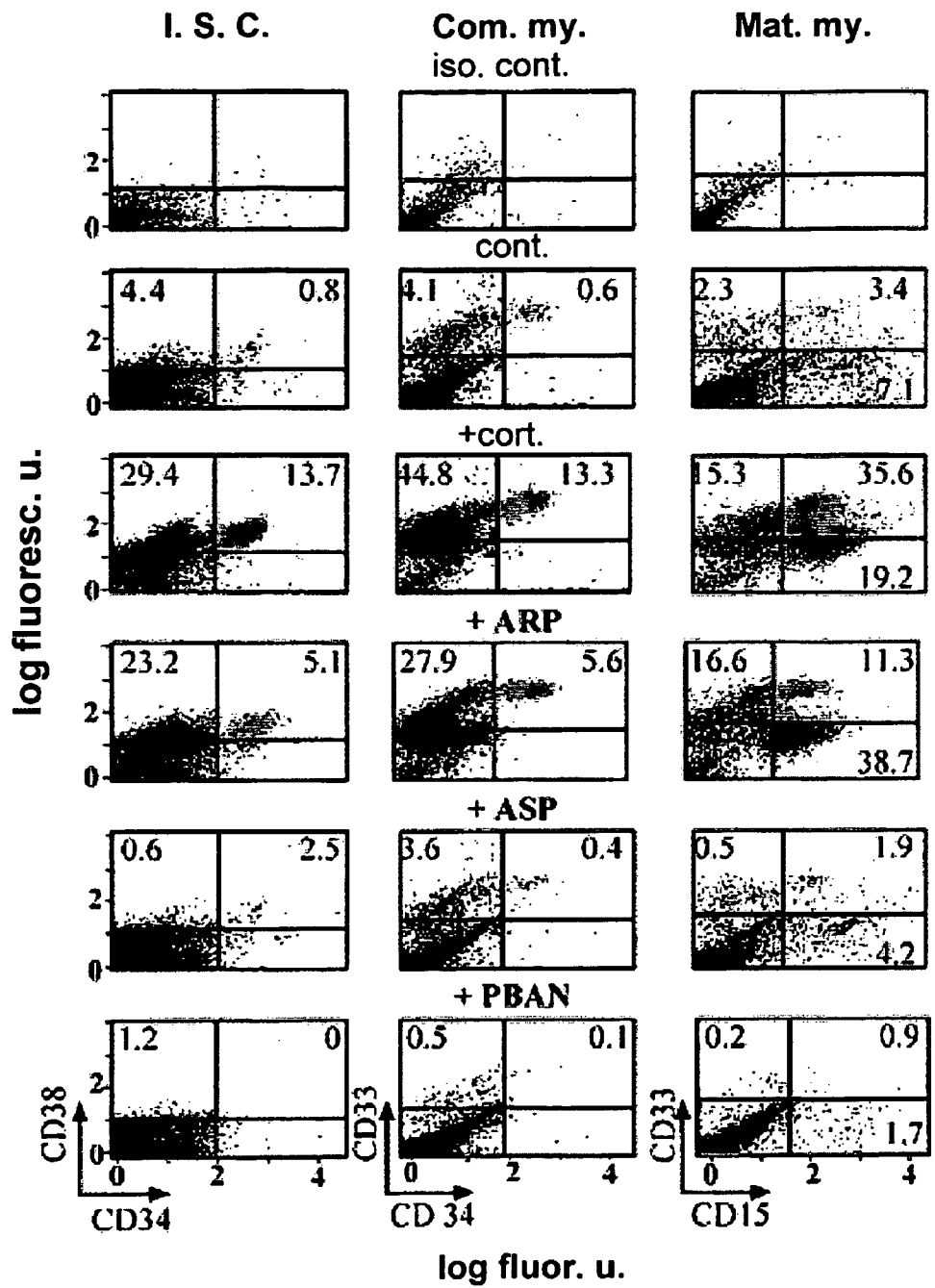

FIG. 11D-11E: Flow cytometric analysis of CD34+-derived hematopoietic cells after 2 weeks in liquid culture. Incubation with $ARP_{26}$, but not with cortisol, $ASP_{40}$ or PBAN, increased the total number of cells. FIG. 11D: The expansion index (the number of viable cells/ml culture divided by the number of seeded cells) was considerably higher following incubation with $ARP_{26}$. FIG. 11E: The percentage of immature stem cells (left column), committed myeloid cells (middle column) and mature myeloid cells (right column) that developed in the presence of each supplement is indicated by numbers on the relevant dot plots. Unlabeled cells appear as black dots and double-labeled ones as green dots. Note similar patterns under the influence of cortisol and $ARP_{26}$, but not of the $ASP_{40}$ and PBAN negative control peptides.

Abbreviations: pix., pixels; c.e.i., cell expansion index; treat., treatment; I.S.C., immature stem cells; com. My., committed myeloid; mat. my., mature myeloid; fluoresce., fluorescence; u., units; cont., control; iso., isotype; cort., cortisol.

Figure 12A:
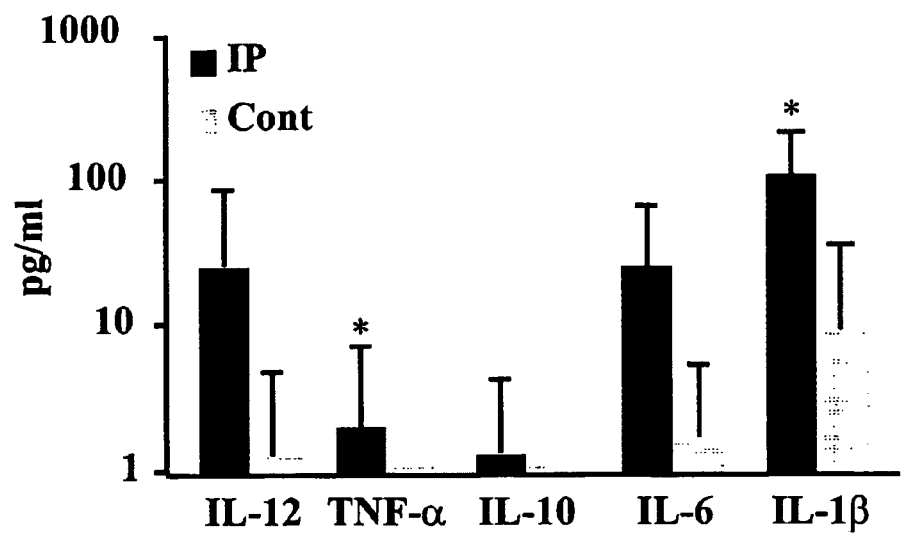
Figure 12B:
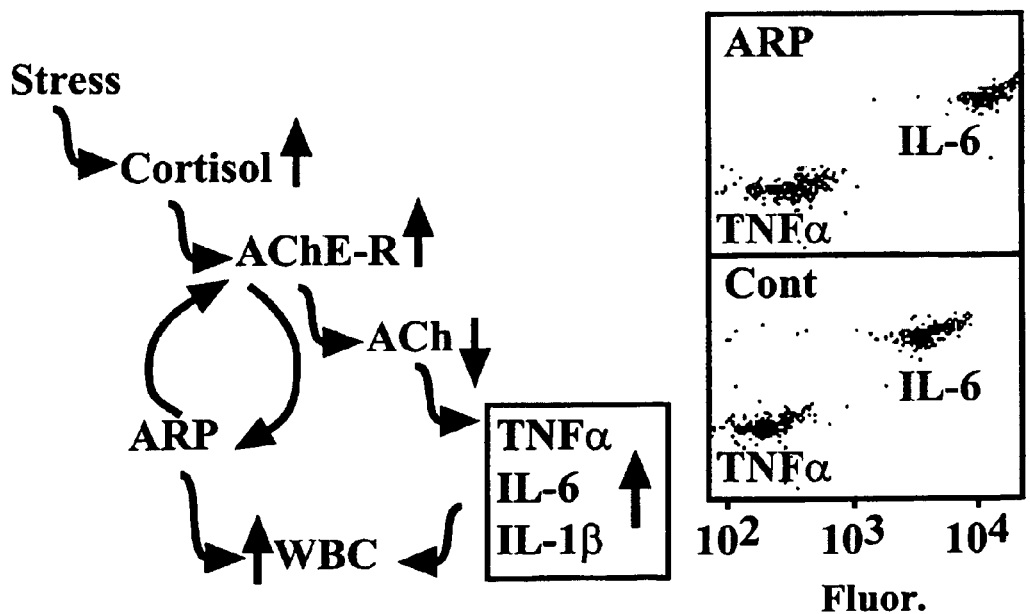
Figure 12C:
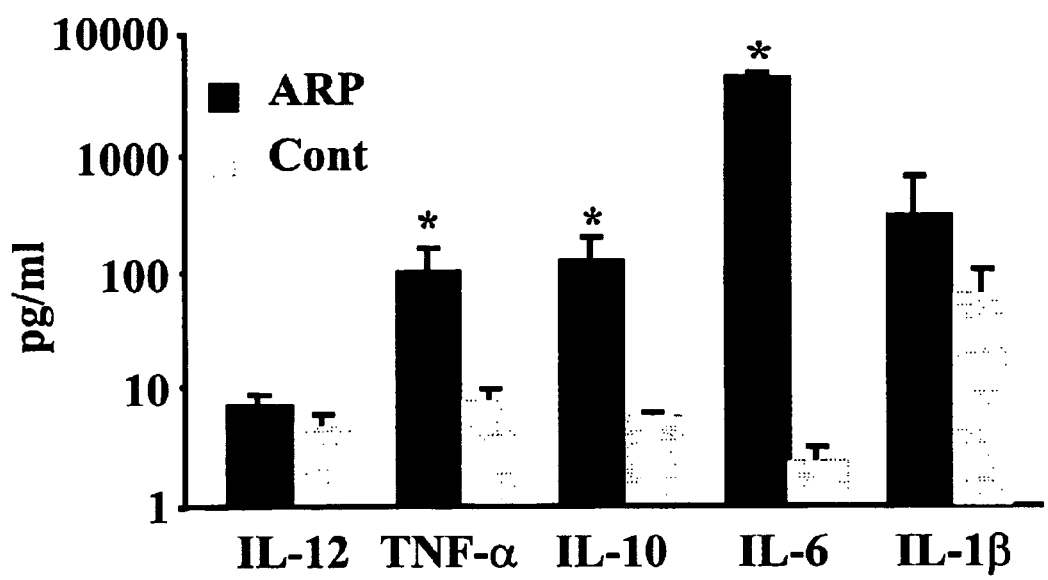

FIG. 12A-12C: ARP induces cytokine elevation in WBC.

FIG. 12A: Plasma cytokine levels in intra-partum patients and matched controls, measured by a particle-based flow cytometry immunoassay (human inflammation cytometric bead array kit, BD Bioscience, Palo Alto, Calif.). Note elevation of IL-12, IL-6, and IL-1β under post-partum conditions (N=15 in each group).

FIG. 12B: The proposed concept involves stress-induced elevation of plasma cortisol, which promotes AChE-R overproduction in peripheral mononuclear cells. C-terminal cleavage of AChE-R yields ARP, which amplifies AChE-R overproduction independently of cortisol. Accumulation of AChE-R potentiates ACh hydrolysis, alleviating the nicotinic α7 AChE control over pro-inflammatory cytokine production and resulting in elevated TNFα and IL-6 (fluorescence intensity). Inset: Fluorescence profiles of IL-6 and TNFα-positive cells from ARP-treated (top) and control culture (bottom).

FIG. 12C: To test causal relationship between elevated AChE-R and cytokine plasma levels adult peripheral mononuclear cells (N=3) were incubated for 24 hours with or without 2 nM $ARP_{26}$. Note significant increases in IL-6, IL-10 and TNFα levels, but not the anti-inflammatory cytokine IL-12, following $ARP_{26}$ treatment. Asterisks denote statistically significant differences compared to control.

Abbreviations: Fluor., fluorescence.

Figure 13A:
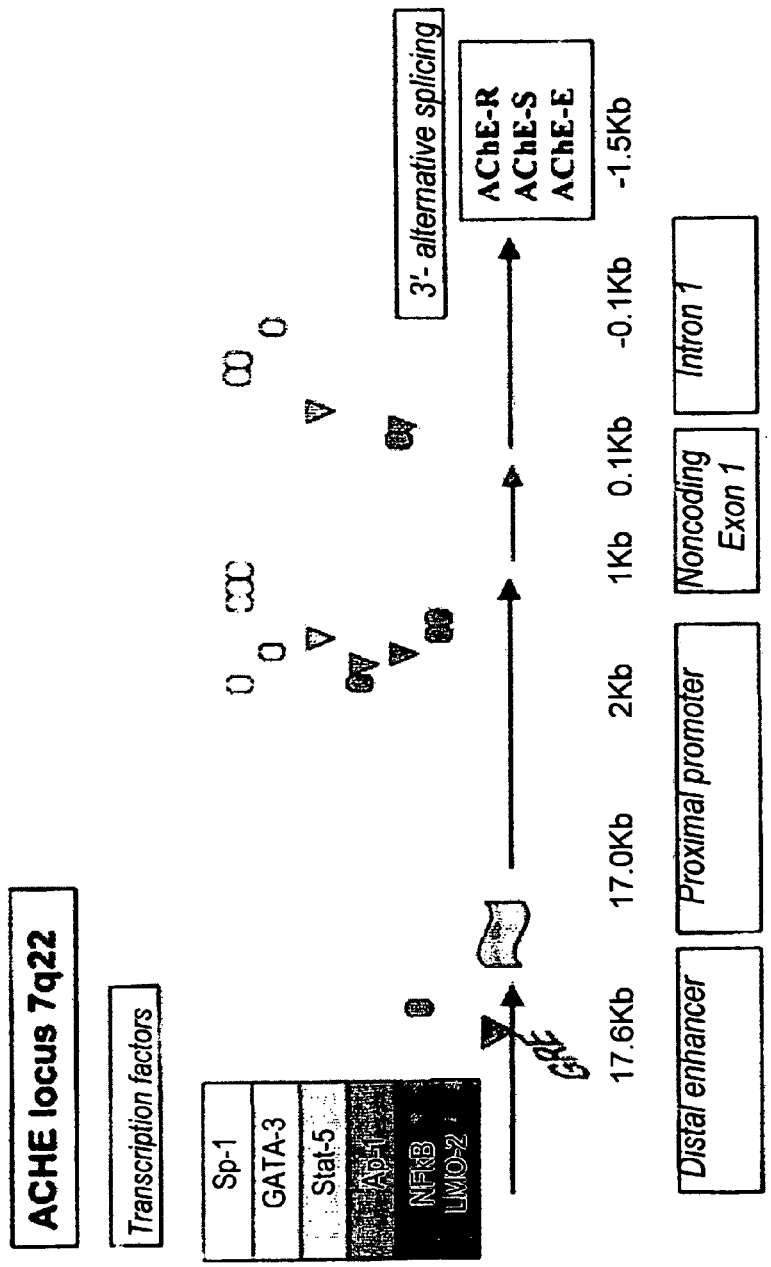
Figure 13B:
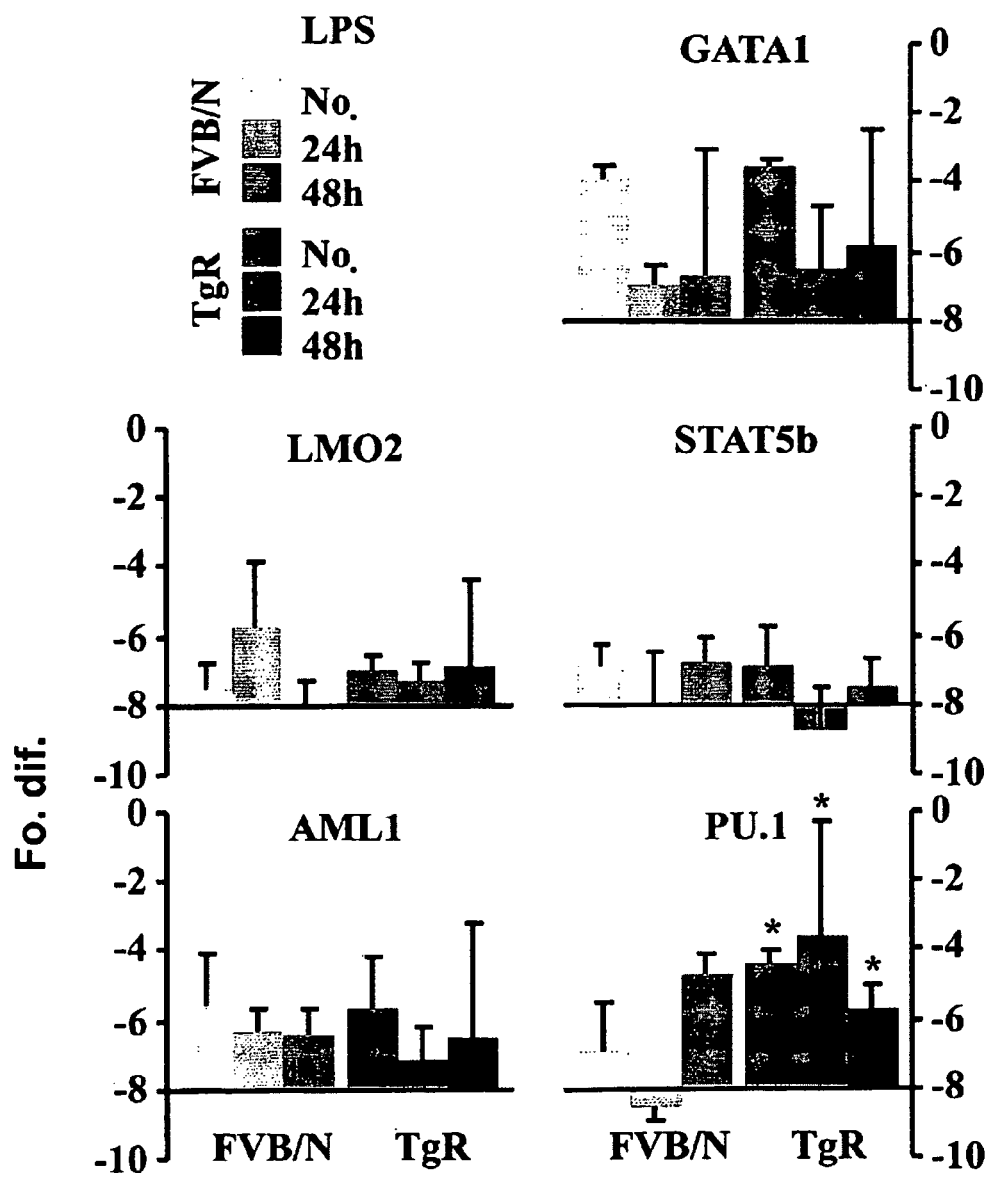

FIG. 13A-13B: Expression pattern of transcription factors pivotal for hematopoiesis following inflammatory stress.

FIG. 13A: Relevant hematopoiesis related transcription factors binding sites on the ACHE promoter.

FIG. 13B: Shown are expression of transcription factors pivotal for hematopoiesis in bone marrow extracts from FVB/N (dashed line) and TgR mice (solid line) (n=25), at different time points post LPS injection. Asterisks denote significant differences and results are presented as mean+SD ($p<0.02$, n=10), by real time RT-PCR. levels of transcription factors levels in While the response pattern to LPS of LMO2, GATA1, RUNX1 and STAT5 was similar in both FVB/N and TgR mice, PU.1 levels decreased significantly in FVB/N but not in TGR mice bone marrow, in response to LPS. At 72 h post LPS injection, PU.1 levels recovered and even reached higher than base-line values in FVB/N mice, but showed some decrease in TgR mice.

Abbreviations: No., none; Fo. Dif., fold difference.

Figure 14A:
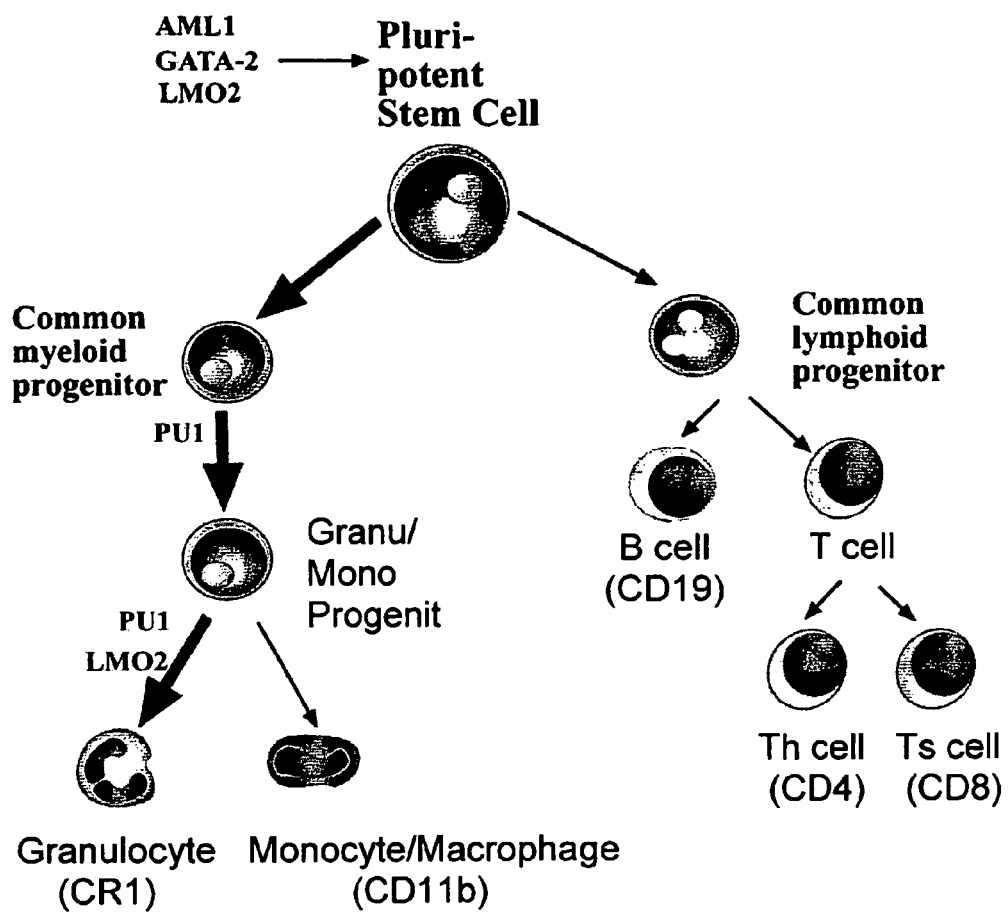
Figure 14B:
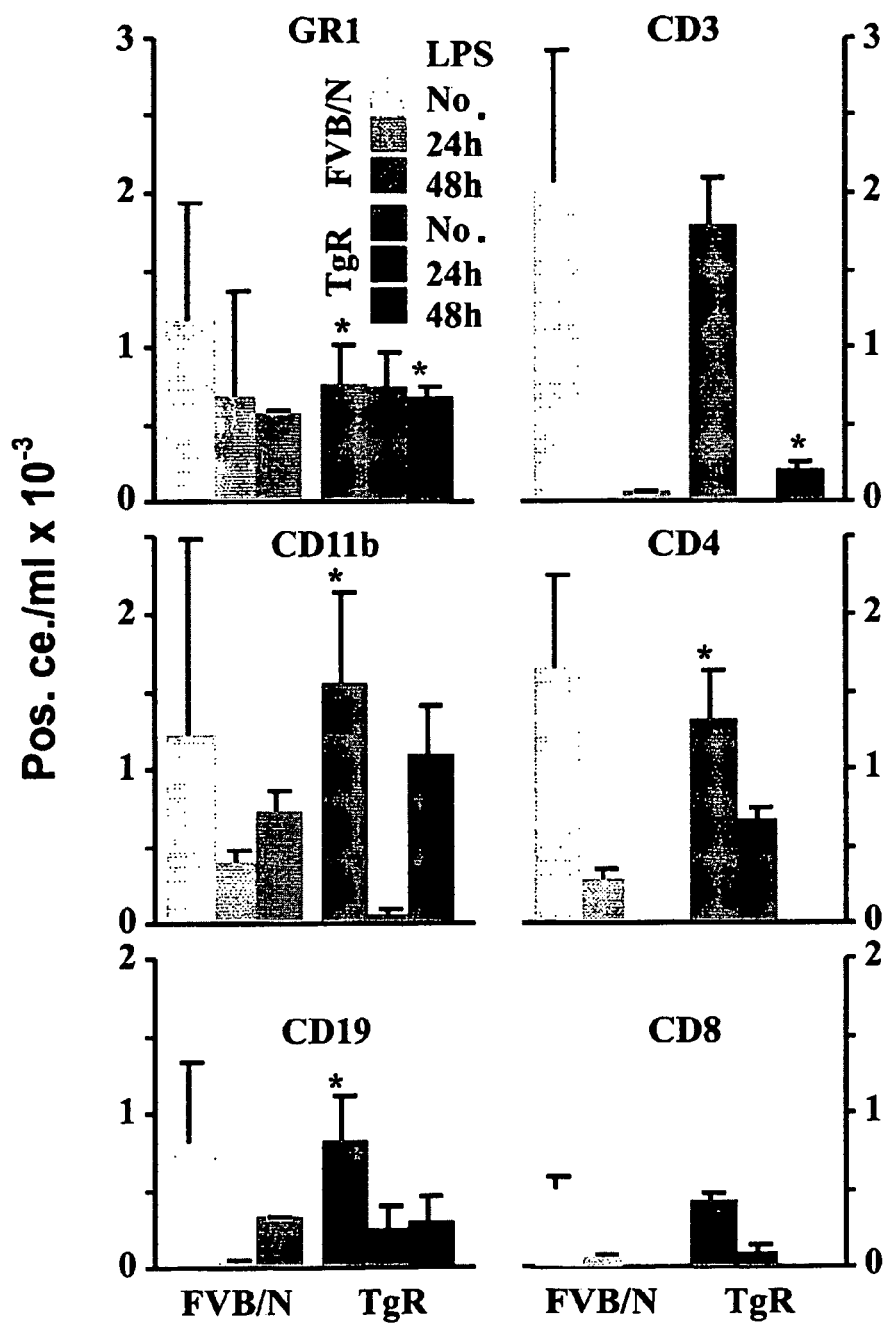

FIG. 14A-14B: Rapid post-LPS hematopoietic recovery in TgR mice.

FIG. 14A: Immunophenotyping of the hematopoietic progenitors and the relevant transcription factors during the differentiation.

FIG. 14B: Shown are WBC counts in FVB/N (dashed line) and TgR mice (solid line) (n=25). Results of morphological examination of TgR and FVB/N mice peripheral blood smears, at different time points post LPS injection.

Asterisks denote significant differences and results are presented as mean+SD ($p<0.02$, n=10).

Peripheral blood immunophenotyping revealed that while FVB/N mice had a significant decrease in GR1+ (granulocyte) cells, in response to LPS injection, the number of GR1+ remained unchanged in TgR mice and was significantly higher than FVB/N by 72 h post LPS injection. Both FVB/N and TgR mice had decreased CD11b+ (monocytic) cell counts 24 h post LPS injection, although the decrease was steeper in TgR as compared to FVB/N mice. CD11b+ cell counts recovered almost completely by 72 h post LPS injection in both FVB/N and TgR mice, TgR mice attaining higher Cd11b+ counts, although not reaching a statistically significant value.

Asterisks denote significant differences and results are presented as mean+SD.

Abbreviations: pos. ce., positive cells; no., none.

Figure 15A:
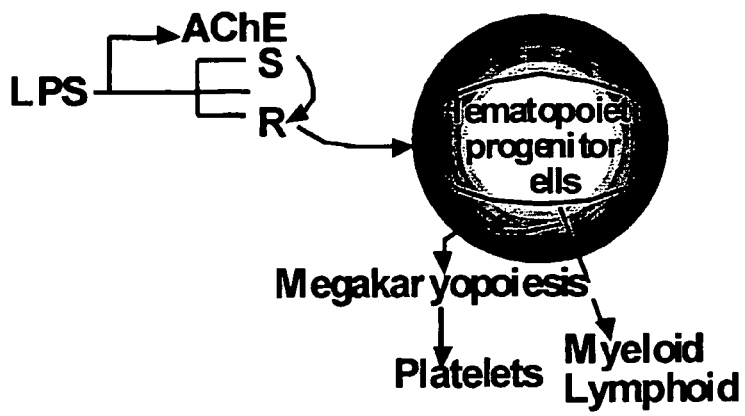
Figure 15B:
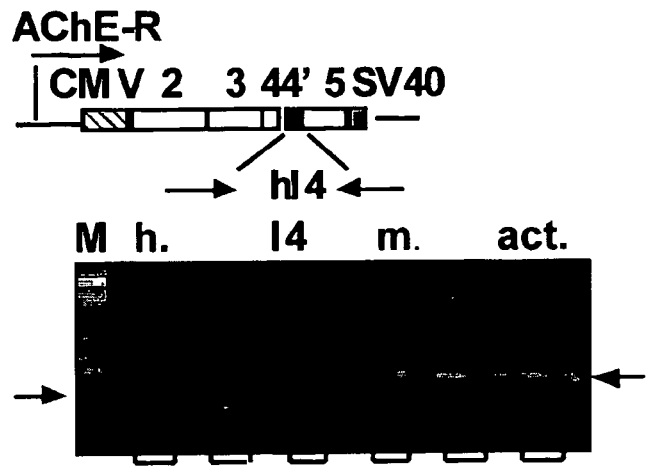
Figure 15C:
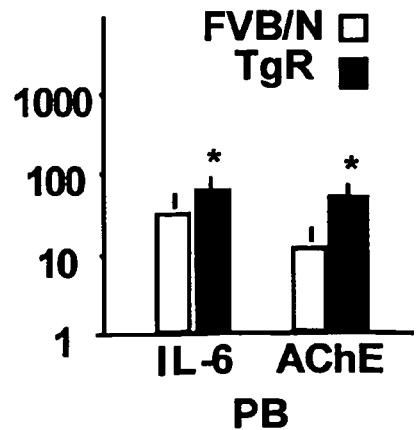

FIG. 15A-15C: Transgene facilitation of hematopoietic regulators.

FIG. 15A: Schematic of the proposed mechanism, which shows how a stress-induced switch from production of AChE-S to the -R variant results in hematopoietic progenitor cell expansion towards the megakaryocyte lineage and increased platelet counts.

FIG. 15B: Human (h) AChE-R DNA construct inserted into the FVB/N mouse genome for generating the TgR transgenic mice. hAChE-R cDNA-derived 100 base pair product was successfully amplified in bone marrow DNA of TgR ($5^{th}$ and $6^{th}$ lanes, after the marker—M), but not TgS or FVB/N mice (n=12, left arrow). A mouse actin product (130 base pair, right arrow) appeared in all 3 tested lines, FVB/N, TgR and TgS.

FIG. 15C: Levels of the pro-inflammatory cytokine IL-6 (pg/ml) and the AChE catalytic activity (activity per minute per gram of protein) in PB of TgR and FVB/N mice. Asterisks denote significant differences and results are presented as mean±SD ($p<0.01$, n=10).

Abbreviations: h., human; m. act., mouse actin; PB, peripheral blood.

FIG. 16A-16D: Shorter post-LPS hematopoietic recovery in TgR mice.

Graphs show $RBC \times 10^9$ (FIG. 16A), $WBC \times 10^6$ (FIG. 16B) and platelet ($Plts \times 10^6$) (FIG. 16C) counts per ml of FVB/N (dashed line) and TgR mice (solid line) (n=25) peripheral blood.

FIG. 16D: Results of morphological examination of TgR and FVB/N mice peripheral blood smears, at different time points post LPS injection as indicated. Asterisks denote significant differences and results are presented as mean±SD of $WBC \times 10^6$ per ml of blood ($p<0.02$, n=10).

Abbreviations: T. po., time post; gran., granulocytes; mono., monocytes; lymph., lymphocytes.

Figures 17A, 17B:
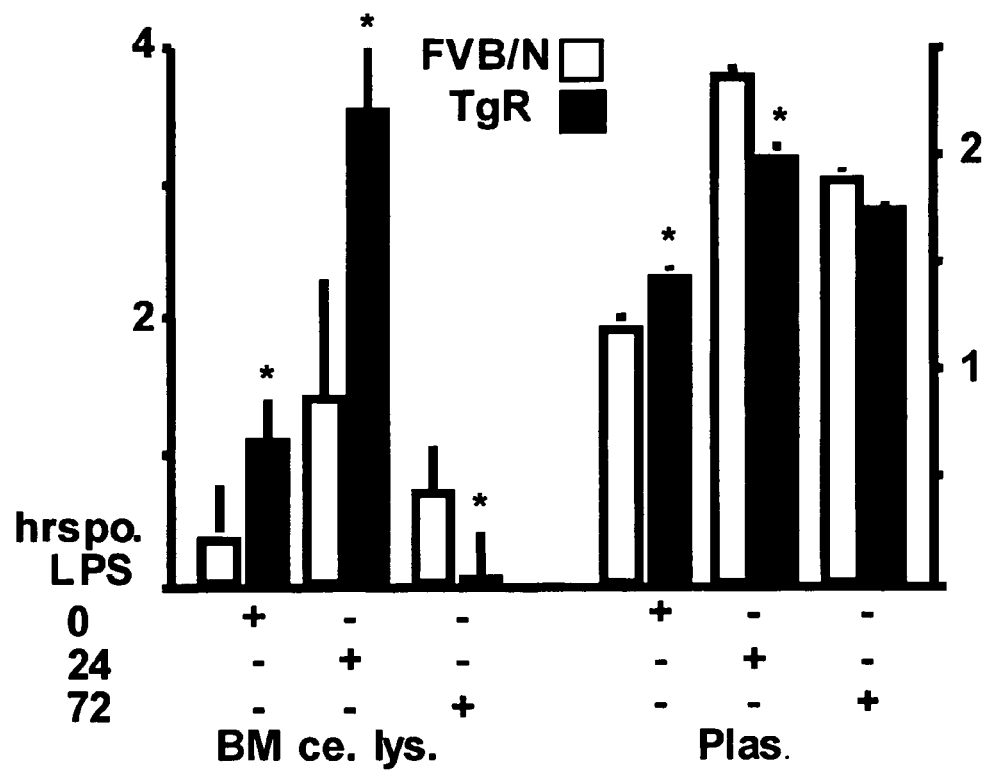

FIG. 17A-17B: Changes in TPO levels in response to LPS injection.

Thrombopoietin (TPO) levels were measured in bone marrow (BM) cell lysates (FIG. 17A) and plasma (FIG. 17B) from TgR and FVB/N mice.

Asterisks denote significantly different values. Results are presented as mean±SD ($p<0.04$, n=10).

Abbreviations: po., post; ce. ly., cell lysates; plas., plasma.

Figures 18A, 18B, 18C:
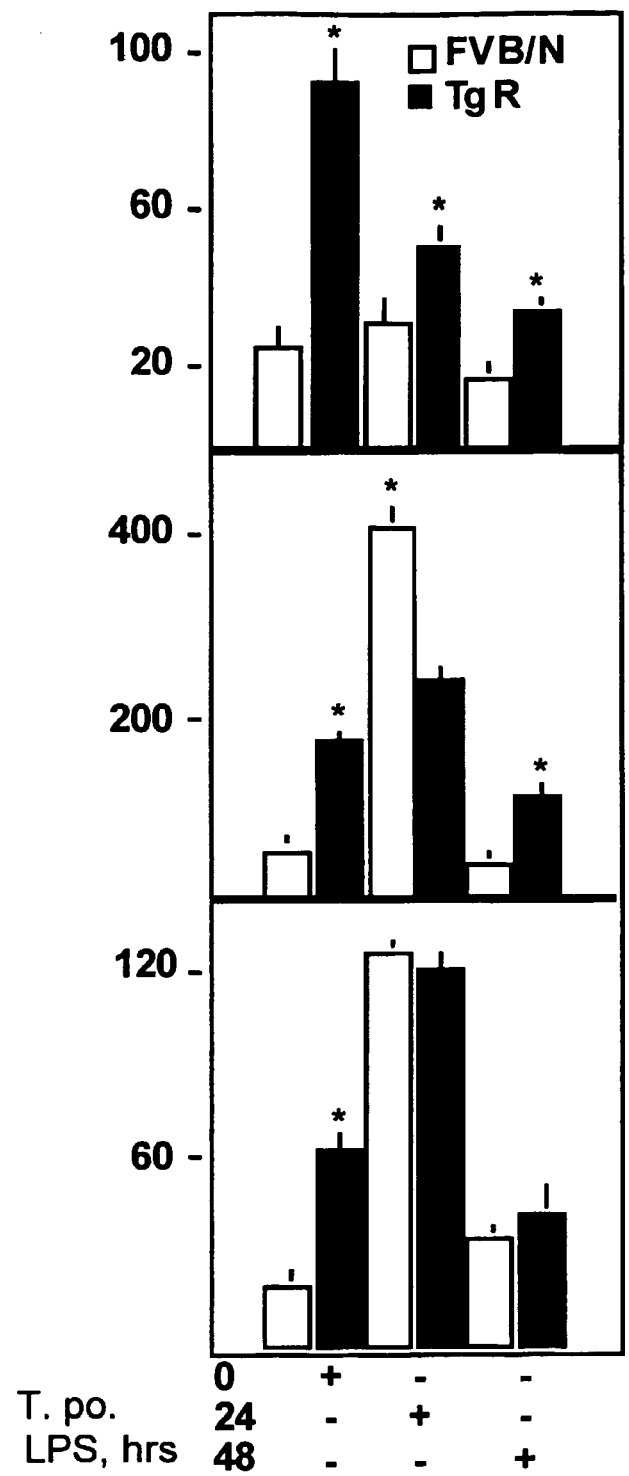

FIG. 18A-18C: Facilitated progenitor cells potential in TgR mice.

Committed colony-forming units of megakaryocyte (CFU-Mk, FIG. 18A), granulocytic/monocytic (CFU-GM, FIG. 18B) and multi-potential (CFU-GEMM, FIG. 18C) progenitors were quantified in a semisolid colony formation assay. Asterisks denote significantly different values. Assays were set up in triplicates from bone marrow preparations from 4 separate mice per time point. Values represent mean±SD.

Abbreviations: T. po., time post.

FIG. 19A-19F: AChE-R, RACK1 and PKCε expression in megakaryocytes.

Bone marrow smears were stained with May-Grünwald (FIG. 19A) and specific antibodies to detect AChE-R (FIG. 19B), RACK1 (FIG. 19C) and PKCε (FIG. 19D). The ax symbol represents "anti", meaning the antibody against that specific protein was used in the respective staining.

FIG. 19E: Illustration of the putative interaction between the three proteins.

FIG. 19F: Population distributions of Mk labeling intensities for AChE-R, RACK1 and PKCε. White bars represent FVB/N and grey, TgR mice BM labeling intensities. Note the shift to the right, indicating increased levels of these 3 proteins in Mks from TgR as compared with FVB/N mice. n=50 cells per labeling experiment.

Abbreviations: Hist., histochemistry; ce., cells.

Figures 20A, 20B:
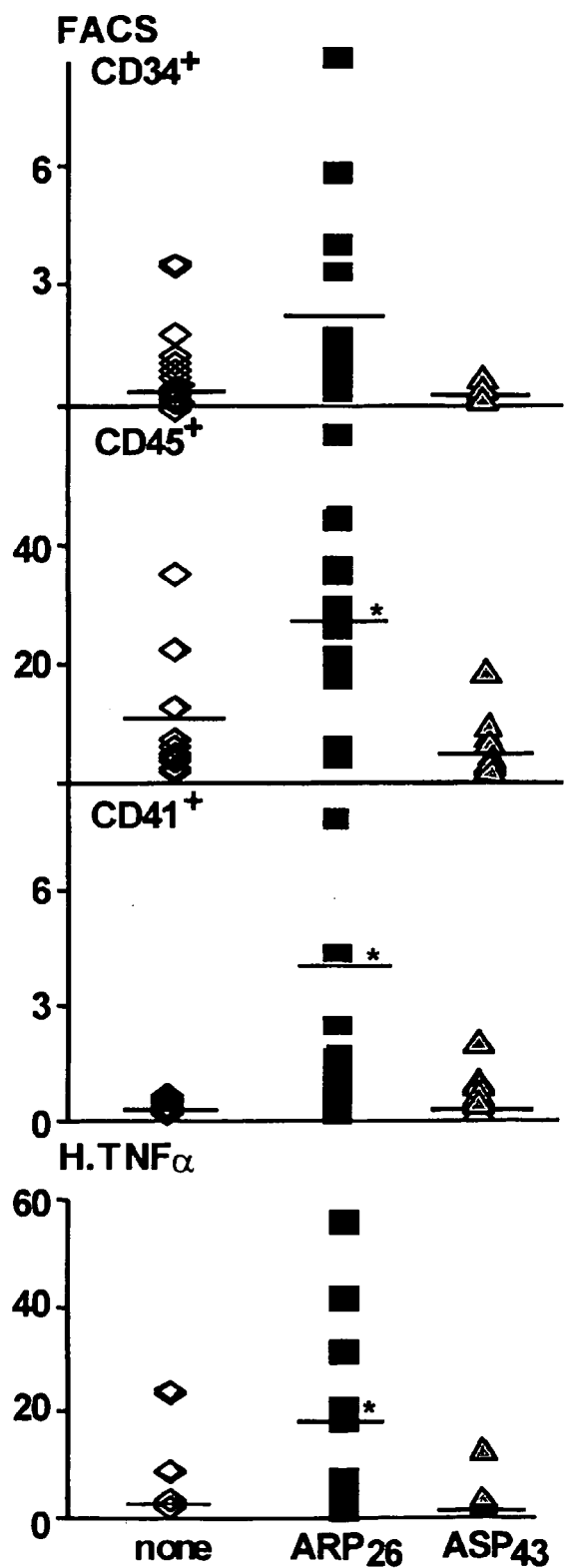

FIG. 20A-20B: Enhanced human cell engraftment with $ARP_{26}$.

100,000 human CB $CD34^+$ cells were injected into the tail vein of pre-irradiated NOD/SCID mice with no priming of cells (none, white diamond symbol), or following priming of cells with ARP$_{26}$ for 2-4 hours and injection with human ARP$_{26}$ (black square symbol) or ASP$_{40}$ (gray triangle symbol). Bone marrow was harvested 6 weeks post-transplantation.

FIG. 20A: CD34$^+$, CD45$^+$ and CD41$^+$ human cells were detected using flow cytometry and monoclonal antibodies, n=12, 16 and 8 mice, respectively.

FIG. 20B: Quantitative real time PCR using human TNFα as the probe to detect human DNA in the mouse bone marrow. Sensitivity limit was 10%. n=12, 16 and 8 mice respectively. Asterisks denote significant differences. Lines represent mean values.

Figure 21A:
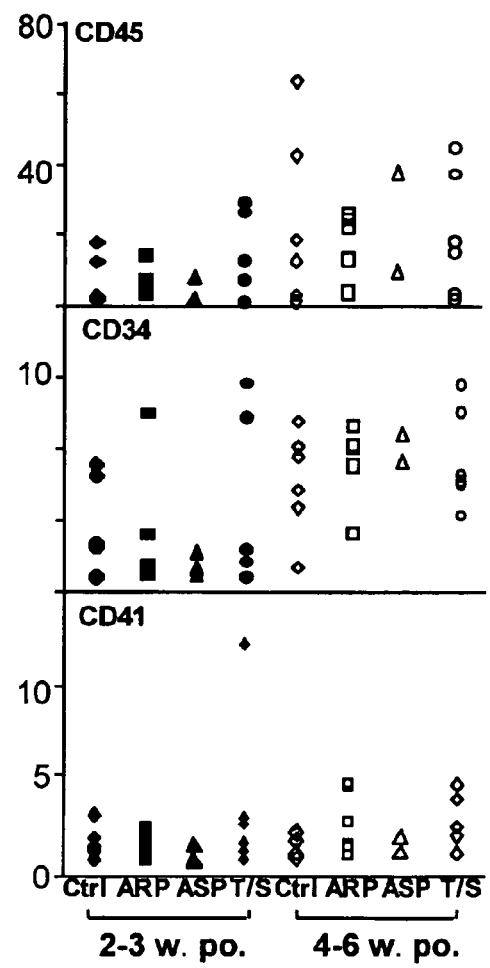
Figure 21B:
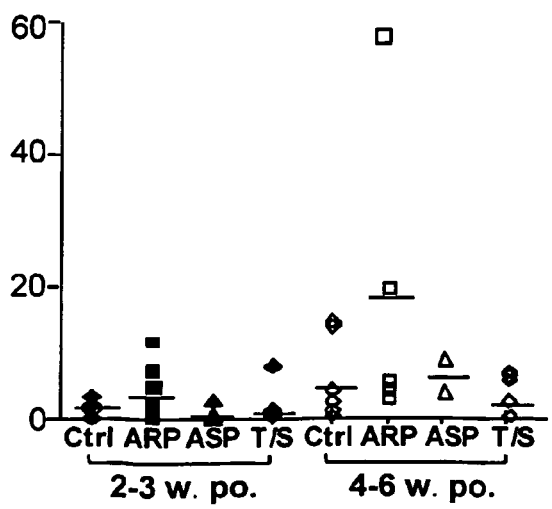

FIG. 21A-21B: Pre-cultured CD34$^+$ cells expanded with ARP$_{26}$ and improve platelet counts.

FIG. 21A: 100,000 human CD34+ cells were injected together with 1-200,000 CD34+ cells cultured for 10 days with no supplement (control), 2 nM ARP$_{26}$, 2 nM ASP$_{40}$ or human TPO/SCF (T/S). Antibodies to human CD45$^+$, CD34$^+$ and CD41$^+$ were used to quantify engraftment in BM (n=6).

FIG. 21B: Human platelets per mL of mouse blood were quantified using anti CD41, specific for human platelets. The mean differences between groups were large (denoted by lines). n=6.

Abbreviations: ctrl., control; T/S, TPO/SCF; po., post; wk., weeks; BM, bone marrow; PB, peripheral blood.

DETAILED DESCRIPTION OF THE INVENTION

The inventors originally described the ARP peptide as a peptide capable of inducing stem cell survival and expansion. In addition, ARP was shown to be capable of promoting myeloid and megakaryocytic differentiation [IL 130224, Inventors' co-pending US Patent Application 2003-0036632, Grisaru (2001) id ibid.].

In the present invention, the inventors demonstrate that overproduction and C-terminal cleavage of the stress-induced AChE-R isoform induced granulocytosis.

Effective growth and expansion of any defined hematopoietic cell population involve three milestones: the first, survival of stem cells, the second, proliferation of lineage-committed progenitor cells, and the third, expansion and maturation of terminally differentiated cells. The expansion of terminally-differentiated functionally-specific progeny requires sufficient progenitor proliferation prior to maturation, which depends on the size of the stem cell pool. There are growth factors or cytokines that function exclusively on each one of the levels mentioned above. For example, the stem cell factor (SCF) protects stem cells from apoptosis and supports their survival. Alone SCF does not cause the proliferation of stem or progenitor cells. Most of the clinically used hematopoietic cytokines drive proliferation of lineage committed progenitors such as G-CSF, GM-CSF, erythropoietin and thrombopoietin, and work in synergy with SCF, in vitro. The ideal growth factor would be a molecule capable of maintaining the survival of stem cells and with activity for the stimulation of committed progenitor proliferation of at least one or more lineage, while also being capable of deriving terminal differentiation. The results described in the present invention define ARP as such a growth and differentiation factor, being able to support survival of hematopoietic stem cells, as previously described [IL 130224, Inventors' co-pending US Patent Application 2003-0036632, Grisaru (2001) id ibid.], while driving proliferation of myeloid cells and inducing their terminal differentiation, specifically of the granulocytic lineage, and particularly neutrophils.

Thus, it is an object of the present invention to provide the use of an AChE-R-derived peptide as an inducer of granulocytopoiesis. Yet another object of the invention is to provide methods and compositions for the prevention and/or treatment of conditions leading to low white blood cell count in general, and particularly leucopenia, and more particularly neutropenia. In addition, such treatments may increase cytokine production in patients who have lost the capacity to induce the same in response to external stimuli. These include, for example, aged patients in whom cytokine levels cannot be induced anymore because their cholinergic control over such cell population is desensitized. These and other objects of the present invention will become apparent as the description proceeds.

The peptide used by the invention comprises the following amino acid sequence:

(SEQ ID NO: 1)
N'-GMQGPAGSGWEEGSGSPPGVTPLFSP-C'.

Said peptide is also denoted herein as ARP, or ARP$_{26}$.

The peptide of the invention may be isolated as a cleavage product of AChE-R. Alternatively, the peptide is a synthetic peptide, synthesized through the means of producing synthetic peptides known in the art.

Any functional derivatives and functional fragments of the above-defined peptide may be used in the invention. The terms functional derivatives and functional fragments used herein mean the peptide, or any fragment thereof, with any insertions, deletions, substitutions and modifications, which is capable of inducing granulocyte cell differentiation and/or cytokine production, particularly TPO and pro-inflammatory cytokines like TNFα, IL-6 and IL-1β.

Further, the peptide of the invention may be extended at the N-terminus and/or C-terminus with various identical or different amino acid residues. As an example for such extension, the peptide may be extended at the N-terminus and/or C-terminus thereof with identical or different amino acid residue/s which may be naturally occurring or synthetic amino acid residue/s. One example for a synthetic amino acid residue is D-alanine. An additional example for such an extension may be provided by peptides extended both at the N-terminus and/or C-terminus with a cysteine residue.

Another example may be the incorporation of an N-terminal lysyl-palmitoyl tail, the lysine serving as linker and the palmitic acid as a hydrophobic anchor.

In addition, the peptide may be extended by aromatic amino acid residue/s, which may be naturally occurring or synthetic amino acid residue/s. A preferred aromatic amino acid residue may be tryptophan. Alternatively, the peptide can be extended at the N-terminus and/or C-terminus thereof with amino acids present in corresponding positions of the amino acid sequence of the naturally occurring C-terminal region of AChE-R.

Nonetheless, according to the invention, the peptide to be used in the invention may be extended at the N-terminus and/or C-terminus thereof with various identical or different organic moieties which are not naturally occurring or synthetic amino acids. As an example for such extension, the peptide may be extended at the N-terminus and/or C-terminus thereof with an N-acetyl group.

The lack of structure of linear peptides renders them vulnerable to proteases in human serum and acts to reduce their affinity for target sites, because only few of the possible conformations may be active. Therefore, it is desirable to optimize the peptide structure, for example by creating different derivatives of the peptide of the invention. In order to improve peptide structure, the peptide of the invention can be coupled through its N-terminus to a lauryl-cysteine (LC) residue and/or through its C-terminus to a cysteine (C) residue.

The peptide of the invention, as well as derivatives thereof may be positively charged, negatively charged or neutral and may be in the form of a dimer, a multimer or in a constrained conformation. A constrained conformation can be attained by internal bridges, short-range cyclizations, extension or other chemical modification.

The inventors have demonstrated, in the following Examples, how peripheral cholinergic stress responses, in particular overproduction and C-terminal cleavage of the stress-induced AChE-R variant, resulted in long-lasting granulocytosis, likely independent of elevated cortisol levels.

The presence of a functional glucocorticoid response element in the upstream ACHE promoter [Grisaru et al. (2001) id ibid.], combined with the transient post-partum increase in serum cortisol [Mastorakos, G. and Ilias, I. (2000) Ann. NY Acad. Sci. 900: 95-106] could explain the initial transcriptional enhancement of ACHE gene expression in hematopoietic cells. However, the transient nature of cortisol elevation also implies that a different transcriptional enhancing signal (s) should extend this response after the first few hours. That $ARP_{26}$ by itself elevated ACHE gene expression in CD34+ progenitors provided a tentative explanation for this prolonged induction, suggesting that the overproduced cleavable AChE-R can regulate its own production. These results suggest that ARP may be used, in vivo and in vitro, for the induction of AChE-R expression, or for re-adjusting the ratio between AChE-S and AChE-R.

The dose-dependent pattern of this effect further indicates that either too high or too low concentrations of $ARP_{26}$ fail to induce AChE-R mRNA accumulation, suggesting strict dependence of the splice shift process on previously produced AChE-R amounts which, in turn, reflects splicing regulation of the pre-AChE mRNA transcript in hematopoietic cells. $ASP_{40}$, the C-terminal peptide of AChE-S (denoted by SEQ ID NO:2), failed to induce such effects (FIGS. 11D-11E), supporting the specificity of the effect of ARP on prolonged granulocytosis. Vis-à-Vis the results obtained in Example 12, ARP may be used to treat hematopoietic stem cells ex vivo, driving the cells to the granulocytic differentiation pathway.

In addition, the present findings demonstrate increased thrombopoiesis in response to the stress-induced AChE-R protein and attribute part of the thrombopoietic process to ARP, and to its interaction with the scaffold protein RACK1 and PKCε. This has allowed the inventors to extend the concept of what has been defined by others as "The inflammatory reflex" [Tracey (2002) id ibid.] to the realm of thrombopoiesis.

The effects exerted by AChE-R on the proliferation and maturation of granulocytes could be due to both the catalytic and the non-catalytic properties of AChE-R as well as to the function(s) of its cleavable C-terminal peptide, ARP. The stable AChE hydrolytic activity throughout the peri-partum period, together with the increased AChE-R content in granulocytes point to the possibility that granulocytes may be the source of soluble blood AChE. This idea is reinforced by the presence of AChE-R in the serum of peri-partum women (FIG. 9A-9B). At the catalytic level, AChE-R excess should lead to reduced ACh concentrations in the post-partum serum. This, in turn, would alleviate the control over macrophage production of pro-inflammatory cytokines, increasing the concentration of such cytokines and inducing further proliferative and cell activation signals [Borovikova, L. V. et al. (2000) Nature 405: 458-462; Tracey, K. J. (2002) Nature 420: 853-859; Wang, H. et al. (2003) Nature 421: 384-388]. The existence of nicotinic [Wang (2003) id ibid.] and muscarinic [Hellstrom-Lindahl, E., and Nordberg, A. (1996) J. Neuroimmunol. 68:139-144; Mita, Y. et al. (1996) Eur. J. Pharmacol. 297: 121-127]. ACh receptors on myeloid cells suggests reduced cholinergic input to those cells as well, when under stress. Others report no direct cholinergic effects on peripheral blood cells [Tracey (2002) id ibid.]. However, the current study shows such effects for $ARP_{26}$, thus adding AChE-R production following transient increases in cortisol, and the reduced anti-inflammatory action of ACh, as additional steps to the pathway leading to protracted post-stress granulocytosis.

At the non-catalytic level, the present findings suggest the induction of signal transduction processes by the C-terminal peptide cleaved from AChE-R, likely through its interaction with PKCβII and its scaffold protein RACK1 [Inventors' co-pending US Patent Application 2003-0036632]. The reported involvement of PKC signaling in myeloid cell activation [Bassini, A. et al. (1999) Blood 93: 1178-1188] potentially implicates this interaction in the maturation and/or activation of granulocytes in the post-partum blood.

Interestingly, the inventors have shown that, during human fetal development, AChE-R mRNA expression was observed only in the developing liver for a limited time window (FIG. 7). The transient increase in AChE-R mRNA paralleled the period of fetal liver myelopoiesis, supporting the notion that AChE-R is physiologically relevant for in vivo myelopoiesis.

The induced AChE-R excess (Example 7) might be perceived as an adaptive response, facilitating the production of pro-inflammatory cytokines to protect the body from post-partum conditions, such as infections. This assumption is further supported by the increased production of pro-inflammatory cytokines by mononuclear cells in the presence of the synthetic peptide $ARP_{26}$. The question emerges, therefore, which signal(s) terminates this granulocytosis response. Because of the circular nature of the proposed cascade process, it might be terminated either at the periphery or in the brain, highlighting the close inter-relationships characteristic of long-lasting mammalian stress responses [Kiecolt-Glaser, J. K. et al. (2003) Proc. Natl. Acad. Sci. USA 100: 9090-9095]. It is tempting to speculate that, similarly to what happens within the central nervous system, chronically elevated AChE induces a secondary feedback response of excess ACh production in the periphery [Erb, C. et al. (2001) J. Neurochem. 77: 638-646]. Re-balanced ACh levels can then suppress the production of pro-inflammatory cytokines in macrophages [Tracey (2002) id ibid.], terminating the granulocytosis process. IL-1β was shown to induce ACHE gene expression in phaeochromocytoma cells [Li, Y. et al. (2000) J. Neurosci. 20: 149-155], suggesting that reduced IL-1β levels could reciprocally decrease AChE-R (and, therefore, its cleavage product) levels back to normal, retrieving peripheral cholinergic homeostasis.

Thus, essentially, the ARP peptide may be used as an inducer of pro-inflammatory cytokines, particularly TNFα, IL-6 and IL-1β.

The development of transgenic mice overexpressing AChE-R allowed the inventors to further comprehend the cholinergic effect on the inflammatory response. The presence of AChE-R at high levels apparently does not affect the basal status of the hematopoietic system. However it serves as an enhancer to rapid recovery of the system following an inflammatory challenge.

At least two mechanisms, not necessarily mutually exclusive, could be implicated in that. One through the induction of pro-inflammatory cytokines, as mentioned above. Two through the induction of the putative oncogene Spi-1 (PU.1)

protein product, a hematopoietic-specific Ets factor essential for myeloid and lymphocyte development, which has also been implicated in LPS-induced signaling [Busslinger, M. (2004) *Ann. Rev. Immunol.* 22: 55-79]. As shown in Example 16 below (and FIG. 13A-13B), PU.1 was over-expressed in bone marrow of TgR, as compared to strain matched FVB/N mice, and probably explains why, when exposed to mild inflammatory stress, TgR mice WBC counts recovered faster than FVB/N's, which was attributed to steady levels of granulocytes that were altered by the insult, as well as to an exceptional recovery of monocytes in TgR peripheral blood, likely due to the high PU.1 levels that directed hematopoietic progenitors towards the myeloid lineage. Moreover, AChE-R-induced PU.1 over-expression may also provide a potential mechanism for the prolonged parturition-associated leukocytosis.

Therefore, at the molecular level, ARP, functional fragments or derivatives thereof of compositions comprising the same, may be used for inducing the expression of PU.1. At a physiological level, ARP may be used for boosting the hematopoietic system post-partum. In events of post-partum hemorrhage, for example, where the mother's body loses immense amounts of blood, while still needing to function properly in order to care for the newborn baby, ARP may be used for hematopoietic recovery.

In addition, the present findings point at a previously unperceived option for ex vivo augmentation of post-transplantation thrombopoiesis.

TPO levels are tightly controlled under normal conditions, and increase only when megakaryocyte and platelet production is needed. The current study found a significant increase in TPO levels as well as higher platelet counts in TgR mice over-expressing the stress-induced AChE-R splice variant, as compared to the strain matched FVB/N mice. LPS administration induced a rapid fall in platelet counts in both TgR and FVB/N control mice, however, platelet recovery was considerably faster in TgR mice than in strain-matched controls. Moreover, TgR mice showed faster WBC recovery than controls following LPS-induced inflammation and maintained normal RBC values while control FVB/N mice became pancytopenic for at least 72 hrs post-LPS injection. These differences may be attributed to the augmented capacity of TgR BM progenitors to proliferate and differentiate into pluripotent CFU-GEMM, CFU-GM, and CFU-Mk. Although the inventors' previous reports had indicated the connection between ARP and the megakaryocytic lineage [IL 130224, Inventors' co-pending US Patent Application 2003-0036632, Grisaru (2001) id ibid.], it was not predictable that this connection could also be attributed to the capacity of ARP to enhance TPO circulating levels, as demonstrated in the present invention.

In principle, the AChE-R effect is double bladed. First, it can reduce ACh levels, that way maintaining the production of pro-inflammatory cytokines with growth factor capacities in response to inflammatory signals. Second, it interacts intracellularly with partner proteins, inducing signal transduction pathways and promoting cell proliferation, likely through the AChE-R partner protein RACK1 binding to PKC $\epsilon$ [Perry (2004) id ibid.]. PKC $\epsilon$ was shown to induce megakaryocytic differentiation in HEL and K562 cells [Racke (2001) id ibid.] and in primary human hematopoietic stem cells [Oshevski S. et al. (1999) *Biochem. Biophys. Res. Commun.* 263:603-609; Marchisio M. et al. (1999) *Anat. Rec.* 255:7-14]. Moreover, TPO increases PKC $\epsilon$ expression in mouse megakaryocytes [Rojnuckarin P. et al. (2001) *J. Biol. Chem.* 276:41014-41022], whereas blocking PKC activation inhibits platelet formation [Rojnuckarin P. et al. (2001) *Blood* 97:154-161].

Thus, the elevated levels of AChE-R and PKC $\epsilon$ in megakaryocytes from TgR mice as well as the higher plasma TPO levels in these mice supports the notion of a cholinergic promotion of thrombopoietic signal transduction both through the hydrolytic and the non-enzymatic features of AChE-R, involving two signaling pathways, which may engage PKC$\epsilon$ as well.

The present findings give support to ARP as an inducer of TPO. The inventors had previously described how ARP was able to induce CD34+ cell expansion in combination with various growth factors, particularly GM-CSF and TPO [Deutsch et al. (2002) id ibid.]. However, it was nor clear at the time that ARP by itself could induce the expression of TPO, and increase the levels of circulating TPO. In addition, the present invention shows the effect of ARP on peripheral blood mononuclear cells from adults, besides its influence on CD34+ populations.

Lack of proliferating megakaryocytic progenitors in BM grafts, allo-immunization and refractoriness to platelet transfusions impede recovery of patients with severe thrombocytopenia post bone marrow transplantation. Unfortunately, TPO, the physiological regulator of thrombopoiesis has not been clinically effective due to the paucity of megakaryocyte progenitors in the grafts [Kanamaru (2000) id ibid.]. MGDF, the pegylated form of TPO, was retracted due to immunogenicity in healthy donors who developed anti-TPO antibodies and became severely thrombocytopenic [Basser R. L. et al. (2002) *Blood* 99:2599-2602].

Thus, it is very desirable to find a drug that may more effectively supply TPO for these patients. Hence, administration of a therapeutically effective amount of ARP, its functional fragments or derivatives, or compositions comprising thereof, may be one way of inducing TPO production and consequently increasing the number of megakaryocytic progenitors and platelets.

As mentioned throughout the present specification, said therapeutic effective amount, or dosage, is dependent on severity and responsiveness of the disease state to be treated, with the course of treatment lasting from several days to several months, or until a cure is effected or a diminution of the disease state is achieved. The therapeutic effective dosage may be determined by various methods, including generating an empirical dose-response curve, predicting potency and efficacy of a congener by using quantitative structure activity relationships (QSAR) methods or molecular modeling, and other methods used in the pharmaceutical sciences. Optimal dosing schedules may also be calculated from measurements of drug accumulation in the body of the patient. Persons of ordinary skill can easily determine optimum dosages, dosing methodologies and repetition rates. In general, the dosage may be given once or more daily, weekly, or monthly. Persons of ordinary skill in the art can easily estimate repetition rates for dosing based on the patient's response to the active agent.

Increasing the numbers of megakaryocyte precursors in a graft of hematopoietic precursor cells should shorten the extended period of severe thrombocytopenia, promoting successful engraftment of long term repopulation of stem cells, the appropriate targets for endogenous or exogenous TPO.

In a further aspect, the present invention provides the use of an AChE-derived peptide or its functional fragments or derivatives, in the preparation of a pharmaceutical composition for any one of the treatment and/or prevention of conditions that trigger low granulocyte count, such as leucopenia, and particularly neutropenia, and in pre-transplant priming of hematopoietic stem cells, wherein said peptide is denoted by SEQ ID NO:1.

The preparation of pharmaceutical compositions is well known in the art and has been described in many articles and textbooks, see e.g., Gennaro A. R. ed. (1990) *Remington's Pharmaceutical Sciences*, Mack Publishing Company, Easton, Pa., and especially pages 1521-1712 therein. Essentially the preparation of compositions involves admixing the ARP peptide with pharmaceutically acceptable carriers, diluents or excipients, and further optionally with desirable additives.

Blood cell inflammatory and immune processes involve a finely tuned balance between myeloid cell activation, proliferation and differentiation. Reduced AChE-R densities on the cell surface of B lymphocytes under stress should further increase the chances of ACh to activate these cells by interacting with their ACh receptors [Wang (2003) id ibid.]. The development and stress-induced changes in ACHE gene expression of myeloid cells are hence likely to facilitate the hematopoietic responses to external stimuli.

In an even further aspect, the present invention provides a method of treatment of conditions that induce leucopenia, comprising the steps of administrating a therapeutically-effective amount of an AChE-derived peptide or a composition thereof to a subject in need, wherein said AChE-derived peptide is denoted by SEQ ID NO:1. Leucopenia includes any condition in which the number of white blood cells is reduced. One particular condition is neutropenia.

As mentioned herein, administration of the peptide of the invention, its functional fragments or derivatives, or compositions comprising thereof, is preferably via intravenous. Administration directly into the bone marrow cavity may also be advisable, in order to maximize the contact between ARP and hematopoietic progenitors. Intraperitoneal and intradermal administrations may also be comtemplated.

Thus, the invention also refers to an in vivo method for the prevention and/or treatment of conditions wherein lymphocyte activity is reduced, such as chronic stress, autoimmune diseases, inflammation, rheumatoid arthritis, multiple sclerosis (MS), amyotrophic lateral sclerosis (ALS), fibromyalgia, multiple chemical sensitivity, post-irradiation, chemotherapy in a subject in need, comprising administering a therapeutically-effective amount of an AChE-derived peptide, its functional fragments or derivatives, or compositions comprising thereof, to an individual suffering from or prone to said conditions, wherein said peptide is denoted by SEQ ID NO:1.

Said method may also be accomplished in vitro or ex vivo, similarly to what is described below, through admixing isolated immature blood cells (preferably enriched for the CD34+ population), with ARP for a pre-determined amount of time, which should be sufficient for increasing the number of committed hematopoietic progenitor cells, and especially for cells of the granulocytic and megakaryocytic lineages.

As used herein in the specification and in the claims section below, the term "treat" or treating and their derivatives includes substantially inhibiting, slowing or reversing the progression of a condition, substantially ameliorating clinical symptoms of a condition or substantially preventing the appearance of clinical symptoms of a condition.

As shown in Example 5, B lymphocytes in post-delivery mothers lose most of their surface AChE-R, but maintain high levels of cytoplasmic AChE-R expression, an unprecedented response pattern unique to these cells. This result suggests that the changing pattern of AChE molecules in lymphocytes might reflect a change in lymphocytic activity in response to variations in cholinergic stimuli, under stress situations. Thus, the AChE peptide might be a potent regulator of lymphocytes activity, in vivo, ex vivo and in vitro.

In addition, the invention refers to a method for inducing a shift in the activity of lymphocytes in vitro or ex vivo, comprising contacting an AChE-derived peptide with lymphocytes for a suitable period of time.

Hence also, the present invention discloses a method for detecting changes in the activity of lymphocytes, comprising measuring the expression of AChE-R on the surface of lymphocytes.

As shown in Example 23, priming CB $CD34^+$ cells with $ARP_{26}$ increased significantly the number of human $CD45^+$ cells found in the mouse BM six weeks post transplant. Quantitative PCR analysis confirmed larger content of the human TNFα gene (as a marker for human-originating cells) in mice transplanted with $ARP_{26}$-primed cells. Additionally, incubating CB $CD34^+$ cells for 10 days with 2 nM $ARP_{26}$ improved the recovery from thrombocytopenia in NOD/SCID mice. As shown previously, $CD34^+$ cells placed in culture usually loose their ability for long-term engraft due to differentiation and commitment manifested by the acquisition of the CD38 marker [Guenechea (1999) id ibid.; Li K. (1999) id ibid.]. Nevertheless, these cells produce more AChE-R [Grisaru (2001) id ibid.] and can hence support megakaryopoiesis when mixed with immature $CD34^+$ providing a clear engraftment advantage of $CD45^+$, $CD34^+$ and $CD41^+$ megakaryocyte human cells. The current study proposes a novel strategy to facilitate thrombopoiesis, which involves exposing stem cells to ARP, its functional fragments or derivatives, or a composition comprising thereof, for a pre-determined period of time sufficient for increasing the number of granulocytic and megakaryocytic progenitors. This exposure may be in vivo, through administration of the peptide to a subject in need, or in vitro/ex vivo. When in vitro/ex vivo said exposure involves obtaining hematopoietic cell precursors and admixing said precursor cells with ARP, at concentrations in a range between 0.2 nM up to 100 nM of ARP, preferably between 1 nM and 20 nM of ARP, for a period of between at least 24 hours up to 15 days. Exposed cells may be recovered after 3, 6, 8, 10 or 12 days of incubation with the ARP peptide, its functional fragments or derivatives or compositions comprising thereof. The exposure may be performed by culturing said cells in the presence of ARP. Said treatment aims at improving stem cell engraftment and shortening post-transplant thrombocytopenia.

In addition, the above treatment, or method of priming of hematopoietic stem cells pre-transplant, is also useful for treating a subject in need of granulocytes.

It should be noted that such a pre-transplant priming method may be performed in cells from the subject in need of said transplant, or in cells from another subject, preferably immunocompatible with the host. Thus, the pre-transplant priming may be performed in autologous transplantations or in allogeneic transplantations. In case of allogeneic transplantations, adequate immunocompatible matching host-donor pairs shall be evaluated by the medical professional in care of the patient.

Lastly, the invention also provides an ex vivo method of inducing adult blood cells to produce cytokines, comprising obtaining said cells from a subject in need of cytokine-producing blood cells, isolating immature cells and contacting said cells with an AChE-derived peptide, wherein said peptide is denoted by SEQ ID NO:1.

Thus, cells may be treated as described above, by admixing with or culturing in the presence of ARP, its functional fragments or compositions comprising thereof, but now with the goal of inducing the production of cytokines. These may be, for example, TPO, or pro-inflammatory cytokines, such as TNFα, IL-6 or IL-1β.

This method is particularly advantageous for patients with neutropenia.

Neutropenia is a decrease in circulating neutrophils in the peripheral blood. The absolute neutrophil count (ANC) defines neutropenia. ANC is found by multiplying the percentage of bands and neutrophils on a differential by the total white blood cell count. An abnormal ANC is fewer than 1500 cells per mm$^3$. Neutropenia can be present (though it is relatively uncommon) in normal healthy individuals, notably in blacks and Yemenite Jews.

Causes of neutropenia from disease can be categorized as resulting from decreased production of white blood cells, destruction of white blood cells after they are produced, or pooling of white blood cells (accumulation of the white blood cells out of the circulation).

Diseases causing decreased production of white blood cells include drug toxicity, vitamin deficiencies, and medical diseases such as blood diseases, infections (virus diseases, tuberculosis, typhoid), abnormalities of the bone marrow disorders, or be cyclic (varying in severity week to week, month to month, perhaps related to biorhythms). Several leukemias may also result in neutropenia. Destruction of white blood cells can occur as a result of antibodies attacking the cells (such as in Felty's syndrome) or from drugs stimulating the immune system to attack the cells.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures

Tissue and Cell Preparations:
  Cord Blood (CB) cells were retrieved from umbilical cords of newborns of uncomplicated full-term pregnancies, as described [Grisaru (2001) id ibid.], in anti-coagulant citrate dextrose solution formula A-supplemented bags (Baxter, Deerfield, Ill.).
  Peripheral blood from adult healthy women and from mothers within the first 24 hours post-delivery was obtained from discarded samples of routine blood examinations.
  Only healthy, medication-free patients and neonates and only pregnancies which were uneventful up to term were included in this study.
  Paraffin-embedded sections from electively aborted normal human embryos were prepared as previously described [Grisaru (1999b) id ibid.].
  Peripheral mononuclear and CD34+ cells were enriched to 85% by separation on gelatin and Ficol-Hypaque gradients followed by CD34 immune magnetic beads (Dynal, Great Neck, N.Y.), essentially as described [Grisaru (2001) id ibid.; Pick, M. et al. (1998) *Br. J. Haematol.* 103:639-650]. Alternatively, CD34$^+$ stem cells were purified using a CD34$^+$ progenitor cell isolation kit (PE, Miltenyi Biotec GmbH, Gladbach, Germany), according to manufacturer's instructions.

The use of human material in this study was approved by the Tel Aviv Sourasky Medical Center Ethics Committee according to the regulations of the Helsinki accords.

Animal Models:
  Transgenic Mice
  All animal experiments were approved by the animal ethics committee of The Hebrew University. Transgenic (TgR) mice expressing human AChE-R were generated by injecting a DNA construct including the proximal CMV promoter-enhancer followed by exons 2, 3, 4, pseudointron 4' and exon 5 of the human ACHE gene (GenBank Accession No. M55040) and an SV40 polyadenylation signal, into fertilized eggs of FVB/N mice [Sternfeld et al. (1998b) *J. Neurosci.* 18: 1240-1249]. This transgene presented unimpaired mendelian inheritance over 5 generations [Sternfeld, M. et al. (1998a) *J. Physiol. Paris* 92: 249-255].

To generate acute inflammation, 5 μg LPS of *E. coli* origin (Sigma, St Louis, Mich.) was injected intraperitoneally (IP) in 400 μl of phosphate buffered saline (PBS, Biological Industries, Beth Haemek, Israel). Peripheral blood was drawn from the retroorbital vein of TgS and FVB/N mice, collected in EDTA (7.5%) tubes. Marrow cells were harvested from the mouse femur bones with a 26 G needle pre-washed with heparin, and kept in phosphate-buffered saline (PBS).

NOD/SCID mice: Non-obese diabetic SCID (NOD/SCID) mice were maintained under defined flora conditions in the animal facility at the Weizmann Institute of Science (Rehovot, Israel) in sterile intra-ventilated cages (IVC; Techniplast, Buguggiate, Italy). Mice were sub-lethally irradiated with 375 cGy at 67 cGy/min from a $^{60}$Co source and 24 hrs later were transplanted with 100,000 human cord blood CD34$^+$ cells by intravenous injection in 400 μl of Hank's Balanced Salt solution (HBSS, Biological Industries, Beit Haemek, Israel). Mice were sacrificed between 2 and 6 weeks post transplant, samples of PB (orbital bleed) and BM (femur bone) were removed and human engraftment assessed.

Variant-Specific Antibodies
  Monoclonal human antibody fragments were selected from a phage display library, using ASP, a synthetic peptide with the C-terminal sequence unique to human AChE-S, as target for selection. The 90% pure anti-ASP1 antibody was obtained as soluble single-chain Fv (scFv) including a myc tag and a His6 tail [Flores-Flores, C. et al. (2002) *J. Neural Transm.* 62(suppl):165-179]. Polyclonal affinity-purified rabbit antibodies directed towards the C-terminal sequence unique to human AChE-R (ARP) were obtained after repeated rabbit challenges with a glutathione S-transferase-ARP fusion protein (FIG. 1) [Sternfeld, M. et al. (2000) *Proc. Natl. Acad. Sci. U.S.A.* 97:8647-52].

Detecting AChE Variants
  2×10$^6$ cells (50 μl) were incubated (30 minutes, 4° C.) with anti-CD45-PerCP (20 μl, 0.4 μg; BD Bioscience, San Jose, Calif.) and scFv purified anti-ASP1 (5 μl, 1 μg) or rabbit anti-human polyclonal anti-ARP (5 µl, 1.4 µg), washed with 15 ml 1% BSA in phosphate-buffered saline (PBS), and centrifuged (600×g, 5 minutes, 4° C.). Secondary antibodies were added to 50 µl of resuspended cells (30 minutes, 4° C.), anti-c-myc FITC for detecting anti-ASP (5 µl, 1 µg; Caltag, Burlingame, Calif.) or anti-rabbit-FITC for detecting anti-ARP (3 µl, 3 µg; Zymed, San Francisco, Calif.). Cells were washed as above, and red blood cells were lysed with 1 ml of 1:10 diluted FACS lysis buffer (BD Bioscience, Palo Alto, Calif.; 12 minutes, 4° C.). Non-specific staining was evaluated by incubating with FITC-labeled secondary antibodies and anti-CD45-PerCP only. Surface AChE-R expression was detected on lymphocytes by double-staining with anti-CD19-APC (5 µl, 1 µg; Caltag) to identify B cells or anti-CD3-APC (5 µl, 1 µg; Caltag) to identify T cells. Intracellular proteins were detected in permeabilized cells (IntraStain, Dako, Glostrup, Denmark). Cytochemical staining of catalytically active AChE was performed as previously reported [Lev-Lehman, E. et al. (1997) *Blood* 89:3644-53].

Flow Cytometric Immunophenotyping and AChE-R Detection

To detect AChE-R, cells were incubated with CD45-PerCP (BD Bioscience, Palo Alto, Calif.), followed by permeabilization using the Intrastain Kit (Dako, Glostrup, Denmark), staining with rabbit anti-human $ARP_{26}$ antibodies [Sternfeld, M. et al. (2000) id ibid.], and detection with FITC-conjugated goat anti-rabbit Fab antibody (Jackson Laboratory, Bar Harbor, Me.). Mean fluorescence intensity (MFI) served as a measure of AChE-R content in analyzed cells. When multiplied by the percent fractions of AChE-R-positive cells, the MFI values reflected the total content of AChE-R in the analyzed blood cell samples. Myeloid markers of maternal blood cells were analyzed by the following combination of monoclonal antibodies: anti-CD15-FITC (Dako, Glostrup Denmark), anti-CD33-PE (BD Bioscience, Palo Alto, Calif.), anti-CD45-PerCP (BD Bioscience, Palo Alto, Calif.) and anti-CD14-APC (Caltag, Burlingame, Calif.). Corresponding MFI values reflected the amount of receptor on the surface of granulocytes and monocytes. Expanded CD34+ cells were analyzed by 4-color flow cytometry with FITC-conjugated anti-CD15 and PE-conjugated anti-CD33, PerCP-conjugated anti-CD34, and APC-conjugated anti-CD38 (all antibodies purchased from BD Bioscience, Palo Alto, Calif.) using a FACSCalibur with CellQuest software (BD Bioscience, Palo Alto, Calif.). Relevant isotype control antibodies were used to detect non-specific background fluorescence. The total number of expanded cells for each lineage was calculated by multiplying their relative proportions by the number of viable cells in each culture.

Immunophenotyping of hematopoietic population in mouse bone marrow (BM) and peripheral blood (PB) used the following antibody panels: 1) Gr.1-FITC (clone RB6-8C5, Caltag Laboratories, Burlingame, Calif.), CD11b-PE or -APC (clone M1/70.15, Caltag), CD45-TC (Clone YW62.3, Caltag) to detect the myeloid lineage; 2) CD19-FITC (Clone 6D5, Caltag), CD4-PE (Clone CT-CD4, Caltag), CD3-APC (Clone CT-CD3, Caltag) to detect the lymphoid lineage.

Solubilization of Cellular Antigens:

Cord red blood cells were isolated by centrifugation (600× g, 20 minutes). The plasma and upper layer of cell sediment were removed. Leukocytes were isolated on Ficoll-Hypaque (Pharmacia, Peapack, N.J.). Granulocytes found below the Ficoll-Hypaque layer were isolated and remaining red blood cells were lysed (BD Bioscience, Palo Alto, Calif.). Mononuclear cells found above the Ficoll-Hypaque, containing monocytes and lymphocytes were washed in 1% BSA-PBS (600×g, 5 minutes, 4° C.), re-suspended in 10 ml of Iscove's modified Dulbecco medium (IMDM, Biological Industries, Beit Haemek, Israel) supplemented with 10% fetal calf serum (Biological Industries, Beit Haemek, Israel) and incubated (90 minutes, 37° C., 100% humidity, 5% $CO_2$), allowing monocytes to adhere. Non-adherent cells containing highly enriched lymphocytes were washed with 1% BSA-PBS and adherent monocytes were scraped and washed in 1% BSA-PBS. Cell populations, all above 95% pure (tested with antibodies specific for the population and flow cytometry), were washed with PBS and re-suspended in high salt detergent buffer (300 mM NaCl, 0.5% Triton X-100, 50 mM Tris HCl, pH 7.6), including the protease inhibitor cocktail Complete Mini (Roche Molecular Biochemicals, Mannheim, Germany). After 1 hour shaking at 4° C., samples were centrifuged (10 minutes, 10,000×g, 4° C.). Supernatants were stored at −80° C. for further analysis. Protein concentration was determined using a Lowry assay kit with albumin as protein standard (Bio-Rad, Hercules, Calif.).

Immunoblots:

Anti-ASP1 antibody displayed on the phage surface [Flores-Flores (2002) id ibid.] was used. The pellet of separated cells was resuspended in 10 ml of denaturing buffer (2% SDS, 50 mM Tris HCl, pH 6.8). Soluble cell lysates (6 µg of protein) or plasma samples (to detect AChE-R in circulation, total of 20 µg protein) were run on 4-20% polyacrylamide gels and electroblotted. Membranes were blocked (10% BSA, PBS, 0.5% Tween 20, 18 hours, 4° C.), and incubated with the phage carrying the anti-ASP1 antibody ($2.6 \times 10^8$ transforming units/ml, blocking buffer, 2 h at room temp.) or anti-human $ARP_{26}$ antibodies [Sternfeld (2000) id ibid.]. Following washes (PBS-0.5% Tween20), membranes were incubated with horseradish peroxidase/anti-M13-conjugated or anti-rabbit antibody (Amersham Pharmacia Biotech, Little Chalfont, UK) for 1 hour at room temperature, and diluted 1:10000 in 5% BSA-PBS, 0.1% Tween20. Peroxidase activity was detected using an ECL kit from Amersham. Blots were analyzed using the luminescence tool of Adobe Photoshop 7.0 ME (Adobe Systems, Inc., San Jose, Calif.).

Surface Plasmon Resonance (SPR):

SPR measurements (BIAcore 3000 System, Uppsala, Sweden) used the anti-ASP1 scFv and anti-ARP antibodies immobilized on a CM5 sensor chip through their primary amine groups [Johnsson, B. et al. (1991) *Anal. Biochem.* 198:268-77]. The matrix was activated with 70 µl of 0.4 M N-ethyl-N'-(dimethyl-aminopropyl)-carbodiimide and 0.1 M N-hydroxysuccinimide, and 200 µg/ml of the particular antibody in 10 mM sodium acetate, pH 3.5, were injected at a flow rate of 10 µl/min in 10 mM HEPES, pH 4.0, 150 mM NaCl, 3.4 mM EDTA and 0.005% polysorbate 20 to reach surface density of between 3000 to 6000 resonance units (RU). Remaining activated carboxyl groups were blocked by injecting 70 µl of 1 M ethanolamine hydrochloride. Cord blood cell extracts in high salt detergent buffer were brought to 0.83 mg protein/ml in 10 mM HEPES pH 4.0 with 150 mM NaCl, 3.4 mM EDTA, 0.005% polysorbate 20. Carboxymethyl dextran was added to avoid non-specific binding of protein to the surface matrix. 60 µl extract doses were injected through the flowcell to which the antibody was immobilized and through a reference surface (to which no antibody was immobilized) for 2 minutes. A 10 µl pulse of 2 M NaCl achieved regeneration of the antibody in the flowcell. Data management involved multi-parameter Student's t-test statistics with p values<0.05 considered significantly different.

Cell Counts and Serum Tests

Plasma was separated from blood samples used for cell counts with the Coulter Gen-S analyzer (Beckman Coulter, Miami, Fla.). Plasma cortisol levels were measured by electrochemiluminescence immunoassay (ECLA) and analyzed by Elecsys 1010/2010 and modular analytics E170 (Roche, Indianapolis, Ind.). AChE activity was determined in the plasma by a standard calorimetric assay in the presence of $10^{-5}$ iso-OMPA, a selective inhibitor of butyrylcholinesterase (BChE). Mononuclear cells ($2.5 \times 10^6$ cells/mL) from healthy adult women were cultured for 24 hours in the presence or absence of the noted peptides. The supernatant was collected following centrifugation (4300 rpm, 10 min) and filtration (0.2 µm). Cytokine levels, including TNFα, IL-1β, IL-6, IL-10 and IL-12p-70, in the plasma and cell supernatants were assessed by flow cytometry (BD Bioscience, San Jose, Calif.) using a particle-based immunoassay (CBA kit, BD Bioscience, Palo Alto, Calif.). Data acquisition and analysis utilized CellQuest and Microsoft Excel software (BD Bioscience, Palo Alto, Calif.).

In Situ Hybridization

In situ hybridization procedures were performed on freshly isolated cells using 5'-biotinylated, 2'-O-methylated AChE cRNA probes complementary to 3'-alternative human ACHE exons as previously described [Grisaru (2001) id ibid.]. Labeling intensity was assessed as the percent cytoplasmic red pixels and normalized by subtraction of background signals. Confocal microscopic scans of the cells were obtained using a MRC-1024 Bio-Rad confocal microscope (Hemel Hempsted Herts., UK). ANOVA and t-test were used for statistical calculations.

RT-PCR and Real Time RT-PCR

Total RNA was purified from bone marrow with the RNeasy kit (Qiagen), followed by treatment with DNase I (Qiagen) according to manufacturer's protocol. RNA quality was confirmed by electrophoresis on agarose gel, and analysis of OD ratios at 260 nm versus 280 nm—all values were between 1.8 and 2.1. cDNA was prepared from this RNA using the Improm II kit (Promega, Madison, Wis.). For each reaction, 2.4 µl of 25 mM $MgCl_2$, 4 µl of X5 buffer, 1 µl reverse transcriptase, 1 µl dNTP mix (10 mM of each), 1 µl random hexamers (of 50 µM stock, Sigma), 0.5 µl RNase inhibitor (20 U, Promega) and 2 µl sample RNA (200 ng/µl) were mixed with diethyl pyrocarbonate (DEPC) water to a final volume of 20 µl. The reverse transcription reaction was 45 minutes at 42° C., 5 minutes at 90° C., and then the samples were left at 4° C.

Experiments with real-time quantitative PCR were performed with the Lightcycler™ system (Roche, Switzerland) and SYBR Green PCR Master Mix (Applied Biosystems). Primers for Ikaros1 and mCtBP were designed using the Lightcycler™ sequence-detection software (Roche, Switzerland). Primer sequences for mFOG, mGATA1, Runx 1/AML1, PU1, β-globin, STATS, and the housekeeping gene β actin (SEQ ID NOS:3-14), as well as amplification conditions, are listed in Table 1. Purity of the PCR products was verified by a melting curve analysis using the Lightcycler™ system, and by agarose gel analysis.

TABLE 1

Primer sequences used for Real Time PCR

| Primer | Sequence | Annealing temperature |
|---|---|---|
| GATA1 + (SEQ ID NO: 3) | 5'-3' TCTTCTCTCCCACTGGGAGCCCT | 65° C. |
| GATA1 - (SEQ ID NO: 4) | 5'-3' CTTCTTGGGCCGGATGAGAGGCC | |
| LMO2 + (SEQ ID NO: 5) | 5'-3' TGGATGAGGTGCTGCAGATA | 65° C. |
| LMO2 - (SEQ ID NO: 6) | 5'-3' CCCATTGATCTTGGTCCACT | |
| RUNX1/AML1 + (SEQ ID NO: 7) | 5'-3' ACTTCCTCTGCTCCGTGCTA | 65° C. |
| RUNX1/AML1 - (SEQ ID NO: 8) | 5'-3' GTCCACTGTGATTTTGATGGC | |
| PU.1 + (SEQ ID NO: 9) | 5'-3' GATGGAGAAAGCCATAGCGA | 55° C. |
| PU.1 - (SEQ ID NO: 10) | 5'-3' TTGTGCTTGGACGAGAACTG | |
| STAT5b + (SEQ ID NO: 11) | 5'-3' GGGACTCAATAGATCTTGATAATCC | 65° C. |
| STAT 5b - (SEQ ID NO: 12) | 5'-3' AACTGAGCTTGGATCCGCAGGCTCT | |
| Actin + (SEQ ID NO: 13) | 5'-3' CAATTCCATCATGAAGTGTGAC | 65° C. |
| Actin - (SEQ ID NO: 14) | 5'-3' ATCTTGATCTTCATGGTGCT | |

For quantification of transcript levels, the target concentrations at which each transcript was amplifying at the log linear range was tested, using serial dilutions of cDNA preparations (1:1, 1:3, 1:9, 1:81, where 1:1 corresponds to a concentration of 400 ng/ul at the reaction mix). The efficiencies for all targets were very similar (amplification of $\sim n^{1.8}$ per PCR cycle) when RT products were diluted 1:5. Amplification reactions were performed in a final volume of 10 µl containing 1 µl of 5-fold diluted RT reaction product, 1 µl SYBR Green PCR Master Mix, 10 µM primer, and nuclease-free water.

Acetylthiocholine Hydrolyzing Activity (AThCh)

Mouse plasma samples were separated from the nucleated cell fraction by centrifugation at 4300 rpm (2000×g, 20 min) sterilized through a 0.2 µm pore size filter and stored in aliquots at −70° C. until use. BM cells were washed with PBS (Sigma) and re-suspended in low salt detergent buffer (300 mM NaCl, 0.5% Triton X-100, 50 mM Tris HCl, pH 7.6), containing protease inhibitor cocktail (Roche Molecular Biochemicals). AThCh activity was as previously described [Kaufer (1998) id ibid.].

Ex Vivo Expansion of Hematopoietic Progenitor Cells:

For cell priming experiments 100,000 fresh CB CD34+ cells were supplemented with 2 nM of peptide, $ARP_{26}$ [Grisaru (2001) id ibid.], $ASP_{40}$ [Grisaru (2001) id ibid.] or no supplement for 2 hours and injected into mice. For 10 day cultures CB CD34+ cells were expanded in liquid cultures in the presence of one of the following growth supplements: $ARP_{26}$ (2 nM, synthetic peptide), $ASP_{40}$ (2 nM, synthetic peptide), rhu-TPO (1 ng/mL) (R&D) together with rhu-SCF (50 ng/mL; Genzyme Diagnostic, Cambridge, Mass., USA) or no supplement (control). $ARP_{26}$, and $ASP_{40}$ were synthetically produced. PBAN (a negative control insect peptide) [Nijholt (2003) id ibid.] were also used for cell expansion. Liquid cultures were initiated and maintained in 24-well tissue culture plates ($1\times10^5$ cells/well in 1 mL). Cells were grown for 10 days at 37° C. in 5% $CO_2$ in a fully humidified atmosphere in IMDM supplemented with 5% autologous plasma. At 3-day intervals, cultures were supplemented with the same growth factor(s) and cells were counted by trypan blue exclusion and diluted to maintain cultures at concentrations no higher then 100,000 cells/mL [Pick M. et al. (2002) Exp. Hematol. 30:1079]. Cultured cells were injected into NOD/SCID mice at a concentration of 100,000 or 200,000 together with 100,000 unexpanded CD34+ cells per mouse as indicated.

Progenitor Colony Assays

GM-CFU: mouse BM cells were cultured at $2\times10^5$ cells per 35 mm tissue culture dish (Corning Inc., NY) in IMDM (Biological Industries, Beit Haemek, Israel) supplemented with 0.8% methyl cellulose (Sigma-Aldrich Corp., St. Louis, Mo.), 10% FCS (Biological Industries, Beit Haemek, Israel) and $5\times10^{-4}$ M 2-beta-mercaptoethanol (2-ME) (Sigma), 5 ng/mL recombinant mouse-granulocyte macrophage-colony stimulating factor (rmo-GM-CSF, R&D Systems Inc., Minneapolis, Minn.), 10 ng/mL rmo-stem cell factor (rmo-SCF, R & D), 3 U/mL rhu-erythropoietin (rhu-EPO, R & D Systems Inc., Minneapolis, Minn.) and rmo-Interleukin-3 (rmo-IL-3, R & D) in 5% $CO_2$ at 37° C. Colonies of more than 40 cells were counted at day 10.

BFU-E: $2\times10^5$ BM cells per 35 mm dish were cultured in Alpha-MEM (Biological Industries, Beit Haemek, Israel) supplemented with 0.8% methyl cellulose, 10% FCS, 10% bovine serum albumin (BSA, Boehringer Ingelheim GmbH, Germany) and $5\times10^{-4}$ M 2-ME, 3 U/mL rhu-EPO and 10 ng/mL rmo-SCF. Red cell clusters were counted at day 12 of incubation in 5% $CO_2$ at 37° C.

CFU-Mk: $2\times10^5$ BM cells per 35 mm dish were cultured in McCoy's Medium (Biological Industries, Beit Haemek, Israel) supplemented with 0.3% agar (Difco, Mich.), 10% FCS and $10^{-4}$ M 2-ME, 2 ng/mL rmo-thrombopoietin (rmo-TPO, R&D Systems Inc., Minneapolis, Minn.) and 10 ng/mL rmo-SCF in 5% $CO_2$ at 37° C. for 10 days. Plates were placed into an oven for 2 hrs at 45° C. with Whatmann No. 1 filter paper discs carefully placed over the agar layer. The filter paper was then gently removed and plates incubated with AChE substrate (10 mg acetylthiocholine iodide dissolved in 15 mL of 0.1M dibasic sodium phosphate, 1 mL of 0.5 M sodium citrate, 2 mL 30 mM cupric sulfate and 2 ml 5 mM potassium ferricyamide) for up to 24 hrs at room temperature or until colonies turned brown in color.

Quantification of Cytokine Levels

Mouse TPO, EPO, Tumor necrosis factor-alpha (TNF-α and IL-6 levels in plasma of TgR and FVB/N mice were determined using Quantikine murine enzyme-linked immunosorbent assay (ELISA) kits (R&D), according to the manufacture's instructions.

Immunohistochemistry

BM cell smears were fixed for 15' with methanol, washed 3 times with PBS and then 3 times with 100 mM glycine to quench auto-fluorescence. Blocking buffer included 1% donkey (Santa Cruz Biotechnology Inc., Santa Cruz, Calif.), or 1% goat serum (Santa Cruz) for 30 min at room temperature. Antibodies against human AChE-R (Rabbit, 0.6 ug/slide) [Sternfeld M. et al. (2000) Proc. Natl. Acad. Sci. USA 97:8647-8652], PKC ϵ (mouse, 0.5 ug/slide) (BD Biosciences, Palo Alto, Calif.) and RACK1 (mouse, 0.25 ug/slide) (BD Bioscience, Palo Alto, Calif.) were incubated for 60' with blocking buffer. TBST (Tris buffered saline with 0.2% Tween 20) was used to wash slides after each antibody incubation. For detection, biotin-SP-conjugated AffiniPure goat anti mouse IgM or donkey anti rabbit IgG (1:200, Jackson ImmunoResearch Laboratories Inc., West Grove, Pa.) and Cy3™ conjugated streptavidin (1:200, Jackson ImmunoResearch Laboratories Inc., West Grove, Pa.) were each incubated for 30 min at room temperature. May-Grünwald staining was performed to morphologically identify megakaryocytes.

Detection of Human Cells Engraftment in NOD/SCID Mice

NOD/SCID mice were sacrificed 2 to 6 weeks post-transplantation and PB and BM were analyzed following lysis of mature RBCs with FACS lysis buffer (BD Bioscience, Palo Alto, Calif.). $5\times10^6$ cells were incubated with human antibodies anti-CD41a-FITC (Beckman/Coulter, Fullerton, Calif.), anti-CD34-PE (BD Bioscience, Palo Alto, Calif.) and anti-CD45 PerCP (BD Bioscience, Palo Alto, Calif.) (30 min, 4° C.). To follow human platelet engraftment, PB of NOD/SCID mice was stained with anti-human CD41a-FITC and anti-mouse CD41a-PE (BD Bioscience, Palo Alto, Calif.), and a specific platelet gate was placed at acquisition.

At least 500,000 events per sample were acquired with a BD FACS Calibur (BD Bioscience, Palo Alto, Calif.). Data analysis used Cell Quest and Cell Quest Pro software (BD Bioscience, Palo Alto, Calif.). Matched isotype controls for all antibodies were used to detect background fluorescence (supplied by Caltag and BD Bioscience, Palo Alto, Calif.). All human antibodies were pre-tested on naïve-untransplanted mice to test for any cross-reactivity. To detect human-originated cells, BM DNA was extracted (QIAprep Spin Miniprep Kit, Qiagen) according to manufacturer instructions. DNA samples (100 ng, 2 µl) were incubated in 10 µl containing 1 µl Light Cycler™ DNA master hybridization probe (Roche Molecular Biochemicals). 1 µl primers (5 µM sense and 5 µM antisense), 1 µl probes, (5 µM anchor and 5 µM sensor), 1.2 µl $MgCl_2$ (3 mM) and nuclease-free water. TNFa primer and probe sequences are listed below in Table 2 (SEQ ID NOS: 15-20). PCR involved 45 cycles (95° C. for 10 sec, 65° C. for 7 sec, and 72° C. for 20 sec). Standard curves were generated by mixing mononuclear cells (MNCs) from human CB together with mouse BM, total number of cells being $5\times10^6$ per concentration with mixtures of 0, 0.5, 1, 2, 5, 10, 20, 40, 60, 80 and 100% human cells. The human probe and primer were found negative in naïve mice.

TABLE 2

| DNA seuuence of primers and probes for TNFα. | | |
|---|---|---|
| Name | 5'-3' sequence | Sequence Name |
| Human sense | AGGAACAGCACAGGCCTTAGTG | SEQ ID NO: 15 |

TABLE 2-continued

DNA seuuence of primers and probes for TNFα.

| Name | 5'-3'sequence | Sequence Name |
|---|---|---|
| Human antisense | AAGACCCCTTCCAGATAGATGG | SEQ ID NO: 16 |
| Human probe | GCCCCTCCACCCATGTGCTCC-FLAC-RED640 | SEQ ID NO: 17 |
|  | CACCCACCACCATCAGCCGCATC | SEQ ID NO: 18 |
| Mouse sense | GGCTTTCCGAATTCACTGGAC | SEQ ID NO: 19 |
| Mouse antisense | CCCCGGCCTTCCAAATAAA | SEQ ID NO: 20 |

FL- sensor, AC- anchor
*Nucleotide sequences are based on human and mouse TNF α genes (GenBank Accession Numbers M26331 and Y00467, respectively) [Nitsche A. et al. (2001) *Haematologica* 86: 693-699].

Example 1

Evaluating AChE Splice Variants in Hematopoietic Cell Populations

Cytochemical staining of smeared blood cell preparations revealed acetylthiocholine-hydrolysing AChE in blood cells from the newborn, adult and postpartum sources. Particularly prominent intracellular staining was observed in adult and post-partum granulocytes, whereas enzyme activity on the cell surface was clearly observed on lymphocytes, granulocytes and monocytes from adult blood, compatible with the inventors' previous findings [Lev-Lehman (1997) id ibid.], but only on granulocytes from post-partum mothers. FIG. 2A portrays representative micrographs (one cell from 30 analyzed) of this staining, and FIG. 2B includes activity staining combined with morphology.

To attribute enzyme activities to specific AChE variants and explore their surface-cytoplasmic localization, flow cytometry was used, which combines physical characteristics of these cells with specific surface antigens. CD45, a glycosylated trans-membrane phosphatase which is expressed on the membrane of granulocytes, monocytes and lymphocytes at different intensities, but not in erythrocytes [Craig, W. et al. (1994) *Br. J. Haematol.* 88:24-30; Xu, Z. and Weiss, A. (2002) *Nat. Immunol.* 3: 764-71]. CD45 was used to identify these blood cell populations from several human sources, which included adult non-pregnant women, adult women post-partum and cord blood from their newborns.

Antibodies directed to the unique C-terminal sequences of human AChE-S [Flores-Flores (2002) id ibid.] and AChE-R [Sternfeld (2000) id ibid.] were used in conjunction with CD45 labeling to analyze the expression of the corresponding variants or fragments thereof in the sub-classified blood cell populations. Flow cytometry measurements using naive or permeabilized cells enabled distinction between cell surface and intra-cellular localization of these variants (FIG. 2C). Quantitative values were expressed as either percent positive cells (expression levels) within each population or mean fluorescence intensities of the positive fraction, which reflected content of the corresponding variant protein in each population (see below).

In blood cells from post-partum mothers, this analysis expectedly showed very low to undetectable levels of AChE-S and —R on the surface and in the cytoplasm of red blood cells (RBCs), compatible with AChE-E being the variant that is present and active in these cells. Increased fluorescence, measured by a shift in histogram patterns compared to background, reflected the presence of substantial AChE-S and -R levels in all of the CD45+ populations. The levels of expression of the AChE-S and AChE-R variants in post-partum peripheral blood granulocytes and monocytes was higher (both on the surface and in the cytoplasm) than in lymphocytes, which showed low levels on the surface, and somewhat higher levels in the cytoplasm (FIG. 3). The surface-cytoplasmic distribution of enzymatically active AChE within blood cells thus presented lineage-specific differences that were altered both during development and following the stress of childbirth.

Example 2

Differential Concentrations of AChE Variants Within Specific Blood Cell Types

An independent quantification of AChE variant levels within specific blood cell types was obtained using the BIAcore technology, based on measuring the interaction of proteins in cell homogenates with antibodies covalently linked to a carboxymethyl dextran matrix adherent to the surface of a gold leaf sensor [Johnsson (1991) id ibid.]. Increases in the refractive index of this sensor were monitored in real time as the changes in surface plasmon resonance (SPR) angle (FIG. 4A). Non-specific SPR signals obtained in the absence of antibodies were subtracted, and protein levels were standardized either to the amount of total protein or to the number of lysed cells in each preparation, irrespective of their cellular localization (FIG. 4B).

Because cord blood lysates were examined at only one antibody concentration and one lysate concentration, the BIAcore measurements could only reflect relative antigen interaction with the antibodies, but not absolute affinity values. These relative amounts of each variant were compared within specific cell types and between the four hematopoietic cell groups. When applied to newborn cord blood cell extracts, larger signals were detected for AChE-S than for -R. Decreasing concentrations (reflected in resonance units, RU/mg protein) of AChE-S occurred in the order of granulocytes>lymphocytes>monocytes>red blood cells. A different decreasing order, lymphocytes>monocytes>granulocytes>red blood cells, was calculated per cell, suggesting that the high granulocyte concentration of AChE-S reflected the high total protein content. AChE-R signals, which were generally lower, presented similar decreasing orders in both measures (lymphocytes>monocytes>granulocytes>red blood cells, FIG. 4B). The BIAcore and flow cytometry methods revealed distinct R:S ratios, e.g. for granulocytes from cord blood (FIGS. 3, 4), perhaps due to different properties of the two antibodies.

A third evaluation approach involved immunoblot analysis of the corresponding cell homogenates using the AChE-S specific ASP antibody displayed on phage surface (FIG. 4C). This analysis demonstrated several immunopositive protein bands in granulocytes and lymphocytes, most of which of smaller size then the predicted full protein. A single rapidly migrating band appeared in red blood cells, with fainter, similarly migrating band in myeloid cells. These bands likely reflect proteolytic breakdown products (or fragments) of the ACHE-S protein in blood cells. Additionally, or alternatively, the cleaved C-terminus of AChE-S [Grisaru (1991) id ibid.] or an immunocompatible variant could be exposed in cell homogenates but not in intact cells.

Example 3

Distinct Splice Variations in Development and Stress

Calculating the AChE-S/AChE-R distributions as percent of positive cells in each lineage revealed distinct splice variations in development and stress. Most cell populations included significant fractions of cells positive for both cytoplasmic and surface AChE-S and -R variants, with significantly higher numbers of AChE-R expressing cells in all adult myeloid cell populations than in fetal cells (FIG. 5). The number of granulocytes expressing cytoplasmic AChE-R was significantly higher in post-partum blood ($p<0.05$), reminiscent of the increase in AChE-R seen in brain neurons under stress [Kaufer (1998) id ibid.; Meshorer et al. (2002) id ibid.; Soreq and Seidman (2001) id ibid.]. However, AChE-S, which is known to adhere to the membranes of brain neurons was expressed on the surface and in the cytoplasm of significantly more blood cells in post-partum mothers than in non-pregnant women (Students t-test, $p<0.05$). In addition, post-partum lymphocytes displayed a paradoxical decrease in surface AChE-R. The localization of AChE-R to the cell surface, which was rather surprising in view of its hydrophilic C-terminal peptide, may reflect interaction with as yet unknown protein variant(s) [Birikh (2003) id ibid.].

Example 4

Surface and Cytoplasmic AChE-S and AChE-R Contents in Peripheral Blood Cells

High fluorescence intensity from comparative flow cytometry confirmed the increased protein content of the AChE-R variant compared to AChE-S of all cell types and sources tested. AChE-R protein content of granulocytes, which comprise 70 to 80% of the white blood cell compartment, were significantly higher in post-partum mothers compared to cord blood cells (Table 3), reflecting a strikingly different splicing pattern for AChE pre-mRNA in fetal blood cells than in adult cells under the post-partum stimulus. Cytoplasmic increases in AChE-R content, observed as larger mean fluorescence intensity values, occurred under stress in all cell lineages. Stress-induced increases in cell surface AChE-R appeared in granulocytes and monocytes, but not in red blood cells. In lymphocytes, cell surface AChE-R increased 8-fold from newborns to adults but declined under stress (Table 3).

TABLE 3

AChE variant contents in blood cells

| | | Mean Fluorescence Intensity (MFI)[a] | | | |
| | | AChE-S | | AChE-R | |
| | % of blood leukocytes[b] | Cytoplasmic | Surface | Cytoplasmic | Surface |
| --- | --- | --- | --- | --- | --- |
| RBCs | | | | | |
| CB | NA | 4.7 ± 1.6 | 1.4 ± 0.1 | 6.9 ± 0.3 | 4.1 ± 0.4 |
| APB | NA | 4.8 ± 0.6 | 1.4 ± 0.3 | 5.0 ± 0.3 | 4.7 ± 2.1 |
| PPB | NA | 4.5 ± 0.4 | 4.7 ± 0.1 | 18.5 ± 1.2 | 5.8 ± 0.6 |
| granulocytes | | | | | |
| CB | 39-63 | 30.1 ± 15.1 | 19.4 ± 3.3 | 57.9 ± 2.7 | 42.8 ± 3.4 |
| APB | 43-65 | 11.1 ± 0.5 | 6.1 ± 0.3 | 32.9 ± 3.9 | 62.9 ± 3.5 |
| PPB | 69-82 | 9.1 ± 0.4 | 30.1 ± 0.4 | 96 ± 3 | 138 ± 10 |
| monocytes | | | | | |
| CB | 6-12 | 21.3 ± 0.1 | 22.3 ± 3.9 | 42.7 ± 3.0 | 29.1 ± 1.7 |
| APB | 6-12 | 10.3 ± 0.3 | 9.5 ± 0.7 | 17.8 ± 1.7 | 27.1 ± 6.4 |
| PPB | 6-12 | 14.7 ± 0.8 | 21.3 ± 0.7 | 57.5 ± 2.6 | 72 ± 5.8 |
| lymphocytes | | | | | |
| CB | 42-62 | 10.4 ± 1.3 | 9.7 ± 1.7 | 16.1 ± 0.5 | 24 ± 2 |
| APB | 21-46 | 4.8 ± 0.3 | 2.2 ± 0.1 | 8.2 ± 0.7 | 183 ± 11 |
| PPB | 13-23 | 5.7 ± 0.3 | 10.4 ± 0.2 | 25.7 ± 1.1 | 37 ± 2 |

[a]Average of 15 measurements for each population expressed as mean ± standard error are presented.

[b]Proportions of white blood cells expressed by peripheral blood leukocyte populations. Significantly different MFI values as compared with the other two sources according to t-test ($p < 0.05$) analysis are presented in bold face type.

Example 5

Development and Stress-Induced Changes in Lymphocytic AChE Variants

Previous reports attributed lymphocytes' AChE activity to T cells and described its increases with mitogenic stimulation [Szelenyi et al. (1987) *Immunol. Lett.* 16: 49-54]. Activity was also observed in the thymus [Topilko and Caillou (1985) *Blood* 66: 891-5], but B lymphocytes displayed very low levels of AChE, which decreased with maturation [Szelenyi et al. (1982) *Br. J. Haematol.* 50: 241-5]. In the present study, CD3+ T cells presented low expression of surface AChE-R in all samples while CD19+ B cells expression was significantly higher (FIG. 6A), suggesting that AChE-R may be relevant for antibody production. Due to the majority of T cells (about 9:1 to B cells, FIG. 6A, inset), their small signals contributed significantly to the total lymphocyte output. Nevertheless, B cells displayed a significant increase in fluorescence intensity from newborn cord blood to adults and post-delivery blood cells, with no change between the latter two fractions (FIG. 6B). Larger lymphocyte fractions expressed surface AChE-R in separate T and B cell populations, likely due to the high background staining in the T lymphocyte fraction (FIG. 6A).

In conclusion, considerably more myeloid cells of the post-partum mothers expressed AChE-S and AChE-R than in either control women or newborns. In contrast, B lymphocytes lost their surface AChE-R with development and under stress.

Example 6

Fetal AChE-R mRNA Expression Coincides with Myelopoiesis

The in vivo expression of alternative AChE mRNA transcripts (FIG. 7A) was studied by in situ hybridization using paraffin-embedded human fetal sections from different gestational ages (FIG. 7A). AChE mRNAs were observed in the aorta-gonad-mesonephric region (AGM), liver, spleen and bone marrow, consistent with the spatiotemporal shifts of hematopoietic embryogenesis and the migration of fetal hematopoiesis through the various blood forming tissues (FIG. 7C). Clear changes occurred in developing liver, with distinct labeling intensities for each of the AChE mRNA transcripts at different gestational ages (FIG. 7D). At 9 weeks gestation, when the liver and spleen are initiating definitive hematopoiesis, the erythrocytic AChE-E mRNA transcript was prominently displayed in the AGM, liver and spleen. Significant levels of the synaptic transcript (AChE-S mRNA) were found at this time in the AGM region and liver, but not in spleen, while the AChE-R mRNA variant was barely detectable in all hematopoietic tissues. At 16 weeks, during accelerated myelopoiesis, AChE-S was elevated in both liver and spleen in agreement with findings of others [Chan (1998) id ibid.]. A decrease in AChE-E mRNA concurrent with an increase in AChE-R mRNA was observed in the liver, suggesting a splicing shift (FIG. 7E). Subsequent decreases in all AChE mRNA variants were observed until 25 weeks. These changes were concomitant with the switch from primitive hematopoiesis, which is exclusively erythrocytic, to definitive hematopoiesis of all lineages. These results suggest that AChE-R overproduction is causally associated with myelopoiesis in vivo.

Example 7

Intra-Partum Cortisol Escalation Associates with Increased Granulocytic AChE-R Expression Cortisol levels were predictably elevated intra-partum as compared to an age matched population of 48 control Caucasian women (36.6±4.2 vs. 21.3±11.2 µg/dL, p<0.001; FIG. 8A). Intra-partum serum cortisol levels showed direct correlation with WBC counts (Pearson correlation; R=0.55, p=0.04; FIG. 8E). This was accompanied by elevated expression of AChE-R in the cytoplasm of mature WBC as detected by flow cytometry (p=0.009; FIG. 8F). Direct, significant correlation of cortisol levels with the fraction of AChE-R positive granulocytes (R=0.72, p=0.003; FIG. 8G), but not monocytes or lymphocytes, was consistent with the predicted role of AChE-R in post-partum granulocytosis.

Example 8

Sustained Peri-Partum Granulocytosis

To explore the relevance of cholinergic changes for intra-partum granulocytosis, the peri-partum hematopoietic changes in blood samples was studied. Sixteen patients with premature rupture of membranes at term (PROM, rupture of membranes without uterine contractions) were followed, from admission through delivery and post-partum periods (27.08±14.22 and 61.82±15.99 hours post admission, respectively). WBC counts in these patients were higher than the pre-delivery average and increased significantly intra-partum (P<0.0001; FIG. 9A). Hemoglobin levels maintained normal to low range before delivery and decreased significantly intra- and post-partum (P=0.01), compared to the baseline values, reflecting blood loss during labor. Platelet counts remained stable and in the normal range during the entire study period (FIG. 9A). Although WBC counts decreased post-partum, they remained significantly above normal ranges (P=0.01)), reflecting increased granulocyte counts (intra-partum: P<0.0001; post-partum: P=0.02). Monocyte and lymphocyte counts remained in the low normal range (FIG. 9B). In vivo parturition was therefore considered appropriate for assessing the effects of a transient stressful event on granulocytosis.

Example 9

Granulocytic AChE-R Expression Maintains High Post-Partum Levels

Cortisol levels were high pre-partum (30.6±8.2 vs. 21.3±11.2 µg/dL in age-matched control population, P<0.001), increased intra-partum (32.1±12.2 µg/dL; P<0.001 compared to matched controls), and decreased significantly post-partum (27.2±10.6 µg/dL, P=0.05 compared to the intra-partum values; FIG. 8A) to levels that are not statistically different than those of the matched control population. Serum AChE activity increased as compared to controls (21.6±7.2 vs. 5.5±1.9 nmole/min/mg protein; p<0.001) and remained significantly elevated during the entire period (FIG. 8B). A significant increase was observed in the number of granulocytes expressing cytoplasmic AChE-R, both intra- and post-partum as compared to pre-partum (from 1.7±0.6×10$^3$ cells/

μL to 5.2±0.5 and 4.9±0.4×10³ cells/μL, respectively, P=0.05; FIG. 9D). This pattern of expression was not reflected in monocytes or lymphocytes (FIG. 9D), consistent with the idea that AChE-R may have a selective role in the prolongation of peri-partum granulocytosis. High serum levels of AChE-R were found throughout the peri-partum period (FIG. 9D), supporting the notion that serum AChE activity reflected sustainable AChE-R levels, facilitating parturition anxiety [Sklan, E. H. et al. (2004) *Proc. Natl. Acad. Sci. USA* 101(15): 5512-5517].

Example 10

Parturition Effects on Myeloid Markers

To determine the effect of parturition on the myeloid lineage, applied flow cytometry to study the expression of CD15 (a marker of granulocytes), CD 33 (a marker of early myeloid cells) and CD14 (which is expressed on myeloid cells and is often used as a marker of monocytes) on peripheral blood WBC. CD15 expression on granulocytes decreased significantly in intra-partum samples (535±287 vs. 294±129 MFI, P=0.03; FIG. 9C-9D) and its post-partum levels returned to baseline, while CD33 expression did not change significantly over the entire period. This may represent a cumulative effect of rapid production and release of early myeloid cells from the bone marrow on the one hand, accompanied by their rapid maturation on the other hand. Additionally, CD14 expression on monocytes did not vary, while post-partum CD33 expression decreased significantly (145±89 vs. 91±40 MFI, P=0.05; FIG. 9C-9D).

Example 11

Leukocyte AChE-R Contents Positively Associate with Plasma AChE Activity

Total AChE-R contents in blood cells were evaluated by multiplying the mean fluorescence intensity (MFI) per the percent of positive cells expressing AChE-R in each cell type (granulocytes, monocytes and lymphocytes) detected by flow cytometry. In each type of circulating WBC, AChE-R contents correlated with AChE activity in the post-partum plasma (for granulocytes R=0.984, p<0.0001; for monocytes R=0.962, p<0.0001; and for lymphocytes R=0.917, p<0.0001; FIG. 10). Plasma AChE activity levels thus reflected AChE-R production in each type of leukocyte.

Example 12

$ARP_{26}$ Enhances Endogenous ACHE Gene Expression

Assuming a turnover number of $1\times10^4$ molecules of ACh hydrolyzed/second/AChE subunit, and based on the inventors' previous findings [Cohen (2003) id ibid.], up to one-half of the AChE-R is C-terminally cleaved in vivo to yield ARP, the AChE-R C-terminal peptide. Therefore, the measured rates of ACh hydrolysis in the serum of post-partum mothers predicted a peptide concentration in the range of 5-30 nM. It was further hypothesized that comparable peptide concentrations are found in the bone marrow, and the potential ex vivo effects of $ARP_{26}$ at 0.2, 2.0 and 20 nM on CD34+ progenitors. In situ hybridization followed by confocal quantification of the three AChE mRNA variants revealed increased levels of all AChE mRNA transcripts 24 hours following the addition of $ARP_{26}$ to the medium. This was accompanied by increased cytochemically stainable cellular ACh hydrolytic activity reflecting accumulated AChE protein in the $ARP_{26}$-treated cultured cells (FIG. 11C). The enhanced activity under physiologically relevant concentrations of $ARP_{26}$ reflected an increase in endogenous AChE, since the synthetic peptide has no enzymatic capacity. It also provided a possible explanation for the sustained AChE activity in peri-partum sera, since it occurred with 2 nM $ARP_{26}$ and to a similar extent in mammals exposed to stress-associated cortisol levels [Grisaru (2001) id ibid.].

Example 13

$ARP_{26}$ Potentiates Myelopoiesis in Liquid Cultures

To test the long-term effect of $ARP_{26}$ on myelopoietic expansion, flow cytometry was used to monitor the development of phenotypically distinct cell populations from human CD34+ hematopoietic stem cells incubated with $ARP_{26}$ over a 2-week period. Peptide controls ($ASP_{40}$ and PBAN) were used to explore the specificity of this response. FIGS. 11D-11E and Table 4 present the resultant cell growth and changes in the populations that emerged from a typical CD34+ culture. Incubation with $ARP_{26}$, but not with cortisol, $ASP_{40}$ or PBAN, increased the total number of cells. A larger fraction of committed progenitors (CD34+CD38+) emerged in the presence of cortisol at stress levels (1.2 μM) as compared to a physiologically relevant concentration of $ARP_{26}$ (FIG. 11D-11E); however, the expansion index (the number of viable cells/ml culture divided by the number of seeded cells) was considerably higher following incubation with $ARP_{26}$ (Table 4a). Increases were observed along the entire myelopoietic differentiation pathway (CD34+CD33+, CD33+CD15−, CD33+CD15+ and CD33−CD15+, Table 4b), supporting the notion that $ARP_{26}$ tilts hematopoiesis towards the myeloid lineage in a cortisol-independent process, and particularly expanding the population of mature CD33−CD15+ granulocytes (see column CD33−CD15+, Table 4b), inducing increased growth of early GEMM progenitors and producing specifically large numbers of mature granulocytes. These findings demonstrate that the $ARP_{26}$-induced myelopoiesis in fact leads to an enrichment of the granulocytic population.

TABLE 4a $ARP_{26}$ promotes ex vivo cell expansion of cultured CD34+ cells

| Treatment | Cell type Cell expansion index[a] |
|---|---|
| Control | 0.59 ± 0.76 |
| Cortisol, 1.2 μM | 1.55 ± 0.07 |
| $ARP_{26}$, 2 nM | 5.29 ± 2.52* |
| $ASP_{40}$, 2 nM | 1.9 ± 0.61 |
| PBAN, 2 nM | 1.85 ± 0.96 |

[a]The number of viable cells/ml culture at day 14 divided by the number of seeded cells (50,000).
*P < 0.001

TABLE 4b

The effect of various conditions on cultured CD34+ cells.
The numbers represent actual cell counts × $10^3$ of each cell type detected

| Treatment | Cell expansion index[a] | CD34+ CD38+ Committed progenitors | CD34+ CD33+ Committed myeloids | CD33+ CD15− Immature myeloids | CD33+ CD15+ Granulocytes | CD33− CD15+ Mature granulocytes |
|---|---|---|---|---|---|---|
| Control | 1.2 | 0.5 | 0.5 | 1.4 | 2.1 | 4.3 |
| Cortisol (1.2 nM) | 1.6 | 11.0 | 10.6 | 13.0 | 28.5 | 15.4 |
| ARP$_{26}$ (2 nM) | 11.4 | 29.1 | 31.9 | 94.6 | 64.4 | 220.6 |
| ASP (2 nM) | 2.0 | 2.5 | 0.4 | 0.5 | 1.9 | 4.2 |
| PBAN (2 nM) | 2.1 | 0 | 0.1 | 0.2 | 0.9 | 1.8 |

[a]Expansion index is a ratio of the number of viable cell/ml culture at day 14 divided by the number of cells seeded (50,000).

Example 14

AChE-R Supports Pro-Inflammatory Cytokine Release from Mononuclear Cells

Next, the putative mechanism(s) enabling the long term effects of ARP$_{26}$ was addressed. The elevated AChE-R contents and AChE activity in the post-partum blood predicted peripherally reduced ACh levels, and the suppressed cholinergic control over the production of pro-inflammatory cytokines by macrophages. The levels of several inflammation/stress-associated cytokines in the plasma of intra-partum mothers were compared to those of non-pregnant women. Elevation was observed for IL-1β, IL-6 and TNFα, all known to have pro-inflammatory and hematopoietic roles, in the post-partum mothers [Hanada and Yoshimura (2002) Cytokine Growth Factor Rev. 13: 413-421; Wilson et al. (2002) J. Am. Geriatr. Soc. 50: 2041-2056] (FIG. 12A). To examine whether this increase could be causally related with AChE-R overexpression in peripheral white blood cells, $2.5 \times 10^6$ mononuclear cells per mL from adult women controls were incubated with 2 nM ARP (FIG. 12B). Significant increases were observed in the secretion from these cell cultures of IL-1β, IL-6 and TNFα 24 hours later, but there was no change in the release of the anti-inflammatory cytokine IL-8 from cells incubated with ARP$_{26}$ as compared with control cells (FIG. 12A and data not shown). Thus, the post-partum AChE-R overexpression in peripheral nucleated blood cells could be causally associated with selective elevation of pro-inflammatory cytokines.

Example 15

AChE-R Excess is Associated with Impaired Response to LPS

In order to understand the mechanisms of the hematopoietic effect of prolonged exposure to AChE-R, the transgenic AChE-R (TgR) mouse model was used. Basal levels of white blood cell counts (WBC) were similar in both TgR and FVB/N mice (FIG. 14A-14B). Manual differential of WBC sub-populations showed similar distributions into granulocytes, monocytes and lymphocytes in TgR and FVB/N mice (FIG. 14A-14B). These findings may reflect an equilibrium state of the hematopoietic system reached by the TgR mice. Therefore it was demanding to expose these mice to an acute stressful event.

LPS was injected intra-peritoneally (IP) in order to induce acute inflammation WBC counts dropped in both FVB/N and TgR mice. However, counts recovered much faster in TgR mice to reach significantly higher levels than those of FVB/N mice by 72 hr post LPS injection ($p<0.02$, $n=10$, FIG. 14B). Peripheral blood immunophenotyping revealed that while FVB/N mice had a significant decrease in GR1$^+$ (granulocyte) cells, in response to LPS injection, the number of GR1$^+$ remained unchanged in TgR mice and was significantly higher than FVB/N by 72 h post LPS injection. Both FVB/N and TgR mice had decreased CD11b+ (monocytic) cell counts 24 h post LPS injection, although the decrease was steeper in TgR as compared to FVB/N mice. CD11b+ cell counts recovered almost completely by 72 h post LPS injection in both FVB/N and TgR mice, TgR mice attaining higher Cd11b+ counts, although not reaching a statistically significant value. These data suggest that the early recovery in WBC counts in TgR in response to inflammatory stress, results from both their ability to maintain stable granulocyte counts, in spite of the LPS suppressive effects, as well as to a rapid renovation of the monocyte pool.

Example 16

PU.1 Transcription Factor is Involved in the Inflammatory Response

To further understand TgR peripheral cell response to inflammatory stress, the expression pattern of transcription factors pivotal for hematopoiesis in bone marrow extracts from FVB/N and TgR mice was evaluated, through real time RT-PCR (FIG. 13).

While the response pattern of LMO2, GATA1, RUNX1 and STAT5 to LPS was similar in both FVB/N and TgR mice, PU.1 levels decreased significantly in FVB/N, but not in TgR mice bone marrow, in response to LPS. At 72 h post LPS injection, PU.1 levels recovered and even reached higher than base-line values in FVB/N mice, but showed only some decrease in TgR mice.

Example 17

AChE-R is Expressed in Bone Marrow and Blood of TgR Mice

The inventors' previous reports suggest that a stress-induced switch from production of AChE-S to the -R variant elevates soluble AChE-R levels [Pick (2004) id ibid.]. Thus, it was hypothesized that this shift may reduce circulating ACh and the nicotinic α7 ACh control over pro-inflammatory cytokine production [Tracey K. J. (2002) id ibid.], driving hematopoietic progenitor cell expansion, as previously described [Grisaru (2001) id ibid.] (FIG. 16A). TgR mice were then used as a model of chronic splicing shift towards the AChE-R, over the AChE-S transcript. Using DNA primers specific for human AChE intron 4, human AChE-R mRNA was detected in the BM of TgR mice but not in strain-matched FVB/N mice or in the TgS mice over-expressing the AChE-S variant, (FIG. 16B), reconfirming the continued activity of the transgene in hematopoietic cells.

Example 18

AChE-R Excess is Associated with Elevated Basal and Post-Stress Platelet Counts

As mentioned before, basal levels of WBC were similar in TgR and FVB/N mice (FIG. 14A-14B and 17B). Basal levels of thrombopoietin (TPO) were similar in both TgR and FVB/N mice (FIG. 17A), whereas platelet counts were significantly higher in TgR mice (894±87 Vs 1051±160×10$^9$/mL, p<0.001, n=25, FIG. 17C). Since manual differential of WBC sub-populations showed similar distributions into granulocytes, monocytes and lymphocytes in TgR and FVB/N mice (FIG. 14A-14B and 17B), the results with the platelets reflect selective thrombocytosis under chronic AChE-R overexpression.

After ip LPS injection RBC counts predictably dropped up to 72 hrs post-LPS (FIG. 16) in control FVB/N but not TgR mice. WBC dropped in both strains, but counts recovered considerably faster in TgR mice reaching significantly higher levels than those of FVB/N control mice by 72 hr post LPS injection (p<0.02, n=10, FIGS. 16B and 16D). Platelet counts in FVB/N control mice dropped significantly, as expected, to thrombocytopenic levels between 24 and 72 hrs, while in TgR mice the platelet counts were only slightly reduced and returned to normal values within 72 hrs (p<0.001, n=10, FIG. 16C).

Example 19

AChE-R Over-Expression Modulates TPO and Inflammatory Cytokine Levels

To further study the observation of elevated platelet counts in TgR mice, TPO concentrations were measured in the plasma and BM cell extracts from TgR and FVB/N mice. TPO concentrations were significantly higher in both BM and plasma of TgR mice (p=0.013, 0.04 respectively, compared to FVB/N control mice (FIG. 17A and 17B), consistent with the notion that these mice can serve as a model of chronic inflammation [Stohlawetz (1999) id ibid.; Kaser A. et al. (2001) Blood 98: 2720-2725; Zahorec R. (2001) Bratisl. Lek. Listy. 102:5-14]. TgR mice BM had higher TPO levels 24 hrs post LPS injection (p=0.002) followed by lower TPO levels at 72 hrs (p=0.02, n=10, FIG. 3A), as compared with FVB/N mice. In plasma, the high basal TPO levels were maintained 24 hrs post LPS injection (p=0.01, n=10). However, at this time point the FVB/N mice plasma TPO levels were significantly higher than TgR mice possibly due to corresponding dramatic drop in platelet numbers (FIG. 17B). TPO levels decreased slightly but remained elevated in both mouse strains at 72 hrs (FIG. 17B).

Example 20

AChE-R Over-Expression is Associated with Modified Inflammatory Cytokine Levels

To study the possible effects of AChE-R in the inflammatory reaction, the inventors measured the levels of inflammatory cytokines in plasma and BM extracts of TgR and FVB/N mice. IL-6, but not TNFα levels were found to be significantly elevated in the plasma of TgR mice as was AThCh hydrolyzing activity compared with FVB/N control mice, suggesting that AChE catalytic activity might be involved in modified inflammatory control (FIG. 15C).

The inflammatory response of TgR mice was further evaluated by measuring the levels of TNFα and IL-6, in bone marrow cell extracts and plasma, and at different time points post injection of LPS. TgR mice showed significantly higher plasma levels of TNFα 2 hrs post LPS injection (34±231 pg/mL, p<0.04, n=10) but significantly lower levels in BM, as compared to FVB/N mice (120±66 Vs 334±81, p<0.01, n=10) (Table 5A) possibly because the main production TNFα is in peripheral blood. IL-6 levels were comparable in both TgR and FVB/N mice after LPS injection (Table 5A), indicating again a preexisting active inflammatory state in the TgR strain.

TABLE 5A

| Inflammatory cytokine levels post LPS | | | | |
|---|---|---|---|---|
| | TNFα (pg/ml)[a] | | IL-6 (pg/ml)[a] | |
| | plasma | BM | Plasma | BM |
| TgR | 834 ± 231 | 120 ± 66 | 1418 ± 62 | 507 ± 135 |
| FVB/N | 538 ± 217 | 334 ± 81 | 1378 ± 40 | 498 ± 331 |
| P | 0.04 | 0.01 | NS | NS |

[a] TNFα and IL-6 levels were measured 2 hours post-LPS injection.

In addition to their high baseline AChE catalytic activity (FIG. 15C), TgR mice responded to LPS injections by a further significant increase in bone marrow AChE catalytic activity 24 hrs post LPS injection (p=0.0004, n=10), but not at other time points (Table 5B).

TABLE 5B

| AThCh hydrolysing activity/min/mg of protein post LPS | | | | |
|---|---|---|---|---|
| | BM LPS (hrs post) | | Plasma LPS (hrs post) | |
| | 24 | 72 | 24 | 72 |
| TgR | 14.2 ± 4.3 | 13.1 ± 1.8 | 31.7 ± 12.8 | 7.7 ± 0.4 |
| FVB/N | 6.3 ± 1.9 | 11.0 ± 0.7 | 27.0 ± 13.1 | 9.3 ± 1.0 |
| P | 0.00004 | NS | NS | NS |

Note:
AChE catalytic activity assessed by its AThCh hydrolyzing activity/mim/mg protein was measured in plasma and bone marrow extracts of LPS-injected mice (n = 10) Shown are average concentrations ± SD in plasma or BM proteins.

Example 21

Enhanced Proliferative Potential in Bone Marrow Progenitors from TgR Mice

The proliferating potential of BM progenitor cells was evaluated by clonogenic assays using growth factors to support the development of the specific hematopoietic lineages. Colonies were classified as colony forming units-megakaryocyte (CFU-Mk), CFU-granulocyte/macrophage (CFU-GM) or CFU-granulocyte/erythrocyte/monocyte/megakaryocyte (CFU-GEMM) and were counted 10 to 14 days after plating. TgR mice showed significantly higher baseline numbers of CFU-Mk, -GM and -GEMM hematopoietic progenitor cells as compared to FVB/N controls (p≦0.003, n=12, FIGS. 18A-21C). Following LPS injection, TgR mice maintained significantly higher number of megakaryocyte progenitors (p<0.0002, n=12, FIG. 18A). In FVB/N mice, the number of CFU-GM, was significantly elevated at 24 hr post-LPS, a response previously described [Peterson (1992) id ibid.; Yokochi (1985) id ibid.] (p=0.01, n=12, FIG. 18B) but decreased noticeably by 48 hr, while TgR CFU-GM numbers decreased 48 hr post LPS injection but remained significantly higher than FVB/N (p=0.03, n=12, FIG. 18B). The increase in CFU-GM in TgR mice was less dramatic than in FVB/N control mice perhaps caused by fatigue of myeloid progenitor cells due to chronic exposure to ACHE-R. TgR and FVB/N mice showed similar post-LPS numbers of multipotential CFU-GEMM (NS, n=12, FIG. 18C).

Example 22

AChE-R Over-Expression Associates with Elevated Megakaryocytic PKCε

AChE-R was reported to interact with the scaffold protein RACK1 and with its target, protein kinase C βII (PKC βII) [Birikh K. R. et al. (2003) Proc. Natl. Acad. Sci. USA 100: 283-288; WO 00/73427] or PKC 6 [Perry C. et al. (2004) Neoplasia 6(3):279-86]. PKCε has been implicated in the programming of megakaryocytic lineage commitment and potentiates the transcription factor GATA-1 [Racke F. K. et al. (2001) J. Biol. Chem. 276:522-528]. To study a potential AChE-R/PKCε/RACK1 interaction in megakaryocytes, AChE-R, PKCε and RACK1 were detected in BM smears of TgR and FVB/N mice (FIGS. 19A-19F).

Megakaryocytes were detected in BM smears by the May-Grünwald staining (FIG. 19A). TgR megakaryocytes predictably expressed higher AChE-R labeling then megakaryocytes from FVB/N mice (212.3±15.0 Vs 130.9±18.3 luminescence units, p<$10^{-11}$, n=50, FIGS. 19B, 19F and Table 3). Intriguingly, RACK1 labeling intensity was discernable, although insignificantly elevated in TgR megakaryocytes, as compared to FVB/N mice (162.3±49.2 Vs 153.4±21.0, NS, n=50, FIGS. 19C, 19F and Table 6). No differences in the number of PKC ε-labeled megakaryocytes were detected in TgR mice (data no shown), nevertheless, the intensity of PKC F labeling was significantly higher as compared to FVB/N mice (187.7±22.2 Vs 160.9±19.7 luminescence units, p<$10^{-5}$, n=50, FIGS. 19D, 19F and Table 6). Thus, AChE-R interaction with RACK1 and with PKCε emerged as a putative mechanism for increased intracellular signaling in TgR megakaryocytes.

TABLE 6

Luminescence intensity of human AChE-R, RACK1 and PKCε in megakaryocytes.

| Antibody | FVBN | TgR | p values |
| --- | --- | --- | --- |
| No Antibody | 116.8 ± 8.7 | 122.4 ± 11.8 | NS |
| Hu AChE-R | 130.94 ± 18.26 | 212.3 ± 15.0 | $1 \times 10^{-11}$ |
| RACK1 | 153.4 ± 21.0 | 162.3 ± 49.2 | NS |
| PKCε | 160.9 ± 19.7 | 187.8 ± 22.7 | $3 \times 10^{-6}$ |

Note:
Luminescence levels (from 1, low luminescence to 220, bright) were determined using a upright Zeiss microscope, ImagePro ™ image capture and Adobe Photoshop V 5.5 analysis for each megakaryocyte stained in the bone marrow smears (n = 50 per antibody). NS = Not significant. Background staining was detected by incubation with no primary antibody.

Example 23

AChE-R Potentiates Engraftment Potential in NOD/SCID Mice

TgR mice elevated platelet counts and increased megakaryocyte growth potential was suggestive to determine whether AChE-R, or its cleavable peptide ARP, can improve engraftment of transplanted BM cells and recovery from thrombocytopenia in a NOD/SCID mouse transplantation model. Human CB CD34$^+$ cells were primed for 2 hrs prior to injection with ARP$_{26}$, a synthetic peptide comprised of 26 amino acids of the C-terminal sequence of AChE-R or ASP$_{40}$ a 43 amino acid sequence of the C terminus of AChE-S. The ARP concentration chosen (2 nM) was previously determined to be maximal for stimulating hematopoietic stem cell proliferation [Deutsch (2002) id ibid.] Human CB CD34$^+$ cells ($1 \times 10^5$) were injected into mice 24 hours post irradiation. Cells were either primed and supplemented with ARP$_{26}$ or primed and supplemented with ASP$_{40}$ or untreated (control). Mice were sacrificed 6 weeks post-transplantation and single cell suspensions from BM extracted from the femur bones assessed for the presence of human hematopoietic cells Monoclonal antibodies against human CD45, CD34 and CD41 were used to assess engraftment efficacy of the transplanted human cells. Fractions of human CD34$^+$ cells in the BM of NOD/SCID mice post transplant were similar in all groups (FIG. 20A). However, significantly more human CD45$^+$ cells were found in the BM of NOD/SCID mice injected with ARP$_{26}$ together with ARP$_{26}$-primed CD34$^+$ cells (p=0.02, n=12, 16 and 8 mice, respectively, FIG. 20A). Fractions of human megakaryocytes (CD41$^+$) were higher in the BM of NOD/SCID mice that received ARP$_{26}$-primed cells as compared with ASP$_{40}$-primed or non-primed human cells (p=0.03, n=12, 16 and 8 mice, respectively, FIG. 20A). These results demonstrate a significantly better engraftment of transplanted primed human CD34$^+$ cells when injected with ARP$_{26}$ as compared with non-ARP$_{26}$ treated cells.

Quantitative PCR with human specific probes was used to assess the relative presence of human DNA in the BM of NOD/SCID mice. Significant differences could be observed between mice transplanted with ARP$_{26}$-primed CD34$^+$ cells as compared to cells primed with ASP$_{40}$ or non-primed cells (p=0.015, FIG. 20B).

Example 24

Transplantation of Cells Expanded Ex Vivo with ARP$_{26}$ Increased Human Platelet Production in NOD/SCID Mice In an attempt to improve platelet recovery in NOD/SCID mice the number of committed megakaryocyte progenitor cells in the stem cell graft were expanded ex-vivo. CD34$^+$ cells were incubated for 10 days in medium supplemented with 10% plasma and one of the following combinations: ARP$_{26}$, (2 nM) ASP$_{43}$ (2 nM), TPO (10 ng/ml) and SCF (50 ng) (growth factors optimal for megakaryocyte commitment) or no growth factor supplement (control). CD34+ cells are known to differentiate in culture producing many committed progenitors, but have reduced capacity for long-term engraftment in NOD/SCID mice. Therefore, freshly isolated CD34$^+$ cells are needed to enable long-term engraftment [Guenechea G. et al. (1999) *Blood* 93:1097-1105; Li K. et al. (1999) *Br. J. Haematol.* 104:178-185]. For this reason a mixture of cultured CD34$^+$ cells (between 1-2×10$^5$) was injected together with 100,000 fresh CB CD34$^+$ cells. The cultured CD34$^+$ cells, being more mature were expected to facilitate the capacity for early platelet production. Early engraftment (2-3 weeks post-transplant) and late engraftment (4 and 6 weeks post-transplant) were analyzed. Incubating CD34$^+$ cells with ARP$_{26}$, ASP$_{40}$ or TPO and SCF did not augment engraftment of human CD45$^+$, CD34$^+$ or CD41$^+$ cells (FIG. 21A) however, it enabled to test whether the injected differentiated cells affected platelet production. Full blood cell counts were performed on the transplanted NOD/SCID mice and the presence of human platelets monitored. Although significant differences were not found, probably due to the small sample number of mice (n=6), NOD/SCID mice that received cells expanded with ARP$_{26}$ yielded higher human platelet numbers, both early (between 2 and 3 weeks post-transplant) (mean=1.26 control Vs 3.29 ARP$_{26}$ expanded Vs 0.94 ASP$_{40}$ expanded Vs 1.61×10$^6$/ml TPO/SCF expanded group, FIG. 21B) and at the late transplanted stage (mean=5.85 control Vs 17.70 ARP$_{26}$ expanded Vs 6.39 ASP$_{40}$ expanded Vs 3.44× 10$^6$/ml TPO/SCF expanded group, FIG. 21B). These observations were compatible with the hypothesis that the injected differentiated megakaryocytes facilitated platelet production in the engrafted mice and that the enhanced AChE-R production by these cells support a shift towards megakaryocytopoiesis, which culminated in higher platelet counts at the later test time.

The invention claimed is:

1. A method for inducing a shift in the activity of lymphocytes in vitro or ex vivo, comprising contacting an acetylcholinesterase (AChE)-derived peptide with lymphocytes for a suitable period of time, wherein the AChE-derived peptide comprises the amino acid sequence set forth in SEQ ID NO:1.

2. A method of treatment of conditions wherein lymphocyte activity is reduced in a subject in need thereof, said method comprising:
    (a) obtaining blood from a subject;
    (b) isolating immature cells from the blood;
    (c) contacting the immature cells with an acetylcholinesterase (AChE)-derived peptide; and
    (d) introducing the immature cells into the subject, wherein said peptide is denoted by SEQ ID NO:1 and wherein the condition is selected from the group consisting of chronic stress, autoimmune diseases, inflammation, rheumatoid arthritis, multiple sclerosis (MS), amyotrophic lateral sclerosis (ALS), fibromyalgia, multiple chemical sensitivity, post-irradiation, and chemotherapy.

3. A method of priming hematopoietic stem cells pre-transplant, comprising obtaining said cells, isolating from said cells an immature, CD34+ rich population, and exposing said cell population to an AChE-derived peptide or compositions comprising thereof, wherein the AChE-derived peptide comprises the amino acid sequence as set forth in SEQ ID NO:1.

4. The method as defined in claim 3, wherein said cells may be obtained from a subject in need of said transplant or from another donor.

5. The method of claim 2, wherein the immature cells obtained from the subject in step (a) are introduced in step (d) to the same subject.

6. The method of claim 2, wherein the immature cells obtained from the subject in step (a) are introduced in step (d) to a different subject.

* * * * *